United States Patent
Arie

(10) Patent No.: US 8,426,139 B2
(45) Date of Patent: Apr. 23, 2013

(54) POLYPEPTIDES FOR IDENTIFYING IN VITRO AND PREVENTING STAPHYLOCCOCAL INFECTIONS ON JOINT PROSTHESES AND OTHER IMPLANTED FOREIGN MATERIALS

(75) Inventor: Jean-Philippe Arie, Lyons (FR)

(73) Assignee: InGen Biosciences, Chilly Mazarin (FR)

( * ) Notice: Subject to any disclaimer, the term of this patent is extended or adjusted under 35 U.S.C. 154(b) by 1169 days.

(21) Appl. No.: 12/299,971

(22) PCT Filed: May 4, 2005

(86) PCT No.: PCT/FR2005/001120
§ 371 (c)(1),
(2), (4) Date: Oct. 9, 2009

(87) PCT Pub. No.: WO2006/005825
PCT Pub. Date: Jan. 19, 2006

(65) Prior Publication Data
US 2010/0196422 A1    Aug. 5, 2010

(30) Foreign Application Priority Data

Jun. 8, 2004  (FR) ...................................... 04 06154
Apr. 28, 2005  (FR) ...................................... 05 04287

(51) Int. Cl.
*G01N 33/569* (2006.01)
(52) U.S. Cl.
USPC ............................................................ 435/7.1
(58) Field of Classification Search .................... None
See application file for complete search history.

(56) References Cited

U.S. PATENT DOCUMENTS 6,380,370 B1 * 4/2002 Doucette-Stamm et al. 536/23.1

OTHER PUBLICATIONS http://www.uniprot.org/uniprot/q8cpq1#section_customize[Nov. 10, 2011 4:57:22 PM], accessed Nov. 10, 2011.*

* cited by examiner

*Primary Examiner* — Brian J Gangle
(74) *Attorney, Agent, or Firm* — Young & Thompson

(57) ABSTRACT

The invention concerns novel polypeptides, or parts or variants of the novel polypeptides, the use of sequences encoding the polypeptides and the use of antibodies directed against the polypeptides in the field of in vitro diagnosis of a *Staphylococcus epidermidis* and/or *Staphylococcus aureus* infection on foreign material implanted in the body.

17 Claims, No Drawings

POLYPEPTIDES FOR IDENTIFYING IN VITRO AND PREVENTING STAPHYLOCCCOCAL INFECTIONS ON JOINT PROSTHESES AND OTHER IMPLANTED FOREIGN MATERIALS

The present invention relates to a tool for serological multiparameter diagnosis of staphylococcal infections on joint prostheses (for example infection on a hip, elbow, knee, ankle prosthesis, etc.) and, more generally, diagnosis of staphylococcal infections on foreign material implanted in the body.

In particular, the invention comprises the identification of novel polynucleotides and polypeptides as well as the production, optimisation and use thereof, on the one hand within the field of diagnosing infections on foreign material (joint prostheses for example) involving *Staphylococcus aureus* and/or *Staphylococcus epidermidis* and, on the other hand, within the field of producing vaccines against said different agents.

Infections on joint prostheses are a major problem in public health. Hundreds of thousands of joint prostheses are implanted worldwide every year and millions of people have one or more (Lew et Waldvogel, 1997, Osteomyelitis, *N Engl J Med* 336:999-1007). In the United States of America, it is estimated that approximately 430,000 total hip prostheses (THPs) and total knee prostheses (TKPs) are implanted every year (Berbari et al., 1998, *Clin Infect. Dis.,* 27:1247-1254). In Norway and Sweden, the only countries in which there is a register of prostheses, 250,000 THPs were implanted within the space of ten years between 1987 and 1996 (Lidgren, 2001, Joint prosthetic infections: a success story, *Acta Othop Scand* 72:553-556). In France, according to the French Society of Orthopaedics, the number of prostheses implanted every year is approximately 100,000 for THPs and 25,000 for TKPs (National Agency for Accreditation and Evaluation in Health, 2000). These figures will continue to rise in future owing to ageing populations (implantation of THPs) and obesity-related problems (implantation of TKPs) in developed countries.

Despite the considerable progress made in recent years, prosthetic joint infections (PJIs) are still a common complication affecting between 0.3 and 1.8% of patients in the case of THPs (Berbari et al., 1998 [already cited]; Lidgren, 2001 [already cited]) and between 0.5 and 5% of patients in the case of TKPs (Johnson et Bannister, 1986, The outcome of infected arthroplasty of the knee, *J Bone Joint Surg* 68:289-291; Bengtson et Knutson, 1991, The infected knee arthroplasty, A 6-year follow-up of 357 cases, *Acta Othop Scand* 62:301-311; Eveillard et al, 2002, Risque infectieux après implantation de prothèses de genou, Etude des infections profondes pour une série continue de 210 prothèses totales de genou en première intention, *B E H No.* 13). These rates are even higher when it comes to replacement. Infection may occur at any time after implantation of the prosthesis. In a large American study of more than 25,000 patients who have a THP or a TKP, the average period of time between implanting the prostheses and diagnosis of infection was 512 days, with periods ranging from 3 days to nearly 20 years and being distributed as follows: 20% of infections diagnosed within 3 months following implantation, 40% between 3 months and 2 years, and 40% beyond 2 years (Berbari et al., 1998 [already cited]).

PJI is a dangerous complication, resulting in the need for one or more revision surgeries in combination with long-term antibiotherapy, however, long-term functional handicap, a risk of amputation or even death may also occur (Segawa et al, 1999, Infection after total knee arthroplasty, *J Bone Joint Surg Am* 81:1434-1445). The socio-economic impact of a PJI is also extremely high, with an estimated cost of more than 50,000 dollars per case (Sculco, 1995, The economic impact of infected joint arthroplasty, *Orthopedics* 18:871-873).

Staphylococci

Bacteria of the *Staphylococcus* genus are stationary, non-spore-forming, catalase-positive, oxidase-negative, gram-positive cocci grouped together in grape-like clusters. Observed by Pasteur in 1879 in furuncle pus, staphylococci owe their name to Ogsten (1881) who isolated them in acute chronic abscesses.

*S. aureus* (more commonly known as golden staph) is generally distinguished from other species of staphylococci. Unlike *S. aureus* these other species do not produce any coagulase enzyme and, for this reason, are grouped separately under the term "coagulase-negative staphylococci" (CNSs).

Habitat of Staphylococci

The natural habitat of *S. aureus* is humans and warm-blooded animals. In humans, *S. aureus* preferably resides in nasal mucous; up to 30% of adults permanently harbour *S. aureus* in their nostrils and 50% harbour it intermittently. Apart from the nose, *S. aureus* also resides on the skin and, in particular, in moist regions (armpits, perineum) and on the hands. Small amounts of *S. aureus* can also be found in the intestine. Lastly, the immediate environment of a human is also a source of potential contamination owing to the persistence of *S. aureus* in the external environment once it has been eliminated.

CNSs are the main commensals of skin together with coryne bacteria and propionibacteria. The density of colonisation is greater in moist regions, such as the anterior portion of the nostrils, the perineum, the armpits and the inguinal folds. Intra-human or inter-human transmission generally occurs by direct contact (for example via the hands). More rarely, transmission may be indirect from an environmental source (clothing, sheets, medical equipment).

Normally present in large quantities on skin and in mucosae, *S. epidermidis* and the other CNSs may contaminate superficial samples or samples obtained by transcutaneous puncture, such as blood cultures, or even deep perioperative samples taken during surgery. Consequently, CNSs are only considered responsible for an infection if this bacteria is found multiple times in samples taken independently.

Role of Staphylococci in Human Pathology

*S. aureus* is responsible for many different infections. Cutaneo-mucosal infections, such as folliculitis, impetigo, furuncles, anthrax, panaris, cellulitis, sinusitis or otitis are the most common. These infections may be complicated by the loco-regional extension or hematogenous diffusion of the bacteria. *S. aureus* thus causes septicaemia, endocarditis, pneumopothy, ostheomyelitis, arthritis and meningitis. These infections may be life-threatening, either per se (for example by attacking a heart valve) or in the case of associated toxic shock.

*S. aureus* has long been considered the only pathogenic staphylococcus in humans, whilst CNSs were viewed as mere contaminants. The major role of CNSs in human pathology has only recently been established, in particular in patients with joint prostheses, artificial heart valves or implantable devices such as vascular catheters or shunts for diverting cerebrospinal fluid.

*S. epidermidis* is the CNS which is most frequently isolated in infections on foreign material. Other CNSs which are involved in this type of infection include *S. capitis, S. caprae, S. haemolyticus, S. lugdunensis, S. schleiferi, S. simulans* and *S. warneri*.

Staphylococci are the main agents of PJIs and other infections on foreign materials.

Staphylococci are the bacteria most often found in PJIs and other infections on foreign materials, accounting for up to 75% of isolated bacteria, *S. aureus* and *S. epidermidis* being the prevalent species (Lew et Waldvogel, 1997 [already cited]). According to studies, the group of CNSs headed by *S. epidermidis* is alone responsible for 20 to 40% of cases and ranges from being either the most common or second-most common behind *S. aureus*.

Apart from *S. epidermidis*, prevalent CNSs are *S. capitis, S. caprae, S. haemolyticus, S. lugdunensis, S. schleiferi, S. simulans* and *S. warneri*. Among these species, *S. capitis, S. caprae* and *S. lugdunensis* are the main CNSs, apart from *S. epidermidis*, responsible for prosthetic joint infections and, more generally, osteoarticular infections on foreign material (joint prostheses, osteosynthesis materials) (Rupp et Archer, 1994, Coagulase-negative staphylococci: pathogens associated with medical progress, *Clin Infect Dis* 19:231-243; Crichton et al, 1995, Subspecies discrimination of staphylococci from revision arthroplasties by ribotyping. *J Hosp Infect* 30:139-147; Blanc et al, 1999, Infection after total hip replacement by *Staphylococcus caprae*. Case report and review of the literature, *Pathol Biol* 47:409-413; Sampathkumar et al, 2000, Prosthetic joint infection due to *Staphylococcus lugdunensis*. *Mayo Clinic Proc* 75:511-512; Weightman et al, 2000, Bone and prosthetic joint infection with *Staphylococcus lugdunensis, J Infect* 40:98-99).

Generally, PJIs and other infections on foreign material caused by *S. aureus* are most often acute and suppurative owing to the numerous enzymes and toxins produced by this species (Nair et al, 2000, Advances in our understanding of the bone and joint pathology caused by *Staphylococcus aureus* infection, *Rheumatology* (Oxford) 39:821-834), whilst CNS infections are mild and are often chronic (Von Eiff et al, 2002, Pathogenesis of infections due to coagulase-negative staphylococci, *Lancet Infect Dis* 2:677-685). However, this is not always the case: *S. aureus* infections may often be chronic whilst infections caused by CNSs, such as *S. lugdunensis*, may develop acutely (Sampathkumar et al, 2000 [already cited]; Weightman et al, 2000 [already cited]).

Characteristics of Staphylococcal Infections on Foreign Material with Biofilm Formation Staphylococcal infections on foreign material differ from conventional infections by the arrangement of bacteria in the form of biofilm (Costerton et al, 1999, Bacterial biofilms: a common cause of persistent infections, *Science* 284:1318-22). This process has been described with reference to numerous staphylococci including *S. aureus* but has been studied, above all, in the case of *S. epidermidis* (Von Eiff et al, 2002 [already cited]).

Biofilm is a complex three-dimensional structure which is connected to the foreign material and in which the bacteria cells are embedded in a polysaccharide extracellular matrix called slime or glycocalyx (Davey and O'Toole, 2000, Microbial biofilms: from ecology to molecular genetics, *Microbiology and Molecular Biology Reviews* 64:847-867). This specific structure may be formed by bacteria of the same species or of different species (Costerton et al, 1995, Microbial biofilms, *Ann Rev Med* 49:711-745; Watnick and Kolter, 2000, Biofilms, city of microbes. *J Bacteriol* 182:2675-2679). In comparison with their living consgeners in free (or 'planctonic') form, these bacteria are in a state of quiescence indicated by a low level of metabolic activity (Yao et al, 2005, Genomewide analysis of gene expression in *Staphylococcus epidermidis* biofilms: insights into the pathophysiology of *S. epidermidis* biofilms and the role of phenol-soluble modulins in formation of biofilms, *J Infect Dis* 191:289-298).

Infections on foreign material associated with biofilm formation have a number of features which distinguish them completely from conventional tissue infections. These infections are most often paucibacillary (having few bacteria) and readily polymicrobial (combination of a plurality of species; for example, *S. aureus* and *S. epidermidis* or *S. epidermidis* and one or more other CNSs (Costerton et al, 1995 [already cited]; Watnick et Kolter, 2000 [already cited]). The bacteria have a very slow metabolism which keeps them in a state close to dormancy and the genes which they express are different to those activated in planctonic forms (Yao et al, 2005 [already cited]). The state of dormancy of the bacteria and the presence of the biofilm significantly reduce the inflammatory reaction and the attraction of immune cells at the infection site. (Vuong et al, 2004, Crucial role for exopolysaccharide modification in bacterial biofilm formation, immune evasion, and virulence, *J. Biol. Chem,* 279, 52:54881-54886; Fux et al, 2003, Bacterial biofilms: a diagnostic and therapeutic challenge, *Expert Rev Anti Infect Ther,* 1:667-83). Lastly, for the same reasons, the bacteria are largely protected from the action of antibiotics (Costerton et al, 1995 [already cited]).

Current Methods for Diagnosing Staphylococcal Infections in a Laboratory Bacteriological Diagnosis Nowadays, bacteriological diagnosis of a staphylococcal infection is almost exclusively direct by isolating the bacteria in relevant samples.

Diagnosis is based on the following main steps:

(1) aseptic sampling (to reduce the risk of contamination by way of a simple commensal staphylococcus on the skin) carried out with no concurrent antibiotherapy (after stopping or before starting antibiotic treatment).

(2) microscopic examination which enables common, gram-positive cocci grouped together in grape-like clusters to be observed. This examination is completely insensitive and gives no indication of the species involved.

(3) culture on ordinary agar in the majority of cases or on a selective culture medium, CHAPMAN-type medium (which contains 7% NaCl, mannitol and a pH indicator) if the sample is potentially contaminated by other bacteria.

(4) identification of the bacteria is based on the isolation of the following features:

catalase (differentiation from streptococcus),
anaerobic glucose fermentation (differentiation from micrococcus),
coagulase (differentiation from CNSs),
thermostable Dnase (which indicates the *S. aureus* species),
mini identification gallery (manual or automated) (identification of CNS species)
optionally, molecular identification (for example, sequencing of the sodA gene) (identification of CNS species).

(5) The diagnosis is completed by measuring sensitivity to antibiotics (antibiogram) given the frequency of resistance of staphylococci, in particular in the case of hospital strains. The profile of sensitivity to antibiotics is also beneficial, although imperfect, for comparing different strains (for true typing it is necessary to use molecular techniques such as pulse field gel electrophoresis or multilocus sequence typing).

The main drawback relates to the interpretation of the culture results since staphylococci are common contaminants. The general rule applied in order to establish a diagnosis of infection is as follows:

*S. aureus*: at least one positive relevant sample (for example a blood culture), CNS: at least two independent relevant samples (for example two blood cultures taken at two different times) which are positive for the same bacterium (i.e, in standard practice a bacterium of the same species and having the same sensitivity to antibiotics).

This threshold of two positive samples in the case of CNSs has recently been called into question within the context of PJIs as it is considered to be too nonspecific, and some authors maintain that, from now on, a threshold of three positive perioperative samples will be necessary to diagnose PJI caused by CNS (Atkins et al, 1998, Prospective evaluation of criteria for microbiological diagnosis of prosthetic-joint infection at revision arthroplasty, *J Clin Microbiol* 36:2932-2939).

Serological Diagnosis

Nowadays, indirect diagnosis of staphylococcal infection by identifying circulating antibodies is largely undeveloped and is only relevant to the diagnosis of some severe *S. aureus* infections outside foreign material: endocarditis, septicaemia, haematogenous osteoarticular infections (Söderquist et al, 1993, Staphylococcal a-toxin in septicaemic patients; detection in serum, antibody response and production in isolated strains, *Serodiagn Immunother Infect Dis* 5:139-144; Nordin et al, 1995, Antibody response in patients with osteomyelitis of the mandible, *Oral Surg Oral Med Oral Pathol Oral Radiol Endod* 79:429-435; Kanclerski et al, 1996, Serum antibody response to *Staphylococcus aureus* enterotoxins and TSST-1 in patients with septicaemia, J Med Microbiol 44:171-177; Colque-Navarro et al, 1998, Antibody response in *Staphylococcus aureus* septicemia—a prospective study. *J Med Microbiol* 47:217-225; Colque-Navarro & Möllby, 1999, Usefulness of staphylococcal serology. *J Med Microbiol* 48:107-109; Ellis et al, 2003, Role of staphylococcal enterotoxin A in a fatal case of endocarditis, *J Med Microbiol* 52:109-112).

Current tests are based on the identification of antibodies directed against antigens specific to *S. aureus* or those produced by *S. aureus*, for example anti-α-toxin antibodies (or alpha antistaphylolysins), anti-β-ribitol teichoic acid, anti-enterotoxins and anti-staphylococcal toxic shock syndrome toxin 1 (anti-TSST1), and anti-capsular antibodies. The antibodies are detected by haemolysis inhibition, by electrosyneresis or by ELISA (Bornstein et al, 1992, Immune response to staphylococcal toxins and ribitol teichoic acid in *Staphylococcus aureus* infections, *Med Microbiol Lett* 1:111-119; Christensson et al, 1993, Diagnosing *Staphylococcus aureus* endocarditis by detecting antibodies against *S. aureus* capsular polysaccharides types 5 and 8, *J Infect Dis* 163:530-533; Kanclerski et al, 1996 [already cited]). These tests are largely insensitive and nonspecific and give variable results depending on the strains involved, in particular depending on the toxins which they produce (for example, greater response for positive enterotoxin B and/or C strains than for positive enterotoxin A and/or TSST1 strains) (Kanclerski et al, 1996 [already cited]). Lastly, there are no tests for identifying the class of the antibodies produced, and in particular whether they are IgG or IgA antibodies.

Both *S. aureus* and *S. epidermidis* or other CNSs are commensal bacteria commonly found in humans (nasal membrane for *S. aureus* and skin for *S. epidermidis* and other CNSs) and identifying the antigens indicating infection is difficult. This difficulty has been confirmed by laboratory tests carried out by the applicant in which numerous staphylococcal antigens were not established as infection markers, the controls responding in the same proportions as the infected samples.

Diagnosis and Monitoring of Staphylococcal PJIs

It is vital to be able to diagnose a PJI with certainty. In fact, treatment of a PJI, which is involved and costly, is associated with a significant impact on joint function and involves serious risks. Generally, treatment consists of extensive and complicated surgical debridement together with long-term tailored antibiotherapy. The main surgical options are replacing the prosthesis in a one-stage process or debridement and retention of the prosthesis and re-implantation of the prosthesis in two stages, which requires longer periods of hospitalisation (Garvin and Hanssen, 1995, Current concepts review. Infection after total hip arthroplasty. Past, present, and future, *J Bone Joint Surg* 77-A:1576-1588). The mortality rate associated with surgical procedure for PJI ranges from 0.4 to 1.2% for patients aged 65 and from 2 to 7% for patients aged 80 (Lentino, Prosthetic joint infections: bane of orthopedists, challenge for infectious disease specialists, *Clin Infect Dis* 36:1157-1161).

The risk of failure by way of infection is greater after revision surgery on PJIs, rising on average from 10 to 40% depending on location, the severity of lesions and the type of surgical treatment. Failure is not always due to infection and, on the other hand, may involve another bacteria other than that which caused the first episode of PJI (associated bacteria not found in perioperative samples or bacteria inoculated accidentally during revision surgery).

A follow-up serological test makes it possible to give an early diagnosis of failure by identifying the nature of the infection and the bacteria involved.

In cases not involving acute or hyperacute PJIs, there are currently no tests which make it possible to make a reliable pre-operative diagnosis of PJI and, in particular, to differentiate a PJI from aseptic loosening, which is treated by simply exchanging the prosthesis in a one-stage process and which does not require any antibiotherapy. The clinical signs are misleading: pain and inflammation are not specific to infection and fever is usually absent. Simple radiography is insensitive and the abnormalities indicating the presence of an infection take too long to appear. Biological markers of inflammation, such as erythrocyte sedimentation rate (ESR) or C-reactive protein (CRP), are insensitive and nonspecific.

Nowadays, diagnosis of PJI can thus only be made with certainty by culturing perioperative samples or fluid aspirate, which involves a surgical procedure carried out under general anaesthetic (in some cases it is also possible to obtain true-cut-type samples without surgery but under general anaesthetic).

This method poses several drawbacks:

it is not currently possible to give a pre-operative diagnosis of PJI or even to establish which bacterium or bacteria are involved, the methods for culturing perioperative samples are not standardised and recent studies have shown that conventional methods lack sensitivity (Tunney et al, 1999. Detection of prosthetic hip infection at revision arthroplasty by immunofluorescence microscopy and PCR amplification of the bacterial 16S rRNA gene, *J Clin Microbiol* 37:3281-3290), the time required for culturing is particularly long in chronic cases, interpretation of the culture results remains controversial: the threshold of at least three independent positive samples suggested by the OSIRIS group, Oxford provides excellent specificity (Atkins et al, 1998 [already cited]), but may lack sensitivity, in particular when samples are prepared in sub-optimal conditions.

None of the current diagnostic methods uses purified antigens to indicate a staphylococcal infection on a joint prosthesis and current serological methods do not allow follow-up treatment or post-implantation diagnosis to be carried out.

In this field there is thus an extreme need for a serological diagnosis method in order to be able to carry out quick, cheap and non-invasive tests. Ideally, these tests will make it possible to identify the bacterium or bacteria involved and, in particular, will make it possible to distinguish *S. aureus*, which has a significant ability to destroy tissue, from other staphylococci.

Use of these tests may also make it possible to make an early diagnosis of PJI and thus enable better surgical management at an early stage of infection. This may be achieved by long-term serological monitoring, that is to say monitoring over a substantial period of time, of patients after prosthetic implantation (post-implantation diagnosis), in particular in patients having a higher risk of PJI.

Lastly, in the future, if vaccinal approaches have been developed to prevent staphylococcal PJIs, in particular but not exclusively, those caused by *S. aureus*, tests of this type will be vital for detecting vaccination failures.

The object of the present invention is to overcome the drawbacks presented by the absence of serological tests enabling a staphylococcal infection on foreign material, in particular on a joint prosthesis, to be isolated by detecting circulating antibodies.

Another object of the present invention is to enable the detection of circulating antibodies which are directed against bacteria which are found in a state of dormancy and are protected from the immune system by being present within a biofilm. A further object of the invention is to enable diagnosis of polymicrobial staphylococcal infections (that is to say those involving a plurality of different species).

An additional object of the invention is to enable a more accurate and more comprehensive analysis owing to the detection of different antibody isotopes specific to polypeptides.

DEFINITIONS

The following definitions are given so as to facilitate the understanding of specific terms used within the description.

"Polynucleotide" means a polyribonucleotide or a polydeoxyribonucleotide which may be modified or unmodified DNA or RNA.

The term polynucleotide includes, in an non-limiting manner, single strand or double strand DNA, DNA formed of a mixture of one or more single strand regions and of one or more double strand regions, DNA which is a mixture of single strand regions, double strand regions and/or triple strand regions, single strand or double strand RNA, RNA formed of a mixture of one or more single strand regions and of one or more double strand regions, and hybrid molecules comprising DNA and RNA which may include single strand regions, double strand regions and/or triple strand regions or a mixture of single strand and double strand regions. The term polynucleotide may also include RNA and/or DNA comprising one or more triple strand regions. Strands in these regions may originate from the same molecule or from different molecules. Consequently, DNA or RNA with a backbone modified for reasons of stability or otherwise are included in the term polynucleotides. Polynucleotide also means DNA and RNA containing one or more modified bases. Modified base means, for example, unusual bases such as inosine. The term polynucleotide also includes chemically, enzymatically or metabolically modified polynucleotides. Polynucleotides also include short polynucleotides, such as oligonucleotides.

"Polypeptide" means a peptide, an oligopeptide, an oligomer or a protein comprising at least two amino acids joined together by a normal or modified peptide bond.

The term polypeptide includes short chains, known as peptides, oligopeptides and oligomers, and long chains known as proteins.

A polypeptide may be formed of amino acids other than the 20 amino acids coded by human genes. A polypeptide may also be formed of amino acids modified by natural processes, such as by the post-translational maturation process or by chemical processes which are well known to the person skilled in the art. The same type of modification may be present at a plurality of locations on the polypeptide and anywhere within the polypeptide: in the peptide backbone, in the amino acid chain or even at the carboxy-terminal or amino-terminal ends.

A polypeptide may be branched following ubiquitination or cyclic with or without branching. These types of modification may be the result of a natural or synthetic post-translational process, these processes being well known to the person skilled in the art.

Modification of a polypeptide means, for example, acetylation, acylation, ADP-ribosylation, amidation, covalent binding of flavin, covalent binding of a heme, covalent binding of a nucleotide or of a nucleotide derivative, covalent binding of a lipid or of a lipid derivative, covalent binding of a phosphatidylinositol, covalent or non-covalent cross linking, cyclisation, formation of a disulphide bond, demethylation, the formation of cysteine, the formation of pyroglutamate, formylation, gamma-carboxylation, glycosylation, the formation of a GPI anchor, hydroxylation, iodisation, methylation, myristoylation, oxidation, the proteolytic process, phosphorylation, prenylation, racemisation, seneloylation, sulphation, amino acid addition such as arginylation or ubiquitination (PROTEINS STRUCTURE AND MOLECULAR PROPERTIES, $2^{nd}$ Ed., T. E. Creighton, W.H. Freeman and Company, New York (1993) and Wold, F., Posttranslational Protein Modifications: Perspectives and Prospects, pgs 1-12 in POSTTRANSLATIONAL COVALENT MODIFICATION OF PROTEINS, B. C. Johnson, Ed., Academic Press, New York (1983); Seifter et al., Meth. Enzymol. 182:626-646 (1990) and Rattan et al., Protein Synthesis: Posttranslational Modifications and Aging, Ann. N.Y. Acad. Sci. 663:48-62 (1992)).

"Percentage identity" between two polynucleotide or polypeptide sequences means the percentage of identical nucleotides or amino acids in the two sequences to be compared and is obtained after achieving the best alignment possible, this percentage being purely statistical and the differences between the two sequences being randomly distributed over their entire length. Comparisons between two polynucleotide or polypeptide sequences are conventionally carried out by comparing these sequences after having optimally aligned them, said comparison being carried out per segment or per "comparison window" in order to identify and compare the local regions with sequence similarity. This comparison may be carried out by means of a program, for example the EMBOSS-Needle program (Needleman-Wunsch global alignment) using the BLOSUM62 matrix/Gap opening penalty 10.0 and Gap extension penalty 0.5 (Needleman et Wunsch (1970), *J. Mol. Biol.* 48, 443-453 and Kruskal, J. B. (1983), An overview of sequence comparison, In D. Sankoff and J. B. Kruskal, (ed), Time warps, string edits and macromolecules: the theory and practice of sequence comparison, pp. 1-44 Addison Wesley).

The percentage identity is calculated by determining the number of identical positions for which the nucleotide or the amino acid is identical between the two sequences, by dividing this number of identical positions by the total number of positions within the comparison window and by multiplying the result by 100.

A polynucleotide having, for example, an identity of at least 95% with the polynucleotide of SEQ ID No. 1 is thus a polynucleotide comprising, at most, 5 modified nucleotides out of 100 nucleotides compared with said sequence. In other words, up to 5% of the nucleotides in the sequence of SEQ ID No. 1 can be deleted or substituted by another nucleotide, or up to 5% of the total number of nucleotides in the sequence of SEQ ID No. 1 may be inserted into said sequence. These modifications may be located at the 3' and/or 5' ends, or anywhere between these ends, at one or more locations.

Similarly, a polypeptide having an identity of at least 95% with the polypeptide of SEQ ID No. 2 is a polypeptide comprising, at most, 5 modified amino acids out of 100 amino acids compared with said sequence. In other words, up to 5% of the amino acids in the sequence of SEQ ID No. 2 can be deleted or substituted by another amino acid or up to 5% of the total number of amino acids in the sequence of SEQ ID No. 2 may be inserted into said sequence. These changes to the sequence may be located at the amino-terminal and/or carboxy-terminal positions of the amino acid sequence or anywhere between these terminal positions, at one or more locations. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987).

With regard to the term "similarity", this is calculated in the same way as identity except that amino acids which are not identical but which have common physico-chemical characteristics are considered to be identical.

"Host cell" means a cell which has been transformed or transfected, or is capable of being transformed or transfected, by an exogenous polynucleotide sequence.

"Culture medium" means the medium in which the polypeptide of the invention is purified. This medium may be formed by the extracellular medium and/or the cellular lysate. Methods which are well known to the person skilled in the art also make it possible restore the active conformation of the polypeptide if the conformation of said polypeptide was modified during isolation or purification.

"Function" means the biological activity of a polypeptide or of a polynucleotide.

The function of a polypeptide in accordance with the invention is that of a *Staphylococcus epidermidis* and/or *Staphylococcus aureus* and/or *Staphylococcus caprae* antigen, and the function of a polynucleotide in accordance with the invention is that of coding said polypeptide. The function of a combination of antigens is to make it possible to diagnose an infection on foreign material and, in particular, on an osteoarticular prosthesis, but also to carry out post-implantation follow-up checks, therapeutic follow-up checks and, lastly, to recognise whether an active or acute infection is involved, for example by detecting different antibody isotypes.

"Antigen" means any compound which, either alone or in combination with an adjuvant or carrier, is capable of inducing a specific immune response. This definition also includes any compound exhibiting structural similarity with said antigen capable of inducing an immunological response directed against said antigen.

"Structural similarity" means a similarity of both the primary structure (sequence) and of the secondary structure (structural elements), of the tertiary structure (three-dimensional structure) or of the quaternary structure (association of a plurality of polypeptides in a single complex) (BIOCHEMISTRY, 4$^{th}$ Ed, L. Stryer, New York, 1995).

A "variant" of what is known as an initial polynucleotide or of what is known as an initial polypeptide means, respectively, a polynucleotide or a polypeptide which differs therefrom by at least one nucleotide or one amino acid, but which maintains the same intrinsic properties, that is to say the same function.

A difference in the polynucleotide sequence of the variant may or may not alter the amino acid sequence of the polypeptide which it codes compared with an initial polypeptide. However, by definition, these variants must confer the same function as the initial polynucleotide sequence, for example code a polypeptide having an antigenic function.

The variant polynucleotide or variant polypeptide generally differs from the initial polynucleotide or initial polypeptide by one (or more) substitutions, additions, deletions, fusions or truncations or by a combination of a plurality of these modifications. An unnatural variant of an initial polynucleotide or of an initial polypeptide may be obtained, for example, by site-directed mutagenesis or by direct synthesis.

A "polynucleotide sequence complementary to the polynucleotide sequence" is defined as a polynucleotide which may be hybridised with said polynucleotide sequence under stringent conditions.

Generally, but not necessarily, "stringent conditions" means chemical conditions enabling hybridisation when the polynucleotide sequences have an identity of at least 80%.

These conditions may be obtained in accordance with methods which are well known to the person skilled in the art.

"Antibodies" means humanised, single-chain, chimeric monoclonal and polyclonal antibodies as well as Fab fragments, including products of Fab or immunoglobin expression library. It is also possible to use other immunospecific molecules in place of antibodies, for example T-cell receptors (TCRs) as recently described (Li et al, 2005, Directed evolution of human T-cell receptors with picomolar affinities by phage display, *Nat Biotechnol*, 23:349-54) or molecules selected for their specific binding ability, for example by directed evolution (see for example Conrad and Scheller. 2005. Considerations on antibody-phage display methodology, *Comb Chem High Throughput Screen*, 8:117-26).

An immunospecific antibody may be obtained by administering a given polypeptide to an animal followed by recovery of the antibodies produced by said animal by way of extraction from its bodily fluids. A variant of said polypeptide, or host cells expressing said polypeptide may also be administered to the animal.

The term "immunospecific" applied to the term antibody, in relation to a given polypeptide, means that the antibody has a greater affinity for this polypeptide than for other polypeptides known from the prior art.

"Positive" serum means a serum containing antibodies produced following an *S. epidermidis* or *S. aureus* infection on a joint prosthesis and identified by way of their binding to the polypeptides (antigens) of the invention.

"Sensitivity" means the proportion of infected patients diagnosed in accordance with the prior art and said to be positive by way of the diagnostic procedure according to the invention.

"Specificity" means the proportion of blood donors, tested as controls, who underwent the diagnostic procedure in accordance with the invention and who were said to be negative by way of the diagnostic procedure according to the invention.

The present invention achieves the objects detailed above by providing novel polynucleotides and novel polypeptides as well as fragments which have proven to be more relevant and/or more sensitive and/or more specific than the entire protein.

The invention relates to the in vitro use of at least one of the proteins of the sequence of SEQ ID No. 2, 4, 6, 8, 10, 12, 14, 16, 18, 20, 22, 24, 26, 28, 30, 32, 34 or 36, of part or variants of said protein, of host cells comprising vectors including a polynucleotide coding at least one of said proteins or a variant of said proteins, in the production of antibodies and within the field of in vitro diagnosis of *Staphylococcus epidermidis* and/or *S. aureus*. The invention also relates to a diagnostic kit and a pharmaceutical composition.

Use of Polypeptides

The applicant's laboratory is aware of polypeptides produced by *S. epidermidis* or *S. aureus* which do not allow prognosis of an infection on foreign material, in particular on a joint prosthesis (for example *S. epidermidis* recombinant protein "Thimet oligopeptidase-like protein" (Q8CPS6).

However, the applicant unexpectedly found that a prognosis of this type is in fact possible by using other polypeptides produced by *S. epidermidis* or *S. aureus* specifically identified by the applicant, and even by using polypeptide fragments produced by *S. epidermidis* or *S. aureus* which, when complete, do not allow this prognosis.

The identification of the polypeptides according to the invention is the result of close examination and in-depth studies and was not possible using the sequences produced by the genome research programmes into *S. epidermidis* or *S. aureus*.

The present invention thus relates to the use, in the production of antibodies and within the field of in vitro diagnosis of *Staphylococcus epidermidis* and/or *S. aureus* infections, of at least one polypeptide comprising:

amino acid sequence of SEQ ID No. 2 (known as protein E4), coded by polynucleotide sequence of SEQ ID No. 1; or amino acid sequence of SEQ ID No. 4 (known as protein 2B6), coded by polynucleotide sequence of SEQ ID No. 3; or amino acid sequence of SEQ ID No. 6 (known as protein F2), coded by polynucleotide sequence of SEQ ID No. 5; or amino acid sequence of SEQ ID No. 8 (known as protein 3F7), coded by polynucleotide sequence of SEQ ID No. 7; or amino acid sequence of SEQ ID No. 10 (known as protein 2D6B1), coded by polynucleotide sequence of SEQ ID No. 9; or amino acid sequence of SEQ ID No. 12 (known as protein JR7), coded by polynucleotide sequence of SEQ ID No. 11; or amino acid sequence of SEQ ID No. 14 (known as protein JR12), coded by polynucleotide sequence of SEQ ID No. 13; or amino acid sequence of SEQ ID No. 16 (known as protein JR5), coded by polynucleotide sequence of SEQ ID No. 15; or amino acid sequence of SEQ ID No. 18 (known as protein 3A7), coded by polynucleotide sequence of SEQ ID No. 17; or amino acid sequence of SEQ ID No. 20 (known as protein 3B6), coded by polynucleotide sequence of SEQ ID No. 19; or amino acid sequence of SEQ ID No. 22 (known as protein 3D5), coded by polynucleotide sequence of SEQ ID No. 21; or amino acid sequence of SEQ ID No. 24 (known as protein 3E5), coded by polynucleotide sequence of SEQ ID No. 23; or amino acid sequence of SEQ ID No. 26 (known as protein 3F3), coded by polynucleotide sequence of SEQ ID No. 25; or amino acid sequence of SEQ ID No. 28 (known as protein 3G3), coded by polynucleotide sequence of SEQ ID No. 27; or amino acid sequence of SEQ ID No. 30 (known as protein 3H3), coded by polynucleotide sequence of SEQ ID No. 29; or amino acid sequence of SEQ ID No. 32 (known as protein 3H4), coded by polynucleotide sequence of SEQ ID No. 31; or amino acid sequence of SEQ ID No. 34 (known as protein 3D7), coded by polynucleotide sequence of SEQ ID No. 33; or amino acid sequence of SEQ ID No. 36 (known as protein 3C7), coded by polynucleotide sequence of SEQ ID No. 35.

The present invention also relates to the use of at least one polypeptide comprising:

a) part of the amino acid sequence of SEQ ID No. 2, 4, 6, 8, 10, 12, 14, 16, 18, 20, 22, 24, 26, 28, 30, 32, 34 or 36 having the same function as said sequence, or b) an amino acid sequence having at least 60% identity, preferably at least 80% identity and most preferably at least 90% identity with one of the amino acid sequences of SEQ ID No. 2, 4, 6, 8, 10, 12, 14, 16, 18, 20, 22, 24, 26, 28, 30, 32, 34 or 36 or with part of the sequence defined under a), and having the same function as said sequence.

The polypeptides in accordance with the invention may thus comprise variants of amino acid sequences of SEQ ID No. 2, 4, 6, 8, 10, 12, 14, 16, 18, 20, 22, 24, 26, 28, 30, 32, 34 or 36.

The polypeptide sequence of SEQ ID No. 4, known as protein 2B6, coded by the sequence of SEQ ID No. 3, comprises amino acids 1 to 184 of the sequence of SEQ ID No. 2 and has the same function as the sequence of SEQ ID No. 2.

The polypeptide sequence of SEQ ID No. 6 (known as protein F2), coded by the polynucleotide sequence of SEQ ID No. 5, has 60% identity and 78% similarity with the sequence of SEQ ID No. 2.

Other variants of the sequences of SEQ ID Nos. 2, 4, and 6 are, for example, part of the AtlC protein (3F7 (SEQ ID No. 8) for example) coded by the bacterium *Staphylococcus caprae*.

Owing to the polypeptides defined above, the invention enables detection of antibodies which are produced naturally during staphylococcal infections on joint prostheses.

The invention further relates to the use of polypeptides according to the invention to periodically detect, in vitro, antibodies directed against *S. epidermidis* and/or *S. aureus* and thus to monitor the progression of the pathology and the effect of treatment given to a patient.

The biological samples tested may be samples of blood, urine, saliva, fluid obtained via serological puncture (for example cerebrospinal fluid, pleural fluid or joint fluid) or of one of their constituents (for example serum).

A *Staphylococcus epidermidis* and/or *S. aureus* infection is diagnosed in vitro, for example using conventional tests for testing immunological reactions, such as ELISA or Western Blot tests. These tests use one of the polypeptides according to the invention which bonds, specifically, to any serum antibodies directed against *Staphylococcus epidermidis* and/or *S. aureus* present in the biological samples.

Use of Expression Vectors and Host Cells

The present invention also relates to the use of a polypeptide prepared by culturing a host cell comprising a recombinant vector having, inserted, a polynucleotide coding said polypeptide.

Numerous expression systems may be used, such as chromosomes, episomes and derived viruses. More particularly, the recombinant vectors used may be derived from bacterial plasmids, transposons, yeast episomes, insertion elements, chromosomal elements of yeasts, viruses such as baculoviruses, papillonna viruses such as SV40, vaccinia viruses, adenovirusus, fox pox viruses, pseudorabies viruses, and retroviruses.

These recombinant vectors may also be derivatives of cosmids or phagemids. The polynucleotide sequence may be inserted into the recombinant expression vector by methods well known to the person skilled in the art.

The recombinant vector may comprise polynucleotide sequences for monitoring the regulation of the polynucleotide expression as well as polynucleotide sequences enabling expression and transcription of a polynucleotide according to the invention and translation of a polypeptide according to the invention, these sequences being selected as a function of the host cells used.

The introduction of the recombinant vector into a host cell may be carried out in accordance with methods which are well known to the person skilled in the art, such as transfection by calcium phosphate, transfection by cationic lipids, electroporation, transduction or infection.

The host cells may be, for example, bacterial cells, such as streptococcal cells, staphylococcal cells, *Escherichia coli* or *Bacillus subtilis* cells; fungus cells, such as yeast cells and *Aspergillus* cells; *Streptomyces* cells; insect cells, such as *Drosophilia* S2 and *spodoptera* Sf9 cells; animal cells, such as CHO, COS, HeLa, C127, BHK, HEK 293 cells or even vegetable cells.

The polypeptide may be purified from host cells in accordance with methods which are well known to the person skilled in the art, such as precipitation using chaotropic agents, such as salts, in particular ammonium sulphate, ethanol, acetone or tricholoroacetic acid, or by means such as acid extraction, ion exchange chromatography, phosphocellulose chromatography, hydrophobic interaction chromatography, affinity chromatography, hydroxylapatite chromatography or exclusion chromatography.

Use of Polynucleotides

The present invention also relates to the use, in the production of antibodies and in the diagnosis of a *Staphylococcus epidermidis* and/or aureus infection, of at least one polynucleotide comprising the polynucleotide sequence of SEQ ID No. 1, 3, 5, 7, 9, 11, 13, 15, 17, 19, 21, 23, 25, 27, 29, 31, 33 or 35, coding, respectively, protein 2, 4, 6, 8, 10, 12, 14, 16, 18, 20, 22, 24, 26, 28, 30, 32, 34 or 36.

The invention also relates to the use of at least one polynucleotide comprising:

a) part of the sequence of SEQ ID No. 1, 3, 5, 7, 9, 11, 13, 15, 17, 19, 21, 23, 25, 27, 29, 31, 33 or 35, and having the same function as said sequence, or b) a polynucleotide sequence having at least 60% identity, preferably at least 80% identity, and most preferably at least 90% identity with the polynucleotide sequence of SEQ ID No. 1, 3, 5, 7, 9, 11, 13, 15, 17, 19, 21, 23, 25, 27, 29, 31, 33 or 35 or with the sequence part as defined under a), and having the same function as said sequence, or c) a polynucleotide sequence complementary to the polynucleotide sequence of SEQ ID No. 1, 3, 5, 7, 9, 11, 13, 15, 17, 19, 21, 23, 25, 27, 29, 31, 33 or 35 or to the sequence part defined under a) or to the sequence defined under b).

The polynucleotide sequence of SEQ ID No. 3 comprises nucleotides 1 to 552 of the sequence of SEQ ID No. 1 and has the same function as said sequence.

The polynucleotide sequence of SEQ ID No. 5 (known as F2 and extracted from the *Staphylococcus aureus* genome) is a variant of the sequence of SEQ ID No. 1.

Other variants are, for example, polynucleotide sequences coding proteins of the autolysin family (for example the sequence of SEQ ID No. 7, a variant of the sequence of SEQ ID No. 1 coding part of the AtlC protein, known as 3F7 and present in the *Staphylococcus caprae* bacterium). The polynucleotides according to the invention may thus comprise variants of one of the polynucleotide sequences of SEQ ID No. 1, 3, 5, 7, 9, 11, 13, 15, 17, 19, 21, 23, 25, 27, 29, 31, 33 or 35.

The polynucleotides of the invention may be obtained by standard DNA or RNA synthesis methods.

The polynucleotides according to the invention may also comprise polynucleotide sequences, such as the non-coding 5' and/or 3' sequences, for example transcript sequences, untranslated sequences, splicing signal sequences, polyadenylated sequences, ribosome-binding sequences or even RNAm stabilising sequences.

Use of the Antibodies According to the Invention

The invention also relates to the use of antibodies, according to the invention, for in vitro detection in biological samples of the presence of *S. epidermidis* and/or *S. aureus* antigens.

The invention further relates to the use of antibodies according to the invention to periodically detect, in vitro, *S. epidermidis* and/or *S. aureus* antigens and thus to monitor the progression of the pathology and the effect of treatment given to a patient.

Immunospecific antibodies may be obtained by administering a polypeptide according to the invention, one of its fragments, an analogue or an epitopic fragment, or a cell expressing said polypeptide to a preferably non-human mammal, in accordance with methods well known to the person skilled in the art.

In order to prepare monoclonal antibodies, conventional methods for producing antibodies from cellular lines, such as the hybridomal method, the trioma method, the human B cell hybridomal method and the EBV hybridomal method may be used.

Antibody Isotopes and Affinity

Immunoglobulins (or antibodies) are formed of two different polypeptide chains: two light chains (L) of [kappa] or [lambda] isotopes, and two heavy chains (H) of [gamma], [alpha], [mu], [delta] or [epsilon] isotopes. These four chains are covalently bonded by disulphide bonds. The two chain types H or L have regions which contribute to the binding of antigens and may vary greatly from one immunoglobulin to another. These regions determine the affinity of the antibodies for their ligand.

Heavy chain isotopes make it possible to define the class of the immunoglobulin. There are thus five antibody isotopes (IgA, IgM, IgD, IgE and IgG). Sub-classes, for example IgG1, IgG2, IgG3 and IgG4 are defined by the differences in the heavy chain sequence. The different classes of immunoglobulins have their own physico-chemical properties and their synthesis depends directly on the phases and activation levels of the immune response.

In humans, the IgGs are the main class of immunoglobulins: their serum concentration in adults varies from 8 to 16 g/l. Their plasma half-life is approximately three weeks.

IgAs are the second most common class of serum immunoglobulins after IgGs in terms of concentration (2 to 4 g/l). In contrast, they are the predominant class of immunoglobulins in secretions (respiratory, salivary, digestive secretions, etc, milk, colostrum, tears). With regard to structure, IgAs are distinct by existing in a plurality of molecular forms:

in serum, IgAs may be present in the form of monomers (predominant form) or in the form of dimers associated with a J chain (junction chain). The J chain is a cysteine-rich peptide of 137 amino acids (molecular weight: 15,000 Da), of plasmocyte origin; sub-class IgA1 is predominant in serum.

in secretions, IgAs, known as secretory IgAs, are in the form of dimers: they are thus associated with a J chain but they also comprise a secretory component. IgAs produced by B lymphocytes are captured by epithelial cells by a receptor (polyIgR) arranged at the basal pole of the cell. It is during the transfer of IgA through the epithelial cell towards the apical pole of the cell that the secretory component (molecular weight: 70,000 Da) or secretory piece is added. The role of the secretory piece is to protect the secretory IgAs from proteolytic enzymes present in the secretions.

Similarly to IgAs, IgMs may exist in two distinct molecular forms:

a monomeric form: this is the form in which IgMs are synthesised and inserted into the membrane of B lymphocytes;

a pentameric form: this is the form in which IgMs are secreted. The five base monomers are connected by disulphide bonds. Furthermore, a J chain connects the ends of two monomers.

IgDs account for less than 1% of serum immunoglobulins. They are usually coexpressed with IgMs at the surface of B lymphocytes where they appear to play the role of antigen receptors.

In a normal subject IgEs are only present in trace form.

Kinetics of Appearance of Antibodies and Affinity

The kinetics of appearance of specific antibodies and of a given isotype is still not understood well. Generally, B cells known as naïve B cells synthesise different IgMs which constitute a large source of molecules able to bind antigens (Steven A. Frank, Immunology and Evolution of Infectious Disease, (2002), Princeton University Press, Princeton, USA). When first exposed to an antigen, said antigen thus binds with a weak affinity to different IgMs of the immune system. However, this interaction stimulates division of the corresponding naïve B cell. The rapidity of division increases with the strength of the affinity of the IgM which enables an initial selection of the best clones. Furthermore, during division genetic rearrangements allow the affinity of the antibodies to increase. The constant region of the immunoglobulins also changes so as to produce IgGs in the circulatory system and IgAs at mucous surfaces (Steven et Frank 2002, Immunology and Evolution of Infectious Disease, Princeton University Press, Princeton, USA).

The person skilled in the art may thus deduce that the presence of one or more antibody classes and the specific affinity of the antibodies have different implications from a medical diagnostic point of view when differentiating, in the case of recurrent or non-recurrent infections, between an active, acute, chronic, latent and recent infection.

Kits

The invention also relates to in vitro diagnostic kits comprising at least one of the polypeptides according to the invention, or at least one of the polynucleotides coding said polypeptides, as well as in vitro diagnostic kits comprising at least one of the antibodies according to the invention.

Vaccines

The present invention also relates to a pharmaceutical composition which can be used as a vaccine and contains, as an active ingredient, at least one polypeptide according to the invention or a polynucleotide or a recombinant vector or a host cell according to the invention.

EXPERIMENTAL PART

A) Protocols for Producing Antigens

A.1. Cloning of the Sequence Coding Polypeptides of SEQ ID No. 2, 4, 6, 8, 10, 12, 14, 16, 18, 20, 22, 24, 26, 28, 30, 32, 34 or 36

Genes coding polypeptide sequences, which are antigens, are obtained by PCR amplification from the genomic DNA of *Staphylococcus epidermidis* (WHO 12 strain, ATCC 12228), *Staphylococcus caprae* (ATCC 35538) or *Staphylococcus aureus* (MU50 strain, ATCC 700699 or MW2) bacteria by using, respectively, specific primers of the sequences of SEQ ID No. 1, 3, 5, 7, 9, 11, 13, 15, 17, 19, 21, 23, 25, 27, 29, 31, 33 or 35. Specific primers means short nucleotide sequences capable of hybridisation in a specific manner, owing to the base-pairing rule, on the DNA strand or on its complementary strand, these primers being selected by the person skilled in the art so as to include the DNA sequence and to amplify it specifically (for example SEQ ID No. 1, 3, 5, 7, 9, 11, 13, 15, 17, 19, 21, 23, 25, 27, 29, 31, 33 or 35).

The corresponding fragment thus amplified is cloned into a vector in accordance with conventional methods well known to the person skilled in the art. This vector allows the production of cloned proteins under the control of an isopropyl thiogalactoside (IPTG) inducible promoter. The cloned proteins correspond to the polypeptides of SEQ ID No. 2, 4, 6, 8, 10, 12, 14, 16, 18, 20, 22, 24, 26, 28, 30, 32, 34 or 36.

A.2. Expression of Proteins

An *Escherichia coli* strain is transformed by the aforementioned expression vectors. The selected bacteria are cultured overnight at 30° C., with stirring, in 30 ml of Luria Bertani medium (LB, J. Miller, "A short Course in Bacterial Genetics", Cold Spring Harbor Laboratory Press, 1992) containing ampicillin at a final concentration of 100 µg/ml. The next day, the culture is diluted at a ratio of 1:50 in a final volume of 1 liter of LB medium supplemented with ampicillin at a final concentration of 100 µg/ml and incubated at 30° C. with stirring. When the turbidity of the culture reaches an absorbance value at 600 nm (A600) of approximately 0.7, the production of the protein is induced by isopropyl thiogalactoside (IPTG) at a final concentration of 0.1 mM. The bacteria are harvested by centrifugation (10 minutes at 1400×g and at 4° C.) when the turbidity of the culture reaches an A600 of approximately 1.5.

A.3. Purification of Proteins

After centrifugation, the cells are resuspended in a 20 mM Tris-HCl buffer at pH 8.0 containing sucrose at 0.5 mM, then treated with lysozyme (0.2 g/l) in the presence of 12.5 mM of ethylenediaminetetraacetic acid (EDTA), DNase, RNase and PMSF. The suspension is incubated for 30 minutes at 4° C. and then centrifuged for 10 minutes at 4° C. at 15,500×g. The pellet is frozen at −20° C. for at least one night.

A.4. Example

Purification of 3C7 (SEQ ID No. 36)

After thawing, the bacteria are placed in a Mes 25 mM buffer at pH 6.0, then sonicated for 20 seconds in ice, four times. After centrifugation at 15,500×g at 4° C. for 30 minutes, the supernatant is filtered on a membrane with a porosity of 0.22 µm. The filtrate is then deposited on a cation-exchange column (for example 12 ml SP-SEPHAROSE®, Amersham Biosciences). After washing the column, the protein is eluted with a linear gradient of 0 to 1 M of NaCl in Mes 25 mM buffer at pH 6.0 in 20 column volumes. The fractions containing the protein are combined and the proteins are precipitated by ammonium sulphate at a final concentration of 0.6 g/l. The solution is left for at least one night at 4° C. and then centrifuged for 30 minutes at 20,800×g. The pellet is then taken up in the smallest volume possible (generally 300 µl of 50 mM $Na_2HPO_4/NaH_2PO_4$ buffer at pH 8.0 containing 100 mM NaCl and then deposited on a gel filtration column, for example SUPERDEX® HR75—10/30, Amersham). The eluted fractions containing the protein are combined and glycerol is added until a final concentration of 20% is obtained. The purified proteins are then stored at −20° C. until they are used in the tests.

The concentrations of the proteins are determined spectrophotometrically from the absorption coefficients calculated using the Pace method (Pace et al, 1995, How to measure and predict the molar absorption coefficient of a protein, *Protein Science* 4, 2411-2423). The purity of the proteins is checked by SDS-PAGE electrophoresis analysis and by mass spectrometry.

B) In vitro Diagnostic Test

Sera obtained from patients having had a documented osteoarticular infection (laboratory collection) caused by:

*Staphylococcus epidermidis* (at least three positive perioperative samples);

*Staphylococcus aureus* (at least one positive perioperative sample);

bacteria other than staphylococci (at least three positive perioperative samples) were used.

The control sera were sera obtained from blood donors (laboratory collection).

Example B1

Protocol of the Test for Polypeptides of SEQ ID Nos 2, 4, 6, 8, 10, 12, 14, 16, 18, 20, 22, 24, 26, 28, 30, 32 and 34 (ELISA)

The binding of the antibodies present in the sera was assessed using ELISA tests. The ELISA plates were left overnight at 4° C. in the presence of 0.5 µg of purified antigen (recombinant protein E4) in a phosphate buffered saline (PBS). After four washes with PBS containing 0.05% polyoxyethylene sorbitan (TWEEN®), the plates were saturated for one hour at 37° C. in PBS-TWEEN containing 5% semi-skimmed milk (250 µl per well). Four new washes were carried out and then 100 µl of each positive serum, at the appropriate dilution ratio (i.e. 1:3000 for E4) in PBS-TWEEN buffer containing 5% semi-skimmed milk, were added to each well. The plate was then left at 25° C. for 30 minutes. After four new washes, goat anti-human immunoglobulin G, M, or A (secondary) antibodies or, simultaneoulsy, goat anti-human immunoglobulin G and/or A and/or M (secondary) antibodies labelled with alkaline phosphatase (for example 170-6462, Biorad) were added for 30 minutes at 25° C. after having been diluted in accordance with the supplier's protocol in PBS-TWEEN buffer containing 5% semi-skimmed milk. Four new washes were carried out and then 100 µl of pNPP (p-nitrophenyl phosphate) substrate, for example A-3469, Sigma were added. The absorbance at 405 nm of each of the wells was measured after incubation for 30 minutes at 37° C.

Results and Interpretation

The tests were carried out on recombinant proteins obtained from independent purifications.

Typical results are shown in Table 1 (results according to the invention for polypeptides E4, F2 and 2D6-B1 with secondary antibodies recognising the total immunoglobulins (Ig G, A, and M) present in the patient sera).

TABLE 1 results (ELISA) obtained using anti-IgGAM antibodies as secondary antibodies

| | Polypeptide tested | | |
|---|---|---|---|
| | E4 | F2 | 2D6B1 |
| Percentage of "positive" sera from the 15 sera of patients infected with *S. epidermidis* diagnosed according to the prior art and who underwent the diagnostic procedure according to the present invention | 47.0% | 50.0% | 40.0% |
| Percentage of "positive" sera from the 16 sera of patients infected with *S. aureus* diagnosed according to the prior art and who underwent the diagnostic procedure according to the present invention | 26.0% | 25.0% | 25.0% |
| Percentage of "negative" sera from the 96 blood donor sera tested as controls | 95.0% | 98.0% | 96.8% |

It can be seen from Table 1 that the polypeptides of the invention may be used to isolate staphylococcal infections on joint prostheses.

Example B2

Results Obtained by Detecting of Antibody Isotypes in Sera (ELISA)

The use of some polypeptides, for example 2D6-B1 (Table 2) to detect immunoglobulins of a specific isotype is of particular relevance.

TABLE 2

Examples of results (ELISA) using anti-IgA antibodies as secondary antibodies

| Polypeptide tested | 2D6B1 |
|---|---|
| Percentage of "positive" sera from the 15 sera of patients infected with *S. epidermidis* diagnosed according to the prior art and who underwent the diagnostic procedure according to the present invention | 47.0% |
| Percentage of "positive" sera from the 16 sera of patients infected with *S. aureus* diagnosed according to the prior art and who underwent the diagnostic procedure according to the present invention | 31.0% |
| Percentage of "negative" sera from the 96 blood donor sera tested as controls | 97.0% |

It follows that the polypeptides may be used to indicate the presence of some antibody isotypes in the case of staphylococcal infections on joint prostheses.

Example B3

Combination of Polypeptides for in vitro Diagnosis of PJI

The combined use of a plurality of antigens and/or the detection of a plurality of antibody isotypes makes it possible to increase the sensitivity of the method (Tables 3 and 4).

Polypeptide 2B6 is very specific to *S. epidermidis* infections. In contrast with 2B6, polypeptide 2D6-B1 is not specific to a particular species and "positive" results may be observed with sera from patients having a PJI caused by other species of *Staphylococcus* (for example *S. lugdunensis*). This polypeptide is therefore "specific" to the staphylococcus genus and not to a specific species. It is thus possible, by using different polypeptides (or by detecting different antibody isotypes), to differentiate between species.

TABLE 3

Results (ELISA) obtained using combinations of different polypeptides according to the invention to detect immunoglobulins IgG, A or M

| Polypeptide tested | 2B6 | 2D6B1 | 2B6 or 2D6B1 |
|---|---|---|---|
| Percentage of "positive" sera from the 15 sera of patients infected with *S. epidermidis* diagnosed according to the prior art and who underwent the diagnostic procedure according to the present invention | 67.0% | 40.0% | 87.0% |
| Percentage of "positive" sera from the 16 sera of patients infected with *S. aureus* diagnosed according to the prior art and who underwent the diagnostic procedure according to the present invention | 11.0% | 25.0% | 37.5% |
| Percentage of "negative" sera from the 96 blood donor sera tested as controls | 99.0% | 96.8% | 96.0% |

TABLE 4

Results (ELISA) obtained by using 2D6B1 as a polypeptide and by detecting antibodies using different secondary antibodies

| Secondary antibodies used | IgA | IgG | IgG or A |
|---|---|---|---|
| Percentage of "positive" sera from the 15 sera of patients infected with *S. epidermidis* diagnosed according to the prior art and who underwent the diagnostic procedure according to the present invention | 47.0% | 40.0% | 67.0% |
| Percentage of "positive" sera from the 16 sera of patients infected with *S. aureus* diagnosed according to the prior art and who underwent the diagnostic procedure according to the present invention | 31.0% | 25.0% | 37.0% |
| Percentage of "negative" sera from the 96 blood donor sera tested as controls | 97.0% | 96.0% | 96.0% |

Example B4

Identification of PJIs Not Diagnosed by Culturing Perioperative Samples

These tests were carried out using sera from patients who underwent surgery for a suspected staphylococcal infection on a joint prosthesis, but who were considered, from a bacteriological point of view, to be uninfected in accordance with results following culture of deep perioperative samples obtained during revision surgery on the prosthesis (only one or two perioperative samples positive for CNS).

Table 5 shows an example of typical results obtained by detecting the total anti-2D6B1 immunoglobulins in 7 patients having had one or two perioperative samples which were positive for *S. epidermidis*. (laboratory collection). The control sera were sera obtained from blood donors (laboratory collection).

TABLE 5

|  | Type of prosthesis | ELISA value |
|---|---|---|
| Patient 1 | TKP | 2.026 |
| Patient 2 | THP | 0.151 |
| Patient 3 | TKP | 0.302 |
| Patient 4 | THP | 0.970 |
| Patient 5 | TKP | 2.237 |
| Patient 6 | THP | 0.369 |
| Patient 7 | THP | 0.465 |

During the same analysis, 3 of the 89 control sera (blood donors) had an ELISA value$\geq$0.900 (threshold indicating a specificity of 96.6%) and none had an ELISA value$\geq$1.600 (threshold indicating a specificity of 100.0%). The observed response was thus significant in patient 4 and highly significant in patients 1 and 5.

It is has thus been proven that it is possible to detect a significant antibody response to the polypeptides according to the invention in the case of osteoarticular infections on prostheses which have not been diagnosed by culturing perioperative samples.

Example B5

Protocol of the Test for Polypeptides of SEQ ID Nos. 12, 14 and 16 (Western Blot)

For the Western Blot tests, sera obtained from patients having had a documented *S. aureus* or *S. epidermidis* infection (laboratory collection) were used.

The control sera were sera obtained from blood donors (laboratory collection) and from patients carrying other infections (laboratory collection). Any possible binding of the antibodies present in these sera was assessed using Western Blot tests on total extracts of bacteria producing polypeptides of SEQ ID Nos 12, 14 and 16.

The nitrocellulose membrane onto which the proteins of the extract were transferred was saturated for 30 minutes using a phosphate buffered saline (PBS) solution containing 3% semi-skimmed milk. After three washes with PBS containing 0.05% polyoxyethyelene sorbitan (TWEEN®), the membrane was exposed to the test serum at the appropriate dilution ratio (i.e. 1:300) in PBS buffer containing 3% semi-skimmed milk, for 45 minutes. After three new washes, goat anti-human immunoglobulin G, M or A (secondary) antibodies or, simultaneously, goat anti-human immunoglobulin G and/or A and/or M (secondary) antibodies labelled with alkaline phosphatase (for example 170-6462, Biorad) were added for 30 minutes after having been diluted according to the supplier's protocol in PBS buffer containing 3% semi-skimmed milk. Three new washes were carried out and then 5-bromo-4-chloro-3-indolyl phosphate and nitroblue tetrazolium were added according to the supplier's instructions until the result was obtained. A "positive" result corresponds to precipitation of the substrate on the membrane at the position of the polypeptides of SEQ ID Nos 12, 14 or 16.

The results of these tests prove the existence of a significant antibody response in the case of osteoarticular infections on foreign material to polypeptides of SEQ ID Nos 12, 14 or 16 and the relevance of these polypeptides and of their associations/combinations for serological diagnosis of this type of infection. In fact, the combination of polypeptides of SEQ ID Nos 12, 14 or 16 is also relevant.

Similar results were obtained for all the polypeptides according to the invention (polypeptides of SEQ ID Nos 2, 4, 6, 8, 10, 12, 14, 16, 18, 20, 22, 24, 26, 28, 30, 32 and 34).

It has thus been proven, on the one hand, that there is a significant antibody response (IgG and/or IgA) in the case of osteoarticular infections on foreign material and, on the other hand, that the polypeptides according to the invention and their associations/combinations are relevant for the serological diagnosis of this type of infection. In fact, the combination of at least two polypeptides of SEQ ID Nos 2, 4, 6, 8, 10, 12, 14, 16, 18, 20, 22, 24, 26, 28, 30, 32 and 34 is also relevant. Furthermore, the combination of the results obtained by detection of different antibody isotypes in sera, for each of the polypeptides, is also relevant.

C) Use of the Polypeptides According to the Invention for Therapeutic Follow-Up Checks (Table 6)

For patients in convalescence, the observance of a decrease over time in the ELISA values, obtained by detecting the immunoglobulins (antibodies) present in the sera by way of their binding to antigens 2B6 or 2D6-B1 according to the invention, demonstrates that they are recovering well.

TABLE 6

| Progression as a function of the secondary antibody used ELISA value | | |
|---|---|---|
| | 2D6B1 | 2B6 |
| Patient 1 | | |
| anti-IgGAM | 0.99 | 2.3 (+) |
| anti-IgG | 0.4 | 0.51 (+) |
| anti-IgA | 0.66 | 0.34 |
| Patient 1 + 1 year | | |
| anti-IgGAM | 0.44 | 0.74 |
| anti-IgG | 0.27 | 0.24 |
| anti-IgA | 0.31 | 0.31 |
| Patient 2 | | |
| anti-IgGAM | 1.03 | 1.43 (+) |
| anti-IgG | 0.5 | 0.46 (+) |
| anti-IgA | 1.6 (+) | 0.2 |
| Patient 2 + 3 months | | |
| anti-IgGAM | 0.44 | 0.74 |
| anti-IgG | 0.27 | 0.24 |
| anti-IgA | 0.31 | 0.31 |
| Patient 3 | | |
| anti-IgGAM | 2.27 (+) | 1.6 (+) |
| anti-IgG | 0.94 (+) | 0.5 (+) |
| anti-IgA | 0.14 | 0.19 |
| Patient 3 + 6 months | | |
| anti-IgGAM | 2.41 (+) | 0.86 |
| anti-IgG | 0.87 (+) | 0.22 |
| anti-IgA | 0.15 | 0.19 |

The ELISA values marked (+) are considered to be positive

In Table 6, the individuals who were initially positive according to the invention have become negative.

Use of the polypeptides according to the invention thus makes it possible to carry out therapeutic follow-up checks, i.e. (i) to assess the effect of treatment and (ii) to monitor the post-operative (or post-implantation) progression of a patient.

D) Optimisation of Antigens and in vitro Diagnostic Tests

The study of fragments in order to improve, antigen performance on the one hand, and polypeptide production on the other is particularly useful for industrial use thereof and for the relevance of the tests.

Example D1

Increase in Sensitivity and Specificity

Table 7 shows the performances of 2B6, which is a fragment of E4, relative to the polypeptide E4.

TABLE 7

| Optimisation of the sensitivity and specificity of E4, 2B6; ELISA results using an IgGAM secondary antibody | | |
|---|---|---|
| Polypeptide tested | E4 | 2B6 |
| Percentage of "positive" sera from the 15 sera of patients infected with *S. epidermidis* diagnosed according to the prior art and who underwent the diagnostic procedure according to the invention | 47.0% | 67.0% |
| Percentage of "negative" sera from the 96 blood donor sera tested as controls | 95.0% | 99.0% |

There is a substantial difference depending on the polypeptide fragments used. This difference was not foreseeable based on the sequences. The sensitivity and specificity of 2B6 (fragment of E4) are thus greater than the entire protein or E4 (Table 7).

The use of antigen 2B6 to detect (total) immunoglobulins A, G and M makes it possible to identify 67% of PJIs caused by *S. epidermidis* (10 out of the 15 test sera) with 99% specificity (1 in 96 test blood donor sera).

Example D2

Increase in Stability and Production Levels

Furthermore, protein 2B6 does not deteriorate during its production in the host cell or during its purification.

E) Mulitparametric Combination and Evaluation by Syndrome

The combined use of a plurality of polypeptides according to the invention also makes it possible:
(i) to increase the sensitivity of detection;
(ii) to assess the likelihood of the presence of a plurality of bacteria (for example by using an antigen which is specific to a bacteria or to a family of bacteria);
(iii) to identify the genotype of the strain;
(iv) to determine progression of the pathology (by using specific antigens and antibody isotypes);
(v) to carry out therapeutic follow-up checks at reduced cost; and
(vi) to carry out diagnosis per syndrome In conclusion, the present invention discloses polypeptides having optimum sensitivity and specificity, enabling them to be used as a probe (antigen probe) in tests. The present invention makes it possible, without the need for surgery, to diagnose staphylococcal infections on foreign material, such as osteoarticular prostheses, in particular infections which have not been diagnosed by culturing deep perioperatve samples.

The invention claimed is:

1. An in vitro diagnostic method for determining if an individual is infected by bacteria of the *Staphylococcus* genus, comprising:
   contacting a biological sample of the individual with a purified protein consisting of SEQ ID NO: 10,
   measuring the amount of antibodies present in the biological sample that are bound to said protein, and
   determining whether or not the individual is infected by said *Staphylococcus* bacteria based upon the measured amount.

2. The method of claim 1, wherein the biological sample is selected from the group consisting of: blood, serum, urine, saliva, cerebrospinal fluid, pleural fluid, and articular fluid.

3. An in vitro diagnostic method for determining the presence of antibodies directed against bacteria of the *Staphylococcus* genus in a biological sample, comprising:
   contacting the biological sample with a purified protein consisting of SEQ ID NO: 10; and
   detecting antibodies present in the biological sample that are bound to said protein.

4. The method of claim 3, wherein the biological sample is selected from the group consisting of: blood, serum, urine, saliva, cerebrospinal fluid, pleural fluid, and articular fluid.

5. The method of claim 1, wherein the amount of antibodies present in the biological sample that are bound to said protein is measured by immunoassay.

6. The method of claim 1, wherein the immunoassay is ELISA.

7. The method of claim 1, wherein the immunoassay is Western blot.

8. The method of claim 5, wherein,
   said protein consisting of SEQ ID NO: 10 is present on a surface of a well of an ELISA plate,
   contacting the biological sample with said protein comprises adding a serum sample from the individual to said well and incubating the ELISA plate for a period of time, and
   said immunoassay comprises:
      adding a secondary antibody comprising goat anti-human immunoglobulin labelled with alkaline phosphatase to said well,
      adding a substrate comprising p-nitrophenyl phosphate to said well, and
      measuring absorbance of said well at 405 nm.

9. The method of claim 1, wherein the individual has a joint prostheses.

10. The method of claim 1, wherein the bacteria of the *Staphylococcus* genus is at least one of *Staphylococcus aureus* and *Staphylococcus epidermidis*.

11. The method of claim 1, wherein determining whether or not the individual is infected by the *Staphylococcus* bacteria comprises comparing the amount of bound antibodies from the biological sample to an amount of bound antibodies from one or more control sample.

12. The method of claim 11, wherein the one or more control sample is a positive control or a negative control.

13. The method of claim 1, wherein the biological sample is serum.

14. An in vitro method for detecting a prosthetic joint infection (PJI) caused by bacteria of the *Staphylococcus* genus in an individual, comprising:
   contacting a biological sample of the individual with a purified protein consisting of SEQ ID NO: 10,
   measuring the amount of antibodies present in the biological sample that are bound to said protein, and
   determining whether or not the individual has the PJI based upon the measured amount.

15. The method of claim 14, wherein the amount of antibodies present in the biological sample that are bound to said protein is measured by immunoassay.

16. The method of claim 14, wherein the bacteria of the *Staphylococcus* genus is at least one of *Staphylococcus aureus* and *Staphylococcus epidermidis*.

17. The method of claim 14, wherein determining whether or not the individual is infected by the *Staphylococcus* bacteria comprises comparing the amount of bound antibodies from the biological sample to an amount of bound antibodies from one or more control sample.

* * * * *

UNITED STATES PATENT AND TRADEMARK OFFICE
CERTIFICATE OF CORRECTION

PATENT NO.        : 8,426,139 B2
APPLICATION NO.   : 12/299971
DATED             : April 23, 2013
INVENTOR(S)       : Jean-Philippe Arie It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1839 days.

Signed and Sealed this
Eighth Day of September, 2015

Michelle K. Lee
*Director of the United States Patent and Trademark Office*

SEQUENCE LISTING

<160> NUMBER OF SEQ ID NOS: 36

<210> SEQ ID NO 1
<211> LENGTH: 1485
<212> TYPE: DNA
<213> ORGANISM: Staphylococcus epidermidis
<220> FEATURE:
<221> NAME/KEY: CDS
<222> LOCATION: (1)..(1485)

<400> SEQUENCE: 1

| gga | act | aat | aat | aaa | tta | act | gtg | tct | gct | aat | cgt | ggt | gtt | gct | caa | 48 |
|---|---|---|---|---|---|---|---|---|---|---|---|---|---|---|---|---|
| Gly | Thr | Asn | Asn | Lys | Leu | Thr | Val | Ser | Ala | Asn | Arg | Gly | Val | Ala | Gln | |
| 1 | | | | 5 | | | | | 10 | | | | | | 15 | |

| att | aaa | cca | aca | aat | aat | ggc | tta | tat | aca | act | gtt | tat | gac | agt | aaa | 96 |
|---|---|---|---|---|---|---|---|---|---|---|---|---|---|---|---|---|
| Ile | Lys | Pro | Thr | Asn | Asn | Gly | Leu | Tyr | Thr | Thr | Val | Tyr | Asp | Ser | Lys | |
| | | | 20 | | | | | 25 | | | | | 30 | | | |

| ggt | cat | aag | act | gat | caa | gta | caa | aaa | act | cta | tcc | gtt | act | aaa | act | 144 |
|---|---|---|---|---|---|---|---|---|---|---|---|---|---|---|---|---|
| Gly | His | Lys | Thr | Asp | Gln | Val | Gln | Lys | Thr | Leu | Ser | Val | Thr | Lys | Thr | |
| | | 35 | | | | | 40 | | | | | 45 | | | | |

| gca | aca | tta | gga | aat | aac | aaa | ttc | tat | tta | gtt | gaa | gac | tac | aat | agc | 192 |
|---|---|---|---|---|---|---|---|---|---|---|---|---|---|---|---|---|
| Ala | Thr | Leu | Gly | Asn | Asn | Lys | Phe | Tyr | Leu | Val | Glu | Asp | Tyr | Asn | Ser | |
| | 50 | | | | | 55 | | | | | 60 | | | | | |

| ggt | aaa | aaa | tac | ggt | tgg | gtt | aaa | caa | ggt | gat | gtt | gtt | tat | aac | act | 240 |
|---|---|---|---|---|---|---|---|---|---|---|---|---|---|---|---|---|
| Gly | Lys | Lys | Tyr | Gly | Trp | Val | Lys | Gln | Gly | Asp | Val | Val | Tyr | Asn | Thr | |
| 65 | | | | | 70 | | | | | 75 | | | | | 80 | |

| gct | aag | gca | cca | gta | aaa | gtg | aat | caa | aca | tat | aat | gtt | aaa | gca | ggg | 288 |
|---|---|---|---|---|---|---|---|---|---|---|---|---|---|---|---|---|
| Ala | Lys | Ala | Pro | Val | Lys | Val | Asn | Gln | Thr | Tyr | Asn | Val | Lys | Ala | Gly | |
| | | | | 85 | | | | | 90 | | | | | 95 | | |

| tca | aca | ctt | tac | aca | gtt | cct | tgg | ggt | aca | cca | aaa | caa | gtt | gct | agc | 336 |
|---|---|---|---|---|---|---|---|---|---|---|---|---|---|---|---|---|
| Ser | Thr | Leu | Tyr | Thr | Val | Pro | Trp | Gly | Thr | Pro | Lys | Gln | Val | Ala | Ser | |
| | | | | 100 | | | | | 105 | | | | | 110 | | |

| aaa | gta | tct | ggt | act | gga | aat | caa | aca | ttt | aaa | gca | act | aaa | cag | caa | 384 |
|---|---|---|---|---|---|---|---|---|---|---|---|---|---|---|---|---|
| Lys | Val | Ser | Gly | Thr | Gly | Asn | Gln | Thr | Phe | Lys | Ala | Thr | Lys | Gln | Gln | |
| | | | 115 | | | | | 120 | | | | | 125 | | | |

| caa | att | gat | aaa | gca | acg | tat | ctt | tat | ggt | aca | gtg | aat | ggt | aaa | tct | 432 |
|---|---|---|---|---|---|---|---|---|---|---|---|---|---|---|---|---|
| Gln | Ile | Asp | Lys | Ala | Thr | Tyr | Leu | Tyr | Gly | Thr | Val | Asn | Gly | Lys | Ser | |
| | | 130 | | | | | 135 | | | | | 140 | | | | |

| ggt | tgg | att | agt | aaa | tat | tac | tta | act | aca | gca | tct | aaa | cct | agc | aat | 480 |
|---|---|---|---|---|---|---|---|---|---|---|---|---|---|---|---|---|
| Gly | Trp | Ile | Ser | Lys | Tyr | Tyr | Leu | Thr | Thr | Ala | Ser | Lys | Pro | Ser | Asn | |
| 145 | | | | | 150 | | | | | 155 | | | | | 160 | |

| cca | act | aaa | cct | tca | aca | aac | aac | caa | tta | aca | gtg | act | aac | aat | agt | 528 |
|---|---|---|---|---|---|---|---|---|---|---|---|---|---|---|---|---|
| Pro | Thr | Lys | Pro | Ser | Thr | Asn | Asn | Gln | Leu | Thr | Val | Thr | Asn | Asn | Ser | |
| | | | | 165 | | | | | 170 | | | | | 175 | | |

| ggt | gtt | gct | caa | atc | aat | gca | aaa | aat | agt | ggc | tta | tat | act | aca | gtt | 576 |
|---|---|---|---|---|---|---|---|---|---|---|---|---|---|---|---|---|
| Gly | Val | Ala | Gln | Ile | Asn | Ala | Lys | Asn | Ser | Gly | Leu | Tyr | Thr | Thr | Val | |
| | | | 180 | | | | | 185 | | | | | 190 | | | |

| tat | gac | act | aaa | gga | aag | aca | aca | aat | caa | atc | caa | cgt | aca | ttg | tca | 624 |
|---|---|---|---|---|---|---|---|---|---|---|---|---|---|---|---|---|
| Tyr | Asp | Thr | Lys | Gly | Lys | Thr | Thr | Asn | Gln | Ile | Gln | Arg | Thr | Leu | Ser | |
| | | 195 | | | | | 200 | | | | | 205 | | | | |

| gtg | acg | aaa | gct | gcc | aca | ctt | ggt | gat | aaa | aaa | ttc | tat | ctt | gtt | ggt | 672 |
|---|---|---|---|---|---|---|---|---|---|---|---|---|---|---|---|---|
| Val | Thr | Lys | Ala | Ala | Thr | Leu | Gly | Asp | Lys | Lys | Phe | Tyr | Leu | Val | Gly | |
| | 210 | | | | | 215 | | | | | 220 | | | | | |

| gat | tat | aat | act | ggt | aca | aat | tat | ggt | tgg | gta | aaa | caa | gat | gag | gtc | 720 |
|---|---|---|---|---|---|---|---|---|---|---|---|---|---|---|---|---|
| Asp | Tyr | Asn | Thr | Gly | Thr | Asn | Tyr | Gly | Trp | Val | Lys | Gln | Asp | Glu | Val | |
| 225 | | | | | 230 | | | | | 235 | | | | | 240 | |

```
att tac aac aca gct aaa tca cct gta aaa atc aat caa aca tac aac         768
Ile Tyr Asn Thr Ala Lys Ser Pro Val Lys Ile Asn Gln Thr Tyr Asn
            245                 250                 255 gtc aaa cct ggt gtt aaa tta cac aca gta cct tgg ggc aca tat aat         816
Val Lys Pro Gly Val Lys Leu His Thr Val Pro Trp Gly Thr Tyr Asn
        260                 265                 270 caa gtg gct gga aca gtt tca ggt aaa ggc gat caa act ttt aaa gca         864
Gln Val Ala Gly Thr Val Ser Gly Lys Gly Asp Gln Thr Phe Lys Ala
    275                 280                 285 act aaa caa caa caa att gat aaa gca aca tat ctt tat ggt aca gtg         912
Thr Lys Gln Gln Gln Ile Asp Lys Ala Thr Tyr Leu Tyr Gly Thr Val
290                 295                 300 aac ggt aaa tct ggt tgg att agt aaa tac tat tta act gca cca tca         960
Asn Gly Lys Ser Gly Trp Ile Ser Lys Tyr Tyr Leu Thr Ala Pro Ser
305                 310                 315                 320 aaa gtt caa gct ttg tct act caa tca aca cca gca cct aaa caa gta        1008
Lys Val Gln Ala Leu Ser Thr Gln Ser Thr Pro Ala Pro Lys Gln Val
            325                 330                 335 aaa cca tct aca caa act gta aat caa att gct caa gtg aaa gct aat        1056
Lys Pro Ser Thr Gln Thr Val Asn Gln Ile Ala Gln Val Lys Ala Asn
        340                 345                 350 aat tct gga ata aga gca tct gta tat gat aaa aca gcc aaa agt ggt        1104
Asn Ser Gly Ile Arg Ala Ser Val Tyr Asp Lys Thr Ala Lys Ser Gly
    355                 360                 365 acg aaa tac gct aac cgt aca ttc ctt atc aat aaa caa cgt act caa        1152
Thr Lys Tyr Ala Asn Arg Thr Phe Leu Ile Asn Lys Gln Arg Thr Gln
370                 375                 380 ggt aat aac acg tat gta cta ctt caa gat gga aca agt aat act cca        1200
Gly Asn Asn Thr Tyr Val Leu Leu Gln Asp Gly Thr Ser Asn Thr Pro
385                 390                 395                 400 tta gga tgg gta aac att aat gat gtg aca act caa aat atc gga aaa        1248
Leu Gly Trp Val Asn Ile Asn Asp Val Thr Thr Gln Asn Ile Gly Lys
            405                 410                 415 caa act cag tct ata ggt aaa tat tca gta aaa cct aca aat aat ggt        1296
Gln Thr Gln Ser Ile Gly Lys Tyr Ser Val Lys Pro Thr Asn Asn Gly
        420                 425                 430 cta tat tct att gct tgg ggt act aaa aac caa caa tta cta gca cct        1344
Leu Tyr Ser Ile Ala Trp Gly Thr Lys Asn Gln Gln Leu Leu Ala Pro
    435                 440                 445 aat acg cta gct aat caa gca ttt aat gct tcc aaa gct gtt tac gtt        1392
Asn Thr Leu Ala Asn Gln Ala Phe Asn Ala Ser Lys Ala Val Tyr Val
450                 455                 460 ggt aaa gat tta tat cta tac ggt aca gtc aat aac aga aca gga tgg        1440
Gly Lys Asp Leu Tyr Leu Tyr Gly Thr Val Asn Asn Arg Thr Gly Trp
465                 470                 475                 480 att gct gct aag gat tta atc caa aac agt act gac gct caa tca             1485
Ile Ala Ala Lys Asp Leu Ile Gln Asn Ser Thr Asp Ala Gln Ser
            485                 490                 495

<210> SEQ ID NO 2
<211> LENGTH: 495
<212> TYPE: PRT
<213> ORGANISM: Staphylococcus epidermidis

<400> SEQUENCE: 2

Gly Thr Asn Asn Lys Leu Thr Val Ser Ala Asn Arg Gly Val Ala Gln
1               5                   10                  15

Ile Lys Pro Thr Asn Asn Gly Leu Tyr Thr Thr Val Tyr Asp Ser Lys
            20                  25                  30

Gly His Lys Thr Asp Gln Val Gln Lys Thr Leu Ser Val Thr Lys Thr
```

```
                  35                  40                  45
Ala Thr Leu Gly Asn Asn Lys Phe Tyr Leu Val Glu Asp Tyr Asn Ser
 50                  55                  60

Gly Lys Lys Tyr Gly Trp Val Lys Gln Gly Asp Val Tyr Asn Thr
 65                  70                  75                  80

Ala Lys Ala Pro Val Lys Val Asn Gln Thr Tyr Asn Val Lys Ala Gly
                 85                  90                  95

Ser Thr Leu Tyr Thr Val Pro Trp Gly Thr Pro Lys Gln Val Ala Ser
                100                 105                 110

Lys Val Ser Gly Thr Gly Asn Gln Thr Phe Lys Ala Thr Lys Gln Gln
                115                 120                 125

Gln Ile Asp Lys Ala Thr Tyr Leu Tyr Gly Thr Val Asn Gly Lys Ser
130                 135                 140

Gly Trp Ile Ser Lys Tyr Tyr Leu Thr Thr Ala Ser Lys Pro Ser Asn
145                 150                 155                 160

Pro Thr Lys Pro Ser Thr Asn Asn Gln Leu Thr Val Thr Asn Asn Ser
                165                 170                 175

Gly Val Ala Gln Ile Asn Ala Lys Asn Ser Gly Leu Tyr Thr Thr Val
                180                 185                 190

Tyr Asp Thr Lys Gly Lys Thr Thr Asn Gln Ile Gln Arg Thr Leu Ser
                195                 200                 205

Val Thr Lys Ala Ala Thr Leu Gly Asp Lys Lys Phe Tyr Leu Val Gly
210                 215                 220

Asp Tyr Asn Thr Gly Thr Asn Tyr Gly Trp Val Lys Gln Asp Glu Val
225                 230                 235                 240

Ile Tyr Asn Thr Ala Lys Ser Pro Val Lys Ile Asn Gln Thr Tyr Asn
                245                 250                 255

Val Lys Pro Gly Val Lys Leu His Thr Val Pro Trp Gly Thr Tyr Asn
                260                 265                 270

Gln Val Ala Gly Thr Val Ser Gly Lys Gly Asp Gln Thr Phe Lys Ala
                275                 280                 285

Thr Lys Gln Gln Gln Ile Asp Lys Ala Thr Tyr Leu Tyr Gly Thr Val
290                 295                 300

Asn Gly Lys Ser Gly Trp Ile Ser Lys Tyr Tyr Leu Thr Ala Pro Ser
305                 310                 315                 320

Lys Val Gln Ala Leu Ser Thr Gln Ser Thr Pro Ala Pro Lys Gln Val
                325                 330                 335

Lys Pro Ser Thr Gln Thr Val Asn Gln Ile Ala Gln Val Lys Ala Asn
                340                 345                 350

Asn Ser Gly Ile Arg Ala Ser Val Tyr Asp Lys Thr Ala Lys Ser Gly
                355                 360                 365

Thr Lys Tyr Ala Asn Arg Thr Phe Leu Ile Asn Lys Gln Arg Thr Gln
370                 375                 380

Gly Asn Asn Thr Tyr Val Leu Leu Gln Asp Gly Thr Ser Asn Thr Pro
385                 390                 395                 400

Leu Gly Trp Val Asn Ile Asn Asp Val Thr Thr Gln Asn Ile Gly Lys
                405                 410                 415

Gln Thr Gln Ser Ile Gly Lys Tyr Ser Val Lys Pro Thr Asn Asn Gly
                420                 425                 430

Leu Tyr Ser Ile Ala Trp Gly Thr Lys Asn Gln Gln Leu Leu Ala Pro
                435                 440                 445

Asn Thr Leu Ala Asn Gln Ala Phe Asn Ala Ser Lys Ala Val Tyr Val
450                 455                 460
```

```
Gly Lys Asp Leu Tyr Leu Tyr Gly Thr Val Asn Asn Arg Thr Gly Trp
465                 470                 475                 480

Ile Ala Ala Lys Asp Leu Ile Gln Asn Ser Thr Asp Ala Gln Ser
                485                 490                 495

<210> SEQ ID NO 3
<211> LENGTH: 561
<212> TYPE: DNA
<213> ORGANISM: Staphylococcus epidermidis
<220> FEATURE:
<221> NAME/KEY: CDS
<222> LOCATION: (1)..(561)

<400> SEQUENCE: 3 gga act aat aat aaa tta act gtg tct gct aat cgt ggt gtt gct caa        48
Gly Thr Asn Asn Lys Leu Thr Val Ser Ala Asn Arg Gly Val Ala Gln
1               5                   10                  15 att aaa cca aca aat aat ggc tta tat aca act gtt tat gac agt aaa        96
Ile Lys Pro Thr Asn Asn Gly Leu Tyr Thr Thr Val Tyr Asp Ser Lys
            20                  25                  30 ggt cat aag act gat caa gta caa aaa act cta tcc gtt act aaa act       144
Gly His Lys Thr Asp Gln Val Gln Lys Thr Leu Ser Val Thr Lys Thr
        35                  40                  45 gca aca tta gga aat aac aaa ttc tat tta gtt gaa gac tac aat agc       192
Ala Thr Leu Gly Asn Asn Lys Phe Tyr Leu Val Glu Asp Tyr Asn Ser
    50                  55                  60 ggt aaa aaa tac ggt tgg gtt aaa caa ggt gat gtt gtt tat aac act       240
Gly Lys Lys Tyr Gly Trp Val Lys Gln Gly Asp Val Val Tyr Asn Thr
65                  70                  75                  80 gct aag gca cca gta aaa gtg aat caa aca tat aat gtt aaa gca ggg       288
Ala Lys Ala Pro Val Lys Val Asn Gln Thr Tyr Asn Val Lys Ala Gly
                85                  90                  95 tca aca ctt tac aca gtt cct tgg ggt aca cca aaa caa gtt gct agc       336
Ser Thr Leu Tyr Thr Val Pro Trp Gly Thr Pro Lys Gln Val Ala Ser
            100                 105                 110 aaa gta tct ggt act gga aat caa aca ttt aaa gca act aaa cag caa       384
Lys Val Ser Gly Thr Gly Asn Gln Thr Phe Lys Ala Thr Lys Gln Gln
        115                 120                 125 caa att gat aaa gca acg tat ctt tat ggt aca gtg aat ggt aaa tct       432
Gln Ile Asp Lys Ala Thr Tyr Leu Tyr Gly Thr Val Asn Gly Lys Ser
    130                 135                 140 ggt tgg att agt aaa tat tac tta act aca gca tct aaa cct agc aat       480
Gly Trp Ile Ser Lys Tyr Tyr Leu Thr Thr Ala Ser Lys Pro Ser Asn
145                 150                 155                 160 cca act aaa cct tca aca aac aac caa tta aca gtg act aac aat agt       528
Pro Thr Lys Pro Ser Thr Asn Asn Gln Leu Thr Val Thr Asn Asn Ser
                165                 170                 175 ggt gtt gct caa atc aat gca aaa aat agt ggc                           561
Gly Val Ala Gln Ile Asn Ala Lys Asn Ser Gly
            180                 185

<210> SEQ ID NO 4
<211> LENGTH: 187
<212> TYPE: PRT
<213> ORGANISM: Staphylococcus epidermidis

<400> SEQUENCE: 4

Gly Thr Asn Asn Lys Leu Thr Val Ser Ala Asn Arg Gly Val Ala Gln
1               5                   10                  15

Ile Lys Pro Thr Asn Asn Gly Leu Tyr Thr Thr Val Tyr Asp Ser Lys
            20                  25                  30

Gly His Lys Thr Asp Gln Val Gln Lys Thr Leu Ser Val Thr Lys Thr
```

```
                   35                  40                  45
Ala Thr Leu Gly Asn Asn Lys Phe Tyr Leu Val Glu Asp Tyr Asn Ser
         50                  55                  60
Gly Lys Lys Tyr Gly Trp Val Lys Gln Gly Asp Val Val Tyr Asn Thr
 65                  70                  75                  80
Ala Lys Ala Pro Val Lys Val Asn Gln Thr Tyr Asn Val Lys Ala Gly
                 85                  90                  95
Ser Thr Leu Tyr Thr Val Pro Trp Gly Thr Pro Lys Gln Val Ala Ser
            100                 105                 110
Lys Val Ser Gly Thr Gly Asn Gln Thr Phe Lys Ala Thr Lys Gln Gln
        115                 120                 125
Gln Ile Asp Lys Ala Thr Tyr Leu Tyr Gly Thr Val Asn Gly Lys Ser
    130                 135                 140
Gly Trp Ile Ser Lys Tyr Tyr Leu Thr Thr Ala Ser Lys Pro Ser Asn
145                 150                 155                 160
Pro Thr Lys Pro Ser Thr Asn Asn Gln Leu Thr Val Thr Asn Asn Ser
                165                 170                 175
Gly Val Ala Gln Ile Asn Ala Lys Asn Ser Gly
            180                 185

<210> SEQ ID NO 5
<211> LENGTH: 1524
<212> TYPE: DNA
<213> ORGANISM: Staphylococcus aureus
<220> FEATURE:
<221> NAME/KEY: CDS
<222> LOCATION: (1)..(1524)

<400> SEQUENCE: 5 tca act ggt aaa tta aca gtt gct gca aac aat ggt gtc gca caa atc      48
Ser Thr Gly Lys Leu Thr Val Ala Ala Asn Asn Gly Val Ala Gln Ile
 1               5                  10                  15 aaa cca aca aat agt ggt tta tat act act gta tac gac aaa act ggt      96
Lys Pro Thr Asn Ser Gly Leu Tyr Thr Thr Val Tyr Asp Lys Thr Gly
             20                  25                  30 aaa gca act aat gaa gtt caa aaa aca ttt gct gta tct aaa aca gct     144
Lys Ala Thr Asn Glu Val Gln Lys Thr Phe Ala Val Ser Lys Thr Ala
         35                  40                  45 aca tta ggt aat caa aaa ttc tat ctt gtt caa gat tac aat tct ggt     192
Thr Leu Gly Asn Gln Lys Phe Tyr Leu Val Gln Asp Tyr Asn Ser Gly
     50                  55                  60 aat aaa ttt ggt tgg gtt aaa gaa ggc gat gtg gtt tac aac aca gct     240
Asn Lys Phe Gly Trp Val Lys Glu Gly Asp Val Val Tyr Asn Thr Ala
 65                  70                  75                  80 aaa tca cct gta aat gta aat caa tca tat tca atc aaa cct ggt acg     288
Lys Ser Pro Val Asn Val Asn Gln Ser Tyr Ser Ile Lys Pro Gly Thr
                 85                  90                  95 aaa ctt tat aca gta cct tgg ggt aca tct aaa caa gtt gct ggt agt     336
Lys Leu Tyr Thr Val Pro Trp Gly Thr Ser Lys Gln Val Ala Gly Ser
            100                 105                 110 gtg tct ggc tct gga aac caa aca ttt aag gct tca aag caa caa caa     384
Val Ser Gly Ser Gly Asn Gln Thr Phe Lys Ala Ser Lys Gln Gln Gln
        115                 120                 125 att gat aaa tca att tat tta tat ggc tct gtg aat ggt aaa tct ggt     432
Ile Asp Lys Ser Ile Tyr Leu Tyr Gly Ser Val Asn Gly Lys Ser Gly
    130                 135                 140 tgg gta agt aaa gca tat tta gtt gat act gct aaa cct acg cct aca     480
Trp Val Ser Lys Ala Tyr Leu Val Asp Thr Ala Lys Pro Thr Pro Thr
145                 150                 155                 160
```

```
cca aca cct aag cca tca aca cct aca aca aat aat aaa tta aca gtt        528
Pro Thr Pro Lys Pro Ser Thr Pro Thr Thr Asn Asn Lys Leu Thr Val
            165                 170                 175 tca tca tta aac ggt gtt gct caa att aat gct aaa aac aat ggc tta        576
Ser Ser Leu Asn Gly Val Ala Gln Ile Asn Ala Lys Asn Asn Gly Leu
            180                 185                 190 ttc act aca gtt tat gac aaa act ggt aag cca acg aaa gaa gtt caa        624
Phe Thr Thr Val Tyr Asp Lys Thr Gly Lys Pro Thr Lys Glu Val Gln
            195                 200                 205 aaa aca ttt gct gta aca aaa gaa gca agt tta ggt gga aac aaa ttc        672
Lys Thr Phe Ala Val Thr Lys Glu Ala Ser Leu Gly Gly Asn Lys Phe
            210                 215                 220 tac tta gtt aaa gat tac aat agt cca act tta att ggt tgg gtt aaa        720
Tyr Leu Val Lys Asp Tyr Asn Ser Pro Thr Leu Ile Gly Trp Val Lys
225                 230                 235                 240 caa ggt gac gtt att tat aac aat gca aaa tca cct gta aat gta atg        768
Gln Gly Asp Val Ile Tyr Asn Asn Ala Lys Ser Pro Val Asn Val Met
                245                 250                 255 caa aca tat aca gta aaa cca ggc act aaa tta tat tca gta cct tgg        816
Gln Thr Tyr Thr Val Lys Pro Gly Thr Lys Leu Tyr Ser Val Pro Trp
            260                 265                 270 ggc act tat aaa caa gaa gct ggt gca gtt tct ggt aca ggt aac caa        864
Gly Thr Tyr Lys Gln Glu Ala Gly Ala Val Ser Gly Thr Gly Asn Gln
            275                 280                 285 act ttt aaa gcg act aag caa caa caa att gat aaa tct atc tat tta        912
Thr Phe Lys Ala Thr Lys Gln Gln Gln Ile Asp Lys Ser Ile Tyr Leu
            290                 295                 300 ttt gga act gta aat ggt aaa tct ggt tgg gta agt aaa gca tat tta        960
Phe Gly Thr Val Asn Gly Lys Ser Gly Trp Val Ser Lys Ala Tyr Leu
305                 310                 315                 320 gct gta cct gct gca cct aaa aaa gca gta gca caa cca aaa aca gct       1008
Ala Val Pro Ala Ala Pro Lys Lys Ala Val Ala Gln Pro Lys Thr Ala
                325                 330                 335 gta aaa gct tat act gtt act aaa cca caa acg act caa aca gtt agc       1056
Val Lys Ala Tyr Thr Val Thr Lys Pro Gln Thr Thr Gln Thr Val Ser
            340                 345                 350 aag att gct caa gtt aaa cca aac aac act ggt att cgt gct tct gtt       1104
Lys Ile Ala Gln Val Lys Pro Asn Asn Thr Gly Ile Arg Ala Ser Val
            355                 360                 365 tat gaa aaa aca gcg aaa aac ggt gcg aaa tat gca gac cgt acg ttc       1152
Tyr Glu Lys Thr Ala Lys Asn Gly Ala Lys Tyr Ala Asp Arg Thr Phe
            370                 375                 380 tat gta aca aaa gag cgt gct cat ggt aat gaa acg tat gta tta tta       1200
Tyr Val Thr Lys Glu Arg Ala His Gly Asn Glu Thr Tyr Val Leu Leu
385                 390                 395                 400 aac aat aca agc cat aac atc cca tta ggt tgg ttc aat gta aaa gac       1248
Asn Asn Thr Ser His Asn Ile Pro Leu Gly Trp Phe Asn Val Lys Asp
                405                 410                 415 tta aat gtt caa aac tta ggc aaa gaa gtt aaa acg act caa aaa tat       1296
Leu Asn Val Gln Asn Leu Gly Lys Glu Val Lys Thr Thr Gln Lys Tyr
            420                 425                 430 act gtt aat aaa tca aat aac ggc tta tca atg gtt cct tgg ggt act       1344
Thr Val Asn Lys Ser Asn Asn Gly Leu Ser Met Val Pro Trp Gly Thr
            435                 440                 445 aaa aac caa gtc att tta aca ggc aat aac att gct caa ggt aca ttt       1392
Lys Asn Gln Val Ile Leu Thr Gly Asn Asn Ile Ala Gln Gly Thr Phe
            450                 455                 460 aat gca acg aaa caa gta tct gta ggc aaa gat gtt tat tta tac ggt       1440
Asn Ala Thr Lys Gln Val Ser Val Gly Lys Asp Val Tyr Leu Tyr Gly
465                 470                 475                 480
```

```
act att aat aac cgc act ggt tgg gta aat gca aaa gat tta act gca    1488
Thr Ile Asn Asn Arg Thr Gly Trp Val Asn Ala Lys Asp Leu Thr Ala
            485                 490                 495 cca act gct gtt aaa cca act aca tca gct gcc aaa                   1524
Pro Thr Ala Val Lys Pro Thr Thr Ser Ala Ala Lys
500                 505

<210> SEQ ID NO 6
<211> LENGTH: 508
<212> TYPE: PRT
<213> ORGANISM: Staphylococcus aureus

<400> SEQUENCE: 6

Ser Thr Gly Lys Leu Thr Val Ala Ala Asn Gly Val Ala Gln Ile
1               5                   10                  15

Lys Pro Thr Asn Ser Gly Leu Tyr Thr Thr Val Tyr Asp Lys Thr Gly
            20                  25                  30

Lys Ala Thr Asn Glu Val Gln Lys Thr Phe Ala Val Ser Lys Thr Ala
        35                  40                  45

Thr Leu Gly Asn Gln Lys Phe Tyr Leu Val Gln Asp Tyr Asn Ser Gly
    50                  55                  60

Asn Lys Phe Gly Trp Val Lys Glu Gly Asp Val Val Tyr Asn Thr Ala
65                  70                  75                  80

Lys Ser Pro Val Asn Val Asn Gln Ser Tyr Ser Ile Lys Pro Gly Thr
                85                  90                  95

Lys Leu Tyr Thr Val Pro Trp Gly Thr Ser Lys Gln Val Ala Gly Ser
            100                 105                 110

Val Ser Gly Ser Gly Asn Gln Thr Phe Lys Ala Ser Lys Gln Gln Gln
        115                 120                 125

Ile Asp Lys Ser Ile Tyr Leu Tyr Gly Ser Val Asn Gly Lys Ser Gly
    130                 135                 140

Trp Val Ser Lys Ala Tyr Leu Val Asp Thr Ala Lys Pro Thr Pro Thr
145                 150                 155                 160

Pro Thr Pro Lys Pro Ser Thr Pro Thr Thr Asn Asn Lys Leu Thr Val
                165                 170                 175

Ser Ser Leu Asn Gly Val Ala Gln Ile Asn Ala Lys Asn Asn Gly Leu
            180                 185                 190

Phe Thr Thr Val Tyr Asp Lys Thr Gly Lys Pro Thr Lys Glu Val Gln
        195                 200                 205

Lys Thr Phe Ala Val Thr Lys Glu Ala Ser Leu Gly Gly Asn Lys Phe
    210                 215                 220

Tyr Leu Val Lys Asp Tyr Asn Ser Pro Thr Leu Ile Gly Trp Val Lys
225                 230                 235                 240

Gln Gly Asp Val Ile Tyr Asn Asn Ala Lys Ser Pro Val Asn Val Met
                245                 250                 255

Gln Thr Tyr Thr Val Lys Pro Gly Thr Lys Leu Tyr Ser Val Pro Trp
            260                 265                 270

Gly Thr Tyr Lys Gln Glu Ala Gly Ala Val Ser Gly Thr Gly Asn Gln
        275                 280                 285

Thr Phe Lys Ala Thr Lys Gln Gln Gln Ile Asp Lys Ser Ile Tyr Leu
    290                 295                 300

Phe Gly Thr Val Asn Gly Lys Ser Gly Trp Val Ser Lys Ala Tyr Leu
305                 310                 315                 320

Ala Val Pro Ala Ala Pro Lys Lys Ala Val Ala Gln Pro Lys Thr Ala
                325                 330                 335

Val Lys Ala Tyr Thr Val Thr Lys Pro Gln Thr Thr Gln Thr Val Ser
```

```
                          340               345               350
Lys Ile Ala Gln Val Lys Pro Asn Asn Thr Gly Ile Arg Ala Ser Val
                355                 360                 365

Tyr Glu Lys Thr Ala Lys Asn Gly Ala Lys Tyr Ala Asp Arg Thr Phe
        370                 375                 380

Tyr Val Thr Lys Glu Arg Ala His Gly Asn Glu Thr Tyr Val Leu Leu
385                 390                 395                 400

Asn Asn Thr Ser His Asn Ile Pro Leu Gly Trp Phe Asn Val Lys Asp
                405                 410                 415

Leu Asn Val Gln Asn Leu Gly Lys Glu Val Lys Thr Thr Gln Lys Tyr
                420                 425                 430

Thr Val Asn Lys Ser Asn Asn Gly Leu Ser Met Val Pro Trp Gly Thr
                435                 440                 445

Lys Asn Gln Val Ile Leu Thr Gly Asn Asn Ile Ala Gln Gly Thr Phe
            450                 455                 460

Asn Ala Thr Lys Gln Val Ser Val Gly Lys Asp Val Tyr Leu Tyr Gly
465                 470                 475                 480

Thr Ile Asn Asn Arg Thr Gly Trp Val Asn Ala Lys Asp Leu Thr Ala
                485                 490                 495

Pro Thr Ala Val Lys Pro Thr Thr Ser Ala Ala Lys
            500                 505

<210> SEQ ID NO 7
<211> LENGTH: 579
<212> TYPE: DNA
<213> ORGANISM: Staphylococcus caprae
<220> FEATURE:
<221> NAME/KEY: CDS
<222> LOCATION: (1)..(579)

<400> SEQUENCE: 7 tca aac aac aat aaa tta act gtt tct gct aat agt ggt gtt gct caa     48
Ser Asn Asn Asn Lys Leu Thr Val Ser Ala Asn Ser Gly Val Ala Gln
  1               5                  10                  15 att aaa cct agc aat agt ggc ctt tac aca act gtt tat gac gaa aaa     96
Ile Lys Pro Ser Asn Ser Gly Leu Tyr Thr Thr Val Tyr Asp Glu Lys
             20                  25                  30 gga cat tca aca gat caa gct caa aaa aca tta tct gtt act aaa tct    144
Gly His Ser Thr Asp Gln Ala Gln Lys Thr Leu Ser Val Thr Lys Ser
         35                  40                  45 gca aca ctt ggc aat aat aaa ttc tat tta gtc gaa gat tac aac act    192
Ala Thr Leu Gly Asn Asn Lys Phe Tyr Leu Val Glu Asp Tyr Asn Thr
     50                  55                  60 ggt aaa aag tat ggc tgg gta aaa caa ggc gat gtt gtt tat aat aca    240
Gly Lys Lys Tyr Gly Trp Val Lys Gln Gly Asp Val Val Tyr Asn Thr
 65                  70                  75                  80 gct aaa tca cct gtt aaa gtt aac caa aca tat aat gta aaa gct ggt    288
Ala Lys Ser Pro Val Lys Val Asn Gln Thr Tyr Asn Val Lys Ala Gly
                 85                  90                  95 tca act tta tac aca gta cct tgg ggt acg cct agt caa gta gct tca    336
Ser Thr Leu Tyr Thr Val Pro Trp Gly Thr Pro Ser Gln Val Ala Ser
            100                 105                 110 aag gtt tca ggt tct gga aat caa aca ttt aaa gct aca aaa caa caa    384
Lys Val Ser Gly Ser Gly Asn Gln Thr Phe Lys Ala Thr Lys Gln Gln
        115                 120                 125 caa att gat aaa gcc att tat tta tac gga aca gtg aac ggt aaa tct    432
Gln Ile Asp Lys Ala Ile Tyr Leu Tyr Gly Thr Val Asn Gly Lys Ser
    130                 135                 140 ggt tgg att agt aaa tat tac tta aca aca cct tca tcg tct aat acg    480
```

```
Gly Trp Ile Ser Lys Tyr Tyr Leu Thr Thr Pro Ser Ser Ser Asn Thr
145                 150                 155                 160 aaa cca agt aaa cca tcg aca gat aat agt tca agt aat aat aaa tta    528
Lys Pro Ser Lys Pro Ser Thr Asp Asn Ser Ser Ser Asn Asn Lys Leu
                165                 170                 175 act gtt tct gct aac agt ggt gtt gct caa att aaa gct aaa aat aat    576
Thr Val Ser Ala Asn Ser Gly Val Ala Gln Ile Lys Ala Lys Asn Asn
            180                 185                 190 ggt                                                                579
Gly

<210> SEQ ID NO 8
<211> LENGTH: 193
<212> TYPE: PRT
<213> ORGANISM: Staphylococcus caprae

<400> SEQUENCE: 8

Ser Asn Asn Lys Leu Thr Val Ser Ala Asn Ser Gly Val Ala Gln
1               5                   10                  15

Ile Lys Pro Ser Asn Ser Gly Leu Tyr Thr Val Tyr Asp Glu Lys
                20                  25                  30

Gly His Ser Thr Asp Gln Ala Gln Lys Thr Leu Ser Val Thr Lys Ser
            35                  40                  45

Ala Thr Leu Gly Asn Asn Lys Phe Tyr Leu Val Glu Asp Tyr Asn Thr
        50                  55                  60

Gly Lys Lys Tyr Gly Trp Val Lys Gln Gly Asp Val Val Tyr Asn Thr
65                  70                  75                  80

Ala Lys Ser Pro Val Lys Val Asn Gln Thr Tyr Asn Val Lys Ala Gly
                85                  90                  95

Ser Thr Leu Tyr Thr Val Pro Trp Gly Thr Pro Ser Gln Val Ala Ser
                100                 105                 110

Lys Val Ser Gly Ser Gly Asn Gln Thr Phe Lys Ala Thr Lys Gln Gln
            115                 120                 125

Gln Ile Asp Lys Ala Ile Tyr Leu Tyr Gly Thr Val Asn Gly Lys Ser
        130                 135                 140

Gly Trp Ile Ser Lys Tyr Tyr Leu Thr Thr Pro Ser Ser Ser Asn Thr
145                 150                 155                 160

Lys Pro Ser Lys Pro Ser Thr Asp Asn Ser Ser Ser Asn Asn Lys Leu
                165                 170                 175

Thr Val Ser Ala Asn Ser Gly Val Ala Gln Ile Lys Ala Lys Asn Asn
            180                 185                 190

Gly

<210> SEQ ID NO 9
<211> LENGTH: 696
<212> TYPE: DNA
<213> ORGANISM: Staphylococcus epidermidis
<220> FEATURE:
<221> NAME/KEY: CDS
<222> LOCATION: (1)..(696)

<400> SEQUENCE: 9 ggt aag cca gga gtt aaa aat cct gat aca ggc gaa gta gtc aca cca    48
Gly Lys Pro Gly Val Lys Asn Pro Asp Thr Gly Glu Val Val Thr Pro
1               5                   10                  15 cca gtg gat gat gtg aca aaa tat ggt cca gtt gat gga gat ccg att    96
Pro Val Asp Asp Val Thr Lys Tyr Gly Pro Val Asp Gly Asp Pro Ile
                20                  25                  30 acg tca acg gaa gaa att ccg ttt gat aaa aaa cgc gaa ttt gat cca    144
```

```
Thr Ser Thr Glu Glu Ile Pro Phe Asp Lys Lys Arg Glu Phe Asp Pro
         35                  40                  45 aac tta gcg cca ggt aca gag aaa gtc gtt caa aaa ggt gaa cca gga    192
Asn Leu Ala Pro Gly Thr Glu Lys Val Val Gln Lys Gly Glu Pro Gly
 50                  55                  60 aca aaa aca att aca acg cca aca act aag aac cca tta aca gga gaa    240
Thr Lys Thr Ile Thr Thr Pro Thr Thr Lys Asn Pro Leu Thr Gly Glu
 65                  70                  75                  80 aaa gtt ggc gaa ggt gaa cca aca gaa aaa ata aca aaa caa cca gtg    288
Lys Val Gly Glu Gly Glu Pro Thr Glu Lys Ile Thr Lys Gln Pro Val
                 85                  90                  95 gat gag att gtt cat tat ggt ggt gaa caa ata cca caa ggt cat aaa    336
Asp Glu Ile Val His Tyr Gly Gly Glu Gln Ile Pro Gln Gly His Lys
                100                 105                 110 gat gaa ttt gat cca aat gca cct gta gat agt aaa act gaa gtt cca    384
Asp Glu Phe Asp Pro Asn Ala Pro Val Asp Ser Lys Thr Glu Val Pro
            115                 120                 125 ggt aaa cca gga gtt aaa aat cct gat aca ggt gaa gtt gtt acc cca    432
Gly Lys Pro Gly Val Lys Asn Pro Asp Thr Gly Glu Val Val Thr Pro
        130                 135                 140 cca gtg gat gat gtg aca aaa tat ggt ccg aaa gtt ggt aat cca atc    480
Pro Val Asp Asp Val Thr Lys Tyr Gly Pro Lys Val Gly Asn Pro Ile
145                 150                 155                 160 aca tca acg gaa gag att cca ttt gat aag aaa cgt gta ttt aat cct    528
Thr Ser Thr Glu Glu Ile Pro Phe Asp Lys Lys Arg Val Phe Asn Pro
                165                 170                 175 gat tta aaa cca ggt gaa gag cgc gtt aaa caa aaa ggt gaa cca gga    576
Asp Leu Lys Pro Gly Glu Glu Arg Val Lys Gln Lys Gly Glu Pro Gly
            180                 185                 190 aca aaa aca att aca aca cca ata tta gtt aat cct att aca gga gaa    624
Thr Lys Thr Ile Thr Thr Pro Ile Leu Val Asn Pro Ile Thr Gly Glu
        195                 200                 205 aaa gtt ggc gaa ggt aaa tca aca gaa aaa gtc act aaa caa cct gtt    672
Lys Val Gly Glu Gly Lys Ser Thr Glu Lys Val Thr Lys Gln Pro Val
    210                 215                 220 gac gaa att gtt gag tat ggt cca                                    696
Asp Glu Ile Val Glu Tyr Gly Pro
225                 230
```

<210> SEQ ID NO 10
<211> LENGTH: 232
<212> TYPE: PRT
<213> ORGANISM: Staphylococcus epidermidis

<400> SEQUENCE: 10

```
Gly Lys Pro Gly Val Lys Asn Pro Asp Thr Gly Glu Val Val Thr Pro
  1               5                  10                  15

Pro Val Asp Asp Val Thr Lys Tyr Gly Pro Val Asp Gly Asp Pro Ile
             20                  25                  30

Thr Ser Thr Glu Glu Ile Pro Phe Asp Lys Lys Arg Glu Phe Asp Pro
         35                  40                  45

Asn Leu Ala Pro Gly Thr Glu Lys Val Val Gln Lys Gly Glu Pro Gly
 50                  55                  60

Thr Lys Thr Ile Thr Thr Pro Thr Thr Lys Asn Pro Leu Thr Gly Glu
 65                  70                  75                  80

Lys Val Gly Glu Gly Glu Pro Thr Glu Lys Ile Thr Lys Gln Pro Val
                 85                  90                  95

Asp Glu Ile Val His Tyr Gly Gly Glu Gln Ile Pro Gln Gly His Lys
                100                 105                 110
```

```
Asp Glu Phe Asp Pro Asn Ala Pro Val Asp Ser Lys Thr Glu Val Pro
        115                 120                 125

Gly Lys Pro Gly Val Lys Asn Pro Asp Thr Gly Glu Val Val Thr Pro
    130                 135                 140

Pro Val Asp Asp Val Thr Lys Tyr Gly Pro Lys Val Gly Asn Pro Ile
145                 150                 155                 160

Thr Ser Thr Glu Glu Ile Pro Phe Asp Lys Lys Arg Val Phe Asn Pro
                165                 170                 175

Asp Leu Lys Pro Gly Glu Glu Arg Val Lys Gln Lys Gly Glu Pro Gly
            180                 185                 190

Thr Lys Thr Ile Thr Thr Pro Ile Leu Val Asn Pro Ile Thr Gly Glu
        195                 200                 205

Lys Val Gly Glu Gly Lys Ser Thr Glu Lys Val Thr Lys Gln Pro Val
    210                 215                 220

Asp Glu Ile Val Glu Tyr Gly Pro
225                 230

<210> SEQ ID NO 11
<211> LENGTH: 843
<212> TYPE: DNA
<213> ORGANISM: Staphylococcus epidermidis
<220> FEATURE:
<221> NAME/KEY: CDS
<222> LOCATION: (1)..(843)

<400> SEQUENCE: 11 aaa aag aga ttt tta tct ata tgt aca atg aca att gca gcg tta gca      48
Lys Lys Arg Phe Leu Ser Ile Cys Thr Met Thr Ile Ala Ala Leu Ala
1               5                   10                  15 act act aca atg gta aat act tct tat gca aaa acc gat aca gaa agc      96
Thr Thr Thr Met Val Asn Thr Ser Tyr Ala Lys Thr Asp Thr Glu Ser
            20                  25                  30 cat aat cat tcc tca ctt ggc aca gaa aac aaa aat gtt tta gat att     144
His Asn His Ser Ser Leu Gly Thr Glu Asn Lys Asn Val Leu Asp Ile
        35                  40                  45 aat agt tcg agt cat aat atc aaa cca agt caa aat aaa agt tac cca     192
Asn Ser Ser Ser His Asn Ile Lys Pro Ser Gln Asn Lys Ser Tyr Pro
    50                  55                  60 agt gta ata tta cct aat aat aat aga cat caa att ttt aat act aca     240
Ser Val Ile Leu Pro Asn Asn Asn Arg His Gln Ile Phe Asn Thr Thr
65                  70                  75                  80 caa ggt cat tat gat gct gtt agt ttt att tat ata cca ata gat ggt     288
Gln Gly His Tyr Asp Ala Val Ser Phe Ile Tyr Ile Pro Ile Asp Gly
                85                  90                  95 gga tat atg agt ggt tca ggt gtt gtt gta ggt gaa aat gaa ata tta     336
Gly Tyr Met Ser Gly Ser Gly Val Val Val Gly Glu Asn Glu Ile Leu
            100                 105                 110 act aat aaa cac gtt gtt aat gga gct aag ggt aat cca aga aat att     384
Thr Asn Lys His Val Val Asn Gly Ala Lys Gly Asn Pro Arg Asn Ile
        115                 120                 125 agt gtc cat cct tca gct aaa aat gaa aat gat tat cct aat ggc aaa     432
Ser Val His Pro Ser Ala Lys Asn Glu Asn Asp Tyr Pro Asn Gly Lys
    130                 135                 140 ttt gtg ggt caa gaa atc ata ccg tat cct ggt aat agt gat tta gca     480
Phe Val Gly Gln Glu Ile Ile Pro Tyr Pro Gly Asn Ser Asp Leu Ala
145                 150                 155                 160 atc tta aga gtg tca cca aac gaa cat aat caa cat att ggt caa gta     528
Ile Leu Arg Val Ser Pro Asn Glu His Asn Gln His Ile Gly Gln Val
                165                 170                 175 gtt aaa cct gca act ata agt agc aat aca gac act aga att aat gaa     576
Val Lys Pro Ala Thr Ile Ser Ser Asn Thr Asp Thr Arg Ile Asn Glu
```

```
Val Lys Pro Ala Thr Ile Ser Ser Asn Thr Asp Thr Arg Ile Asn Glu
            180                 185                 190 aac atc act gtt act ggt tac cct ggt gac aaa cca tta gcc aca atg      624
Asn Ile Thr Val Thr Gly Tyr Pro Gly Asp Lys Pro Leu Ala Thr Met
        195                 200                 205 tgg gaa agt gta ggt aaa gtt gtc tat att ggt ggc gag gaa tta aga      672
Trp Glu Ser Val Gly Lys Val Val Tyr Ile Gly Gly Glu Glu Leu Arg
    210                 215                 220 tat gac cta agt act gta ggt gga aac tct gga tct cca gta ttt aat      720
Tyr Asp Leu Ser Thr Val Gly Gly Asn Ser Gly Ser Pro Val Phe Asn
225                 230                 235                 240 ggt aaa aat caa gtt att gga ata cat tat ggt ggc gta gat aat aaa      768
Gly Lys Asn Gln Val Ile Gly Ile His Tyr Gly Gly Val Asp Asn Lys
                245                 250                 255 tac aat agc agt gtt tat att aat gat ttc gtt caa caa ttc cta aga      816
Tyr Asn Ser Ser Val Tyr Ile Asn Asp Phe Val Gln Gln Phe Leu Arg
            260                 265                 270 aac aat ata cct gat ata aat att cag                                  843
Asn Asn Ile Pro Asp Ile Asn Ile Gln
        275                 280

<210> SEQ ID NO 12
<211> LENGTH: 281
<212> TYPE: PRT
<213> ORGANISM: Staphylococcus epidermidis

<400> SEQUENCE: 12

Lys Lys Arg Phe Leu Ser Ile Cys Thr Met Thr Ile Ala Ala Leu Ala
1               5                   10                  15

Thr Thr Thr Met Val Asn Thr Ser Tyr Ala Lys Thr Asp Thr Glu Ser
            20                  25                  30

His Asn His Ser Ser Leu Gly Thr Glu Asn Lys Asn Val Leu Asp Ile
        35                  40                  45

Asn Ser Ser Ser His Asn Ile Lys Pro Ser Gln Asn Lys Ser Tyr Pro
    50                  55                  60

Ser Val Ile Leu Pro Asn Asn Asn Arg His Gln Ile Phe Asn Thr Thr
65                  70                  75                  80

Gln Gly His Tyr Asp Ala Val Ser Phe Ile Tyr Ile Pro Ile Asp Gly
                85                  90                  95

Gly Tyr Met Ser Gly Ser Val Val Val Gly Glu Asn Glu Ile Leu
            100                 105                 110

Thr Asn Lys His Val Val Asn Gly Ala Lys Gly Asn Pro Arg Asn Ile
        115                 120                 125

Ser Val His Pro Ser Ala Lys Asn Glu Asn Asp Tyr Pro Asn Gly Lys
    130                 135                 140

Phe Val Gly Gln Glu Ile Ile Pro Tyr Pro Gly Asn Ser Asp Leu Ala
145                 150                 155                 160

Ile Leu Arg Val Ser Pro Asn Glu His Asn Gln His Ile Gly Gln Val
                165                 170                 175

Val Lys Pro Ala Thr Ile Ser Ser Asn Thr Asp Thr Arg Ile Asn Glu
            180                 185                 190

Asn Ile Thr Val Thr Gly Tyr Pro Gly Asp Lys Pro Leu Ala Thr Met
        195                 200                 205

Trp Glu Ser Val Gly Lys Val Val Tyr Ile Gly Gly Glu Glu Leu Arg
    210                 215                 220

Tyr Asp Leu Ser Thr Val Gly Gly Asn Ser Gly Ser Pro Val Phe Asn
225                 230                 235                 240
```

```
Gly Lys Asn Gln Val Ile Gly Ile His Tyr Gly Gly Val Asp Asn Lys
                245                 250                 255

Tyr Asn Ser Ser Val Tyr Ile Asn Asp Phe Val Gln Gln Phe Leu Arg
            260                 265                 270

Asn Asn Ile Pro Asp Ile Asn Ile Gln
            275                 280

<210> SEQ ID NO 13
<211> LENGTH: 1068
<212> TYPE: DNA
<213> ORGANISM: Staphylococcus aureus
<220> FEATURE:
<221> NAME/KEY: CDS
<222> LOCATION: (1)..(1068)

<400> SEQUENCE: 13 aaa ggt aaa ttt tta aaa gtt agt tct tta ttc gtt gca act ttg aca      48
Lys Gly Lys Phe Leu Lys Val Ser Ser Leu Phe Val Ala Thr Leu Thr
1               5                   10                  15 aca gcg aca ctt gtg agt tct cca gca gca aat gcg tta tct tca aaa      96
Thr Ala Thr Leu Val Ser Ser Pro Ala Ala Asn Ala Leu Ser Ser Lys
            20                  25                  30 gct atg gac aat cat cca caa caa acg cag aca gac aaa cag caa aca     144
Ala Met Asp Asn His Pro Gln Gln Thr Gln Thr Asp Lys Gln Gln Thr
        35                  40                  45 cct aag att caa aaa ggc ggt aac ctt aaa cca tta gaa caa cgt gaa     192
Pro Lys Ile Gln Lys Gly Gly Asn Leu Lys Pro Leu Glu Gln Arg Glu
    50                  55                  60 cgc gct aat gtt ata tta cca aat aac gat cgt cac caa atc aca gat     240
Arg Ala Asn Val Ile Leu Pro Asn Asn Asp Arg His Gln Ile Thr Asp
65                  70                  75                  80 aca acg aat ggt cat tat gca cct gtt act tat att caa gtt gaa gca     288
Thr Thr Asn Gly His Tyr Ala Pro Val Thr Tyr Ile Gln Val Glu Ala
                85                  90                  95 cct act ggt aca ttt att gct tct ggt gta gtt gta ggt aaa gat aca     336
Pro Thr Gly Thr Phe Ile Ala Ser Gly Val Val Val Gly Lys Asp Thr
            100                 105                 110 ctt tta aca aat aaa cac gtc gta gat gct acg cac ggt gat cct cat     384
Leu Leu Thr Asn Lys His Val Val Asp Ala Thr His Gly Asp Pro His
        115                 120                 125 gct tta aaa gca ttc cct tct gca att aac caa gac aat tat cct aat     432
Ala Leu Lys Ala Phe Pro Ser Ala Ile Asn Gln Asp Asn Tyr Pro Asn
    130                 135                 140 ggt ggt ttc act gct gaa caa atc act aaa tat tca ggc gaa ggt gat     480
Gly Gly Phe Thr Ala Glu Gln Ile Thr Lys Tyr Ser Gly Glu Gly Asp
145                 150                 155                 160 tta gca atc gtt aaa ttc tcc cct aat gag caa aac aaa cat att ggc     528
Leu Ala Ile Val Lys Phe Ser Pro Asn Glu Gln Asn Lys His Ile Gly
                165                 170                 175 gaa gta gtt aaa cca gca aca atg agt aat aat gct gaa aca caa gtt     576
Glu Val Val Lys Pro Ala Thr Met Ser Asn Asn Ala Glu Thr Gln Val
            180                 185                 190 aac caa aat att act gta aca gga tat cct ggt gat aaa cct gtc gca     624
Asn Gln Asn Ile Thr Val Thr Gly Tyr Pro Gly Asp Lys Pro Val Ala
        195                 200                 205 aca atg tgg gaa agt aaa gga aaa ata acg tac tta aaa ggt gaa gca     672
Thr Met Trp Glu Ser Lys Gly Lys Ile Thr Tyr Leu Lys Gly Glu Ala
    210                 215                 220 atg caa tat gat tta agt aca act ggt ggt aac tca ggt tca cct gta     720
Met Gln Tyr Asp Leu Ser Thr Thr Gly Gly Asn Ser Gly Ser Pro Val
225                 230                 235                 240
```

-continued

| | |
|---|---|
| ttt aat gaa aaa aat gaa gtc att ggc att cat tgg ggt ggc gtt cca<br>Phe Asn Glu Lys Asn Glu Val Ile Gly Ile His Trp Gly Gly Val Pro<br>245                   250                   255 | 768 |
| aat caa ttt aac ggt gca gta ttt att aat gaa aat gta cgc aac ttc<br>Asn Gln Phe Asn Gly Ala Val Phe Ile Asn Glu Asn Val Arg Asn Phe<br>     260                   265                   270 | 816 |
| tta aaa caa aat att gaa gat atc aat ttc gca aat gat gac cac cct<br>Leu Lys Gln Asn Ile Glu Asp Ile Asn Phe Ala Asn Asp Asp His Pro<br>275                   280                   285 | 864 |
| aac aac cct gat aat cca gac aat cca aat aat ccg gac aat cct aac<br>Asn Asn Pro Asp Asn Pro Asp Asn Pro Asn Asn Pro Asp Asn Pro Asn<br>     290                   295                   300 | 912 |
| aac cct gat aac cct aac aac cct gat aat cca gac aat cct aat aat<br>Asn Pro Asp Asn Pro Asn Asn Pro Asp Asn Pro Asp Asn Pro Asn Asn<br>305                   310                   315                   320 | 960 |
| cct gat aac cct aac aac ccg gac aat cca aat aac cct gac caa cct<br>Pro Asp Asn Pro Asn Asn Pro Asp Asn Pro Asn Asn Pro Asp Gln Pro<br>                     325                   330                   335 | 1008 |
| aac aac cca aat aac ccg gac aat ggc gat aac aat aat tca gac aac<br>Asn Asn Pro Asn Asn Pro Asp Asn Gly Asp Asn Asn Asn Ser Asp Asn<br>                   340                   345                   350 | 1056 |
| cct gac gct gca<br>Pro Asp Ala Ala<br>355 | 1068 |

<210> SEQ ID NO 14
<211> LENGTH: 356
<212> TYPE: PRT
<213> ORGANISM: Staphylococcus aureus

<400> SEQUENCE: 14

Lys Gly Lys Phe Leu Lys Val Ser Ser Leu Phe Val Ala Thr Leu Thr
1               5                   10                  15

Thr Ala Thr Leu Val Ser Ser Pro Ala Ala Asn Ala Leu Ser Ser Lys
            20                  25                  30

Ala Met Asp Asn His Pro Gln Gln Thr Gln Thr Asp Lys Gln Gln Thr
        35                  40                  45

Pro Lys Ile Gln Lys Gly Gly Asn Leu Lys Pro Leu Glu Gln Arg Glu
    50                  55                  60

Arg Ala Asn Val Ile Leu Pro Asn Asn Asp Arg His Gln Ile Thr Asp
65                  70                  75                  80

Thr Thr Asn Gly His Tyr Ala Pro Val Thr Tyr Ile Gln Val Glu Ala
                85                  90                  95

Pro Thr Gly Thr Phe Ile Ala Ser Gly Val Val Gly Lys Asp Thr
            100                 105                 110

Leu Leu Thr Asn Lys His Val Val Asp Ala Thr His Gly Asp Pro His
        115                 120                 125

Ala Leu Lys Ala Phe Pro Ser Ala Ile Asn Gln Asp Asn Tyr Pro Asn
    130                 135                 140

Gly Gly Phe Thr Ala Glu Gln Ile Thr Lys Tyr Ser Gly Glu Gly Asp
145                 150                 155                 160

Leu Ala Ile Val Lys Phe Ser Pro Asn Glu Gln Asn Lys His Ile Gly
                165                 170                 175

Glu Val Val Lys Pro Ala Thr Met Ser Asn Asn Ala Glu Thr Gln Val
            180                 185                 190

Asn Gln Asn Ile Thr Val Thr Gly Tyr Pro Gly Asp Lys Pro Val Ala
        195                 200                 205

Thr Met Trp Glu Ser Lys Gly Lys Ile Thr Tyr Leu Lys Gly Glu Ala

```
                    210                 215                 220
Met Gln Tyr Asp Leu Ser Thr Thr Gly Gly Asn Ser Gly Ser Pro Val
225                 230                 235                 240

Phe Asn Glu Lys Asn Glu Val Ile Gly Ile His Trp Gly Gly Val Pro
                245                 250                 255

Asn Gln Phe Asn Gly Ala Val Phe Ile Asn Glu Asn Val Arg Asn Phe
            260                 265                 270

Leu Lys Gln Asn Ile Glu Asp Ile Asn Phe Ala Asn Asp Asp His Pro
        275                 280                 285

Asn Asn Pro Asp Asn Pro Asp Asn Pro Asn Asn Pro Asp Asn Pro Asn
    290                 295                 300

Asn Pro Asp Asn Pro Asn Asn Pro Asp Asn Pro Asp Asn Pro Asn Asn
305                 310                 315                 320

Pro Asp Asn Pro Asn Asn Pro Asp Asn Pro Asn Asn Pro Asp Gln Pro
                325                 330                 335

Asn Asn Pro Asn Asn Pro Asp Asn Gly Asp Asn Asn Asn Ser Asp Asn
            340                 345                 350

Pro Asp Ala Ala
        355

<210> SEQ ID NO 15
<211> LENGTH: 1515
<212> TYPE: DNA
<213> ORGANISM: Staphylococcus epidermidis
<220> FEATURE:
<221> NAME/KEY: CDS
<222> LOCATION: (1)..(1515)

<400> SEQUENCE: 15 atg gca aaa caa cca act gcc tta atc atc tta gat ggt ttc gca aat          48
Met Ala Lys Gln Pro Thr Ala Leu Ile Ile Leu Asp Gly Phe Ala Asn
1               5                   10                  15 cgt gaa agt gaa cat ggc aat gca gtt aag caa gca cat aaa cct aat          96
Arg Glu Ser Glu His Gly Asn Ala Val Lys Gln Ala His Lys Pro Asn
            20                  25                  30 ttt gat cga tat tat gaa aaa tat cct aca aca caa ata gaa gct agt         144
Phe Asp Arg Tyr Tyr Glu Lys Tyr Pro Thr Thr Gln Ile Glu Ala Ser
        35                  40                  45 ggc tta gat gta ggt ctt cct gaa ggt caa atg ggt aac tct gaa gta         192
Gly Leu Asp Val Gly Leu Pro Glu Gly Gln Met Gly Asn Ser Glu Val
    50                  55                  60 gga cat atg aat att ggt gca gga cgc atc gta tat caa agt tta act         240
Gly His Met Asn Ile Gly Ala Gly Arg Ile Val Tyr Gln Ser Leu Thr
65                  70                  75                  80 cgt att aat aaa tcg att gaa gac gga gaa ttc ttt gat aac act gta         288
Arg Ile Asn Lys Ser Ile Glu Asp Gly Glu Phe Phe Asp Asn Thr Val
                85                  90                  95 tta aat aac gct gtt aaa cat gtt aaa gac aat ggc tct gcg ctt cat         336
Leu Asn Asn Ala Val Lys His Val Lys Asp Asn Gly Ser Ala Leu His
            100                 105                 110 gta ttc gga ttg ctt tct gat ggt ggt gta cac agt cat tat aag cat         384
Val Phe Gly Leu Leu Ser Asp Gly Gly Val His Ser His Tyr Lys His
        115                 120                 125 cta ttt gct att tta gaa tta gct aaa aag caa gga ata gat aaa gta         432
Leu Phe Ala Ile Leu Glu Leu Ala Lys Lys Gln Gly Ile Asp Lys Val
    130                 135                 140 tat gtc cac gca ttt tta gat ggt cgt gat gtt gat caa aaa tct gct         480
Tyr Val His Ala Phe Leu Asp Gly Arg Asp Val Asp Gln Lys Ser Ala
145                 150                 155                 160
```

```
                                                  -continued ttg aaa tat ata gag gaa act gaa gat aaa ttt aaa gaa tta ggt gta       528
Leu Lys Tyr Ile Glu Glu Thr Glu Asp Lys Phe Lys Glu Leu Gly Val
            165                 170                 175 ggc caa ttc gct tct gtt tca gga cgt tat tat gct atg gac cgt gac       576
Gly Gln Phe Ala Ser Val Ser Gly Arg Tyr Tyr Ala Met Asp Arg Asp
        180                 185                 190 aag cgt tgg gat cgt gag gaa cgt gcc tat aat gct att cgt aac ttt       624
Lys Arg Trp Asp Arg Glu Glu Arg Ala Tyr Asn Ala Ile Arg Asn Phe
    195                 200                 205 gaa ggt cct aca ttt act tca gct aaa gca ggc gtt gaa gct aat tat       672
Glu Gly Pro Thr Phe Thr Ser Ala Lys Ala Gly Val Glu Ala Asn Tyr
210                 215                 220 aaa aat gat gtg act gat gaa ttc gtc gaa ccg ttt ata gtt gaa ggc       720
Lys Asn Asp Val Thr Asp Glu Phe Val Glu Pro Phe Ile Val Glu Gly
225                 230                 235                 240 caa aac gat ggt gtg aac gac gga gac gca gta atc ttt tat aat ttc       768
Gln Asn Asp Gly Val Asn Asp Gly Asp Ala Val Ile Phe Tyr Asn Phe
                245                 250                 255 cgt cca gat aga gca gct caa ctt tca gaa atc ttt act aat aaa gcg       816
Arg Pro Asp Arg Ala Ala Gln Leu Ser Glu Ile Phe Thr Asn Lys Ala
            260                 265                 270 ttt gat gga ttt aaa gtt gaa caa gtg gac aac tta ttc tac gct aca       864
Phe Asp Gly Phe Lys Val Glu Gln Val Asp Asn Leu Phe Tyr Ala Thr
        275                 280                 285 ttc acg aaa tat aat gac aat gta gat gct gaa att gta ttt gaa aaa       912
Phe Thr Lys Tyr Asn Asp Asn Val Asp Ala Glu Ile Val Phe Glu Lys
    290                 295                 300 gtt gac tta aat aat aca atc ggt gaa gtt gct caa gat aat ggc ttg       960
Val Asp Leu Asn Asn Thr Ile Gly Glu Val Ala Gln Asp Asn Gly Leu
305                 310                 315                 320 aaa caa tta cgt att gct gaa act gaa aag tat cca cat gta aca tac      1008
Lys Gln Leu Arg Ile Ala Glu Thr Glu Lys Tyr Pro His Val Thr Tyr
                325                 330                 335 ttt atg agt ggt gga cga aat gaa gag ttc gaa gga gaa cgt cgt aga      1056
Phe Met Ser Gly Gly Arg Asn Glu Glu Phe Glu Gly Glu Arg Arg Arg
            340                 345                 350 ctc atc gat tct cca aaa gta gcg act tat gat tta aaa cct gag atg      1104
Leu Ile Asp Ser Pro Lys Val Ala Thr Tyr Asp Leu Lys Pro Glu Met
        355                 360                 365 agt gca tat gaa gtt aaa gat gca tta tta gaa gag tta gac aaa ggt      1152
Ser Ala Tyr Glu Val Lys Asp Ala Leu Leu Glu Glu Leu Asp Lys Gly
    370                 375                 380 gac tta gat tta att cta ctg aac ttt gct aac cca gat atg gtt gga      1200
Asp Leu Asp Leu Ile Leu Leu Asn Phe Ala Asn Pro Asp Met Val Gly
385                 390                 395                 400 cat agt ggt atg ctt gaa cca aca att aaa gca atc gaa gca gta gat      1248
His Ser Gly Met Leu Glu Pro Thr Ile Lys Ala Ile Glu Ala Val Asp
                405                 410                 415 gag tgt ctt ggt gaa gtc gtt gac aaa att att gat atg ggt ggt cat      1296
Glu Cys Leu Gly Glu Val Val Asp Lys Ile Ile Asp Met Gly Gly His
            420                 425                 430 gcc atc atc act gca gac cac ggt aac tca gat caa gta tta act gat      1344
Ala Ile Ile Thr Ala Asp His Gly Asn Ser Asp Gln Val Leu Thr Asp
        435                 440                 445 gac gac caa cct atg acg aca cac aca act aat cct gtt cca gtt att      1392
Asp Asp Gln Pro Met Thr Thr His Thr Thr Asn Pro Val Pro Val Ile
    450                 455                 460 gta act aaa gaa ggt gtt aca tta aga gaa act gga cgt tta ggc gat      1440
Val Thr Lys Glu Gly Val Thr Leu Arg Glu Thr Gly Arg Leu Gly Asp
465                 470                 475                 480
```

```
tta gcg ccg aca tta tta gat tta tta aat gtt aaa caa cca tct gaa      1488
Leu Ala Pro Thr Leu Leu Asp Leu Leu Asn Val Lys Gln Pro Ser Glu
            485                 490                 495 atg aca ggt gaa tca ctg att aaa cat                                  1515
Met Thr Gly Glu Ser Leu Ile Lys His
        500                 505

<210> SEQ ID NO 16
<211> LENGTH: 505
<212> TYPE: PRT
<213> ORGANISM: Staphylococcus epidermidis

<400> SEQUENCE: 16

Met Ala Lys Gln Pro Thr Ala Leu Ile Ile Leu Asp Gly Phe Ala Asn
1               5                   10                  15

Arg Glu Ser Glu His Gly Asn Ala Val Lys Gln Ala His Lys Pro Asn
            20                  25                  30

Phe Asp Arg Tyr Tyr Glu Lys Tyr Pro Thr Thr Gln Ile Glu Ala Ser
        35                  40                  45

Gly Leu Asp Val Gly Leu Pro Glu Gly Gln Met Gly Asn Ser Glu Val
    50                  55                  60

Gly His Met Asn Ile Gly Ala Gly Arg Ile Val Tyr Gln Ser Leu Thr
65                  70                  75                  80

Arg Ile Asn Lys Ser Ile Glu Asp Gly Glu Phe Phe Asp Asn Thr Val
                85                  90                  95

Leu Asn Asn Ala Val Lys His Val Lys Asp Asn Gly Ser Ala Leu His
            100                 105                 110

Val Phe Gly Leu Leu Ser Asp Gly Gly Val His Ser His Tyr Lys His
        115                 120                 125

Leu Phe Ala Ile Leu Glu Leu Ala Lys Lys Gln Gly Ile Asp Lys Val
    130                 135                 140

Tyr Val His Ala Phe Leu Asp Gly Arg Asp Val Asp Gln Lys Ser Ala
145                 150                 155                 160

Leu Lys Tyr Ile Glu Glu Thr Glu Asp Lys Phe Lys Glu Leu Gly Val
                165                 170                 175

Gly Gln Phe Ala Ser Val Ser Gly Arg Tyr Tyr Ala Met Asp Arg Asp
            180                 185                 190

Lys Arg Trp Asp Arg Glu Glu Arg Ala Tyr Asn Ala Ile Arg Asn Phe
        195                 200                 205

Glu Gly Pro Thr Phe Thr Ser Ala Lys Ala Gly Val Glu Ala Asn Tyr
    210                 215                 220

Lys Asn Asp Val Thr Asp Glu Phe Val Glu Pro Phe Ile Val Glu Gly
225                 230                 235                 240

Gln Asn Asp Gly Val Asn Asp Gly Asp Ala Val Ile Phe Tyr Asn Phe
                245                 250                 255

Arg Pro Asp Arg Ala Ala Gln Leu Ser Glu Ile Phe Thr Asn Lys Ala
            260                 265                 270

Phe Asp Gly Phe Lys Val Glu Gln Val Asp Asn Leu Phe Tyr Ala Thr
        275                 280                 285

Phe Thr Lys Tyr Asn Asp Asn Val Asp Ala Glu Ile Val Phe Glu Lys
    290                 295                 300

Val Asp Leu Asn Asn Thr Ile Gly Glu Val Ala Gln Asp Asn Gly Leu
305                 310                 315                 320

Lys Gln Leu Arg Ile Ala Glu Thr Glu Lys Tyr Pro His Val Thr Tyr
                325                 330                 335

Phe Met Ser Gly Gly Arg Asn Glu Glu Phe Glu Gly Glu Arg Arg Arg
```

```
                340             345             350
Leu Ile Asp Ser Pro Lys Val Ala Thr Tyr Asp Leu Lys Pro Glu Met
            355                 360                 365

Ser Ala Tyr Glu Val Lys Asp Ala Leu Leu Glu Glu Leu Asp Lys Gly
        370                 375                 380

Asp Leu Asp Leu Ile Leu Leu Asn Phe Ala Asn Pro Asp Met Val Gly
385                 390                 395                 400

His Ser Gly Met Leu Glu Pro Thr Ile Lys Ala Ile Glu Ala Val Asp
                405                 410                 415

Glu Cys Leu Gly Glu Val Val Asp Lys Ile Ile Asp Met Gly Gly His
            420                 425                 430

Ala Ile Ile Thr Ala Asp His Gly Asn Ser Asp Gln Val Leu Thr Asp
            435                 440                 445

Asp Gln Pro Met Thr Thr His Thr Thr Asn Pro Val Pro Val Ile
            450                 455                 460

Val Thr Lys Glu Gly Val Thr Leu Arg Glu Thr Gly Arg Leu Gly Asp
465                 470                 475                 480

Leu Ala Pro Thr Leu Leu Asp Leu Leu Asn Val Lys Gln Pro Ser Glu
                485                 490                 495

Met Thr Gly Glu Ser Leu Ile Lys His
                500                 505

<210> SEQ ID NO 17
<211> LENGTH: 1176
<212> TYPE: DNA
<213> ORGANISM: Staphylococcus epidermidis
<220> FEATURE:
<221> NAME/KEY: CDS
<222> LOCATION: (1)..(1176)

<400> SEQUENCE: 17 aaa cca gat gat tca gca gaa ttt gct gct ttg gca ttt aaa gtt atg      48
Lys Pro Asp Asp Ser Ala Glu Phe Ala Ala Leu Ala Phe Lys Val Met
1               5                   10                  15 act gac cct tat gtt ggt aaa tta aca ttc ttc cgt gta tac tct gga     96
Thr Asp Pro Tyr Val Gly Lys Leu Thr Phe Phe Arg Val Tyr Ser Gly
            20                  25                  30 aca tta tct tca ggt tca tat gtg aag aac tct tct aaa gat aaa cgt    144
Thr Leu Ser Ser Gly Ser Tyr Val Lys Asn Ser Ser Lys Asp Lys Arg
        35                  40                  45 gaa cgt gtt gga cgt tta tta caa atg cac gcg aac tca cgt caa gaa    192
Glu Arg Val Gly Arg Leu Leu Gln Met His Ala Asn Ser Arg Gln Glu
    50                  55                  60 att gac act gtt tat tca ggt gaa att gca gct gca gta ggc ctt aaa    240
Ile Asp Thr Val Tyr Ser Gly Glu Ile Ala Ala Ala Val Gly Leu Lys
65                  70                  75                  80 gaa aca ggt act ggt gat act tta tgt gga gag aaa aat gac att atc    288
Glu Thr Gly Thr Gly Asp Thr Leu Cys Gly Glu Lys Asn Asp Ile Ile
                85                  90                  95 ttg gaa tca atg gaa ttc cca gaa cca gtt atc cac tta tca gtt gaa    336
Leu Glu Ser Met Glu Phe Pro Glu Pro Val Ile His Leu Ser Val Glu
            100                 105                 110 cca aaa tct aaa gct gac caa gat aaa atg act caa gct tta gtt aaa    384
Pro Lys Ser Lys Ala Asp Gln Asp Lys Met Thr Gln Ala Leu Val Lys
        115                 120                 125 tta caa gaa gaa gac cca aca ttc cat gca cac aca gat gaa gaa act    432
Leu Gln Glu Glu Asp Pro Thr Phe His Ala His Thr Asp Glu Glu Thr
    130                 135                 140 gga caa gtt atc atc ggt ggt atg ggt gaa tta cac tta gat att tta    480
Gly Gln Val Ile Ile Gly Gly Met Gly Glu Leu His Leu Asp Ile Leu
```

```
Gly Gln Val Ile Ile Gly Gly Met Gly Glu Leu His Leu Asp Ile Leu
145                 150                 155                 160 gtt gac cgt atg aag aaa gaa ttc aac gtt gaa tgt aac gta ggt gct      528
Val Asp Arg Met Lys Lys Glu Phe Asn Val Glu Cys Asn Val Gly Ala
                165                 170                 175 cca atg gtt tct tat cgt gaa aca ttt aaa caa cct gca caa gtt caa      576
Pro Met Val Ser Tyr Arg Glu Thr Phe Lys Gln Pro Ala Gln Val Gln
            180                 185                 190 ggt aaa ttc tca cgt caa tct ggt ggt cgt ggt caa tat ggt gat gtt      624
Gly Lys Phe Ser Arg Gln Ser Gly Gly Arg Gly Gln Tyr Gly Asp Val
        195                 200                 205 cat att gaa ttc act cct aac gaa aca ggt ggc ggt ttc gaa ttc gaa      672
His Ile Glu Phe Thr Pro Asn Glu Thr Gly Gly Gly Phe Glu Phe Glu
    210                 215                 220 aac gct att gtt ggt ggt gta gtt cct cgt gaa tac att cca tca gtt      720
Asn Ala Ile Val Gly Gly Val Val Pro Arg Glu Tyr Ile Pro Ser Val
225                 230                 235                 240 gaa caa ggt ctt aaa gat gct atg gaa aat ggt gtc tta gct ggt tat      768
Glu Gln Gly Leu Lys Asp Ala Met Glu Asn Gly Val Leu Ala Gly Tyr
                245                 250                 255 cca tta att gat gtt aaa gct aaa tta ttt gat ggt tct tat cat gat      816
Pro Leu Ile Asp Val Lys Ala Lys Leu Phe Asp Gly Ser Tyr His Asp
            260                 265                 270 gtc gat tca tct gaa atg gcc ttc aaa att gct gca tca tta gcg ctt      864
Val Asp Ser Ser Glu Met Ala Phe Lys Ile Ala Ala Ser Leu Ala Leu
        275                 280                 285 aaa gaa gct gct aaa aaa tgt gat cca gtt atc tta gaa cca atg atg      912
Lys Glu Ala Ala Lys Lys Cys Asp Pro Val Ile Leu Glu Pro Met Met
    290                 295                 300 aaa gtt act atc gaa atg cct gaa gaa tat atg ggt gat atc atg ggt      960
Lys Val Thr Ile Glu Met Pro Glu Glu Tyr Met Gly Asp Ile Met Gly
305                 310                 315                 320 gac gtg act gct cgt cgt gga cgt gta gac ggt atg gaa cca cgt ggt     1008
Asp Val Thr Ala Arg Arg Gly Arg Val Asp Gly Met Glu Pro Arg Gly
                325                 330                 335 aat gct caa gtt gtt aac gca tat gta cca ctt tca gaa atg ttt ggt     1056
Asn Ala Gln Val Val Asn Ala Tyr Val Pro Leu Ser Glu Met Phe Gly
            340                 345                 350 tat gca act tca tta cgt tct aac acg caa ggt cgc ggt act tac aca     1104
Tyr Ala Thr Ser Leu Arg Ser Asn Thr Gln Gly Arg Gly Thr Tyr Thr
        355                 360                 365 atg tac ttt gac cac tat gca gaa gtt cct aaa tca att gct gaa gaa     1152
Met Tyr Phe Asp His Tyr Ala Glu Val Pro Lys Ser Ile Ala Glu Glu
    370                 375                 380 atc atc aag aaa aat aaa ggt gaa                                     1176
Ile Ile Lys Lys Asn Lys Gly Glu
385                 390

<210> SEQ ID NO 18
<211> LENGTH: 392
<212> TYPE: PRT
<213> ORGANISM: Staphylococcus epidermidis

<400> SEQUENCE: 18

Lys Pro Asp Asp Ser Ala Glu Phe Ala Ala Leu Ala Phe Lys Val Met
1               5                   10                  15

Thr Asp Pro Tyr Val Gly Lys Leu Thr Phe Phe Arg Val Tyr Ser Gly
            20                  25                  30

Thr Leu Ser Ser Gly Ser Tyr Val Lys Asn Ser Ser Lys Asp Lys Arg
        35                  40                  45
```

```
Glu Arg Val Gly Arg Leu Leu Gln Met His Ala Asn Ser Arg Gln Glu
 50                  55                  60

Ile Asp Thr Val Tyr Ser Gly Glu Ile Ala Ala Val Gly Leu Lys
 65                  70                  75                  80

Glu Thr Gly Thr Gly Asp Thr Leu Cys Gly Glu Lys Asn Asp Ile Ile
                     85                  90                  95

Leu Glu Ser Met Glu Phe Pro Glu Pro Val Ile His Leu Ser Val Glu
                100                 105                 110

Pro Lys Ser Lys Ala Asp Gln Asp Lys Met Thr Gln Ala Leu Val Lys
                115                 120                 125

Leu Gln Glu Glu Asp Pro Thr Phe His Ala His Thr Asp Glu Glu Thr
            130                 135                 140

Gly Gln Val Ile Ile Gly Gly Met Gly Glu Leu His Leu Asp Ile Leu
145                 150                 155                 160

Val Asp Arg Met Lys Lys Glu Phe Asn Val Glu Cys Asn Val Gly Ala
                165                 170                 175

Pro Met Val Ser Tyr Arg Glu Thr Phe Lys Gln Pro Ala Gln Val Gln
                180                 185                 190

Gly Lys Phe Ser Arg Gln Ser Gly Arg Gly Gln Tyr Gly Asp Val
                195                 200                 205

His Ile Glu Phe Thr Pro Asn Glu Thr Gly Gly Phe Glu Phe Glu
210                 215                 220

Asn Ala Ile Val Gly Gly Val Val Pro Arg Glu Tyr Ile Pro Ser Val
225                 230                 235                 240

Glu Gln Gly Leu Lys Asp Ala Met Glu Asn Gly Val Leu Ala Gly Tyr
                245                 250                 255

Pro Leu Ile Asp Val Lys Ala Lys Leu Phe Asp Gly Ser Tyr His Asp
                260                 265                 270

Val Asp Ser Ser Glu Met Ala Phe Lys Ile Ala Ala Ser Leu Ala Leu
                275                 280                 285

Lys Glu Ala Ala Lys Lys Cys Asp Pro Val Ile Leu Glu Pro Met Met
                290                 295                 300

Lys Val Thr Ile Glu Met Pro Glu Glu Tyr Met Gly Asp Ile Met Gly
305                 310                 315                 320

Asp Val Thr Ala Arg Arg Gly Arg Val Asp Gly Met Glu Pro Arg Gly
                325                 330                 335

Asn Ala Gln Val Val Asn Ala Tyr Val Pro Leu Ser Glu Met Phe Gly
                340                 345                 350

Tyr Ala Thr Ser Leu Arg Ser Asn Thr Gln Gly Arg Gly Thr Tyr Thr
                355                 360                 365

Met Tyr Phe Asp His Tyr Ala Glu Val Pro Lys Ser Ile Ala Glu Glu
                370                 375                 380

Ile Ile Lys Lys Asn Lys Gly Glu
385                 390

<210> SEQ ID NO 19
<211> LENGTH: 1230
<212> TYPE: DNA
<213> ORGANISM: Staphylococcus aureus
<220> FEATURE:
<221> NAME/KEY: CDS
<222> LOCATION: (1)..(1230)

<400> SEQUENCE: 19 gta caa gga ccc att caa gta aat agt gaa ata ggc aaa ttg aaa act    48
Val Gln Gly Pro Ile Gln Val Asn Ser Glu Ile Gly Lys Leu Lys Thr
 1               5                  10                  15
```

| | | |
|---|---|---|
| gtg ttg tta aaa aga cca gga aaa gaa tta gaa aat tta gta cct gat<br>Val Leu Leu Lys Arg Pro Gly Lys Glu Leu Glu Asn Leu Val Pro Asp<br>         20                   25                 30 | | 96 |
| cat tta agt ggt tta tta ttc gat gat att ccc tac tta aaa gtt gca<br>His Leu Ser Gly Leu Leu Phe Asp Asp Ile Pro Tyr Leu Lys Val Ala<br>              35                40               45 | | 144 |
| caa gaa gag cat gac aaa ttt gct caa act ttg aga gat gaa gga atc<br>Gln Glu Glu His Asp Lys Phe Ala Gln Thr Leu Arg Asp Glu Gly Ile<br>50                    55                60 | | 192 |
| gaa gta gtt tat tta gaa aaa ctt gca gca gaa tct att act gag cca<br>Glu Val Val Tyr Leu Glu Lys Leu Ala Ala Glu Ser Ile Thr Glu Pro<br>65                   70              75               80 | | 240 |
| gaa gta cgc gag aac ttc ata aac gat ata tta aca gaa tct aaa aag<br>Glu Val Arg Glu Asn Phe Ile Asn Asp Ile Leu Thr Glu Ser Lys Lys<br>                  85                90             95 | | 288 |
| aca ata tta ggt cat gaa act gaa att aaa gaa ttc ttt tca aag tta<br>Thr Ile Leu Gly His Glu Thr Glu Ile Lys Glu Phe Phe Ser Lys Leu<br>               100               105             110 | | 336 |
| tct gac caa gaa ctt gta aat aaa atc atg gct ggc ata cgt aaa gaa<br>Ser Asp Gln Glu Leu Val Asn Lys Ile Met Ala Gly Ile Arg Lys Glu<br>              115                120              125 | | 384 |
| gaa att caa ctt gaa aca act cat tta gta gaa tat atg gat gat aga<br>Glu Ile Gln Leu Glu Thr Thr His Leu Val Glu Tyr Met Asp Asp Arg<br>130                   135               140 | | 432 |
| tat cca ttt tac tta gat cca atg ccc aac ctt tat ttt aca aga gat<br>Tyr Pro Phe Tyr Leu Asp Pro Met Pro Asn Leu Tyr Phe Thr Arg Asp<br>145                   150               155             160 | | 480 |
| ccc caa gct tca att ggt aga gga atg aca att aac aga atg tat tgg<br>Pro Gln Ala Ser Ile Gly Arg Gly Met Thr Ile Asn Arg Met Tyr Trp<br>                  165               170             175 | | 528 |
| aga gca cga cgt aga gaa tct att ttt atg aca tat ata ctg aaa cat<br>Arg Ala Arg Arg Arg Glu Ser Ile Phe Met Thr Tyr Ile Leu Lys His<br>              180               185             190 | | 576 |
| cat cca aga ttt aaa gat aaa gat gta cca gta tgg tta gat cgt aac<br>His Pro Arg Phe Lys Asp Lys Asp Val Pro Val Trp Leu Asp Arg Asn<br>               195               200             205 | | 624 |
| tca cca ttt aat att gaa ggt gga gat gaa tta gta tta tcg aaa gat<br>Ser Pro Phe Asn Ile Glu Gly Gly Asp Glu Leu Val Leu Ser Lys Asp<br>210                   215               220 | | 672 |
| gtt tta gct att ggt ata tca gaa cgt aca tca gct caa gca ata gaa<br>Val Leu Ala Ile Gly Ile Ser Glu Arg Thr Ser Ala Gln Ala Ile Glu<br>225                   230               235             240 | | 720 |
| aag tta gca cgt aat att ttc aaa gat gca aac aca agt ttt aaa aaa<br>Lys Leu Ala Arg Asn Ile Phe Lys Asp Ala Asn Thr Ser Phe Lys Lys<br>                  245               250             255 | | 768 |
| atc gta gct att gaa ata cct aat aca cgc aca ttt atg cac cta gat<br>Ile Val Ala Ile Glu Ile Pro Asn Thr Arg Thr Phe Met His Leu Asp<br>              260               265             270 | | 816 |
| aca gta cta act atg att gac tac gat aag ttt aca gta cat gca gca<br>Thr Val Leu Thr Met Ile Asp Tyr Asp Lys Phe Thr Val His Ala Ala<br>              275               280             285 | | 864 |
| ata ttt aaa gaa gaa aat aat atg aat ata ttt acc ata gaa caa aat<br>Ile Phe Lys Glu Glu Asn Asn Met Asn Ile Phe Thr Ile Glu Gln Asn<br>290                   295               300 | | 912 |
| gat ggt aag gac gat ata aaa att act cgt tct agc aag tta cgt gaa<br>Asp Gly Lys Asp Asp Ile Lys Ile Thr Arg Ser Ser Lys Leu Arg Glu<br>305                   310               315             320 | | 960 |
| aca ctt gct gaa gtt tta gaa gta gaa aaa gtg gac ttt att cca aca<br>Thr Leu Ala Glu Val Leu Glu Val Glu Lys Val Asp Phe Ile Pro Thr<br>                  325               330             335 | | 1008 |

```
ggt aat ggc gac gtt att gat ggt gca cgt gaa caa tgg aat gat ggc    1056
Gly Asn Gly Asp Val Ile Asp Gly Ala Arg Glu Gln Trp Asn Asp Gly
        340                 345                 350 tca aac aca tta tgt att cga cca ggg gtt gtg gtg aca tac gat cgc    1104
Ser Asn Thr Leu Cys Ile Arg Pro Gly Val Val Val Thr Tyr Asp Arg
            355                 360                 365 aac tat gta tca aac caa ctt tta cgc gac aaa gga att aaa gtg att    1152
Asn Tyr Val Ser Asn Gln Leu Leu Arg Asp Lys Gly Ile Lys Val Ile
370                 375                 380 gaa att act ggt agt gaa ctt gta cgt gga cgc gga ggc cca aga tgt    1200
Glu Ile Thr Gly Ser Glu Leu Val Arg Gly Arg Gly Gly Pro Arg Cys
385                 390                 395                 400 atg agt cag ccg tta ttt aga gaa gat att                            1230
Met Ser Gln Pro Leu Phe Arg Glu Asp Ile
                405                 410

<210> SEQ ID NO 20
<211> LENGTH: 410
<212> TYPE: PRT
<213> ORGANISM: Staphylococcus aureus

<400> SEQUENCE: 20

Val Gln Gly Pro Ile Gln Val Asn Ser Glu Ile Gly Lys Leu Lys Thr
1               5                   10                  15

Val Leu Leu Lys Arg Pro Gly Lys Glu Leu Glu Asn Leu Val Pro Asp
            20                  25                  30

His Leu Ser Gly Leu Leu Phe Asp Asp Ile Pro Tyr Leu Lys Val Ala
        35                  40                  45

Gln Glu Glu His Asp Lys Phe Ala Gln Thr Leu Arg Asp Glu Gly Ile
    50                  55                  60

Glu Val Val Tyr Leu Glu Lys Leu Ala Ala Glu Ser Ile Thr Glu Pro
65                  70                  75                  80

Glu Val Arg Glu Asn Phe Ile Asn Asp Ile Leu Thr Glu Ser Lys Lys
                85                  90                  95

Thr Ile Leu Gly His Glu Thr Glu Ile Lys Glu Phe Phe Ser Lys Leu
            100                 105                 110

Ser Asp Gln Glu Leu Val Asn Lys Ile Met Ala Gly Ile Arg Lys Glu
        115                 120                 125

Glu Ile Gln Leu Glu Thr Thr His Leu Val Glu Tyr Met Asp Asp Arg
    130                 135                 140

Tyr Pro Phe Tyr Leu Asp Pro Met Pro Asn Leu Tyr Phe Thr Arg Asp
145                 150                 155                 160

Pro Gln Ala Ser Ile Gly Arg Gly Met Thr Ile Asn Arg Met Tyr Trp
                165                 170                 175

Arg Ala Arg Arg Arg Glu Ser Ile Phe Met Thr Tyr Ile Leu Lys His
            180                 185                 190

His Pro Arg Phe Lys Asp Lys Asp Val Pro Val Trp Leu Asp Arg Asn
        195                 200                 205

Ser Pro Phe Asn Ile Glu Gly Gly Asp Glu Leu Val Leu Ser Lys Asp
    210                 215                 220

Val Leu Ala Ile Gly Ile Ser Glu Arg Thr Ser Ala Gln Ala Ile Glu
225                 230                 235                 240

Lys Leu Ala Arg Asn Ile Phe Lys Asp Ala Asn Thr Ser Phe Lys Lys
                245                 250                 255

Ile Val Ala Ile Glu Ile Pro Asn Thr Arg Thr Phe Met His Leu Asp
            260                 265                 270
```

```
Thr Val Leu Thr Met Ile Asp Tyr Asp Lys Phe Thr Val His Ala Ala
        275                 280                 285
Ile Phe Lys Glu Glu Asn Asn Met Asn Ile Phe Thr Ile Glu Gln Asn
    290                 295                 300
Asp Gly Lys Asp Asp Ile Lys Ile Thr Arg Ser Ser Lys Leu Arg Glu
305                 310                 315                 320
Thr Leu Ala Glu Val Leu Glu Val Glu Lys Val Asp Phe Ile Pro Thr
                325                 330                 335
Gly Asn Gly Asp Val Ile Asp Gly Ala Arg Glu Gln Trp Asn Asp Gly
                340                 345                 350
Ser Asn Thr Leu Cys Ile Arg Pro Gly Val Val Thr Tyr Asp Arg
                355                 360                 365
Asn Tyr Val Ser Asn Gln Leu Leu Arg Asp Lys Gly Ile Lys Val Ile
    370                 375                 380
Glu Ile Thr Gly Ser Glu Leu Val Arg Gly Arg Gly Pro Arg Cys
385                 390                 395                 400
Met Ser Gln Pro Leu Phe Arg Glu Asp Ile
405                 410

<210> SEQ ID NO 21
<211> LENGTH: 867
<212> TYPE: DNA
<213> ORGANISM: Staphylococcus epidermidis
<220> FEATURE:
<221> NAME/KEY: CDS
<222> LOCATION: (1)..(867)

<400> SEQUENCE: 21 caa caa gca agt gca aca agt tct aaa act tca gaa aat cca gca acg      48
Gln Gln Ala Ser Ala Thr Ser Ser Lys Thr Ser Glu Asn Pro Ala Thr
1               5                   10                  15 att gaa gaa gta tta ggt ctt agt caa gcc att tac gat aca aaa aat      96
Ile Glu Glu Val Leu Gly Leu Ser Gln Ala Ile Tyr Asp Thr Lys Asn
                20                  25                  30 gca tta aat ggt gaa caa cga ctt gca act gag aag agc aaa gat cta     144
Ala Leu Asn Gly Glu Gln Arg Leu Ala Thr Glu Lys Ser Lys Asp Leu
            35                  40                  45 aaa tta ata aaa gga tta aaa gat tta aat aaa gca caa ctt gaa gat     192
Lys Leu Ile Lys Gly Leu Lys Asp Leu Asn Lys Ala Gln Leu Glu Asp
    50                  55                  60 gtc aca aac aag gta aat tca gca aat act tta aca gag tta tct cag     240
Val Thr Asn Lys Val Asn Ser Ala Asn Thr Leu Thr Glu Leu Ser Gln
65                  70                  75                  80 ctc act caa tca acg tta gaa tta aac gat aaa atg aaa tta ttg aga     288
Leu Thr Gln Ser Thr Leu Glu Leu Asn Asp Lys Met Lys Leu Leu Arg
                85                  90                  95 gat aag ctt aaa act tta gta aat cct gtt aaa gca agt tta aat tat     336
Asp Lys Leu Lys Thr Leu Val Asn Pro Val Lys Ala Ser Leu Asn Tyr
                100                 105                 110 aga aac gct gat tat aat tta aaa cgt caa ttt aac aaa gct tta aaa     384
Arg Asn Ala Asp Tyr Asn Leu Lys Arg Gln Phe Asn Lys Ala Leu Lys
            115                 120                 125 gaa gct aaa ggc gta tta aat aaa aat agc ggt aca aat gtc aat atc     432
Glu Ala Lys Gly Val Leu Asn Lys Asn Ser Gly Thr Asn Val Asn Ile
    130                 135                 140 aat gac att caa cat ctt tta aca caa ata gat aat gct aaa gac caa     480
Asn Asp Ile Gln His Leu Leu Thr Gln Ile Asp Asn Ala Lys Asp Gln
145                 150                 155                 160 tta aat ggt gaa cga cgt cta aaa gaa cat caa caa aaa tct gaa gta     528
Leu Asn Gly Glu Arg Arg Leu Lys Glu His Gln Gln Lys Ser Glu Val
```

```
                        165                 170                 175
ttt att att aaa gaa tta gat ata ctt aat aat gct caa aaa gct gca       576
Phe Ile Ile Lys Glu Leu Asp Ile Leu Asn Asn Ala Gln Lys Ala Ala
            180                 185                 190 ata att aat cag att aga gcg tct aaa gac att aaa ata att aat caa       624
Ile Ile Asn Gln Ile Arg Ala Ser Lys Asp Ile Lys Ile Ile Asn Gln
        195                 200                 205 atc gtt gat aat gca ata gaa tta aat gat gct atg caa ggt tta aaa       672
Ile Val Asp Asn Ala Ile Glu Leu Asn Asp Ala Met Gln Gly Leu Lys
    210                 215                 220 gaa cat gta gct caa tta aca gca act aca aaa gac aac att gaa tat       720
Glu His Val Ala Gln Leu Thr Ala Thr Thr Lys Asp Asn Ile Glu Tyr
225                 230                 235                 240 tta aat gct gat gaa gac cat aaa tta caa tat gat tac gct atc aac       768
Leu Asn Ala Asp Glu Asp His Lys Leu Gln Tyr Asp Tyr Ala Ile Asn
                245                 250                 255 tta gcg aat aat gtt ctt gac aaa gaa aac ggt aca aat aaa gac gct       816
Leu Ala Asn Asn Val Leu Asp Lys Glu Asn Gly Thr Asn Lys Asp Ala
            260                 265                 270 aat atc ata att gga atg att caa aac atg gat gat gct aga gca ctt       864
Asn Ile Ile Ile Gly Met Ile Gln Asn Met Asp Asp Ala Arg Ala Leu
        275                 280                 285 cta                                                                   867
Leu

<210> SEQ ID NO 22
<211> LENGTH: 289
<212> TYPE: PRT
<213> ORGANISM: Staphylococcus epidermidis

<400> SEQUENCE: 22

Gln Gln Ala Ser Ala Thr Ser Ser Lys Thr Ser Glu Asn Pro Ala Thr
1               5                   10                  15

Ile Glu Glu Val Leu Gly Leu Ser Gln Ala Ile Tyr Asp Thr Lys Asn
            20                  25                  30

Ala Leu Asn Gly Glu Gln Arg Leu Ala Thr Glu Lys Ser Lys Asp Leu
        35                  40                  45

Lys Leu Ile Lys Gly Leu Lys Asp Leu Asn Lys Ala Gln Leu Glu Asp
    50                  55                  60

Val Thr Asn Lys Val Asn Ser Ala Asn Thr Leu Thr Glu Leu Ser Gln
65                  70                  75                  80

Leu Thr Gln Ser Thr Leu Glu Leu Asn Asp Lys Met Lys Leu Leu Arg
                85                  90                  95

Asp Lys Leu Lys Thr Leu Val Asn Pro Val Lys Ala Ser Leu Asn Tyr
            100                 105                 110

Arg Asn Ala Asp Tyr Asn Leu Lys Arg Gln Phe Asn Lys Ala Leu Lys
        115                 120                 125

Glu Ala Lys Gly Val Leu Asn Lys Asn Ser Gly Thr Asn Val Asn Ile
    130                 135                 140

Asn Asp Ile Gln His Leu Leu Thr Gln Ile Asp Asn Ala Lys Asp Gln
145                 150                 155                 160

Leu Asn Gly Glu Arg Arg Leu Lys Glu His Gln Gln Lys Ser Glu Val
                165                 170                 175

Phe Ile Ile Lys Glu Leu Asp Ile Leu Asn Asn Ala Gln Lys Ala Ala
            180                 185                 190

Ile Ile Asn Gln Ile Arg Ala Ser Lys Asp Ile Lys Ile Ile Asn Gln
        195                 200                 205
```

```
Ile Val Asp Asn Ala Ile Glu Leu Asn Asp Ala Met Gln Gly Leu Lys
            210                 215                 220

Glu His Val Ala Gln Leu Thr Ala Thr Thr Lys Asp Asn Ile Glu Tyr
225                 230                 235                 240

Leu Asn Ala Asp Glu Asp His Lys Leu Gln Tyr Asp Tyr Ala Ile Asn
                245                 250                 255

Leu Ala Asn Asn Val Leu Asp Lys Glu Asn Gly Thr Asn Lys Asp Ala
            260                 265                 270

Asn Ile Ile Ile Gly Met Ile Gln Asn Met Asp Asp Ala Arg Ala Leu
            275                 280                 285

Leu
```

<210> SEQ ID NO 23
<211> LENGTH: 621
<212> TYPE: DNA
<213> ORGANISM: Staphylococcus epidermidis
<220> FEATURE:
<221> NAME/KEY: CDS
<222> LOCATION: (1)..(621)

<400> SEQUENCE: 23

```
tca gaa act aca aac gtt gat aaa gca cac tta gta gat tta gca caa      48
Ser Glu Thr Thr Asn Val Asp Lys Ala His Leu Val Asp Leu Ala Gln
1               5                   10                  15 cat aat cct gaa gaa tta aat gct aaa cca gtt caa gct ggt gct tac      96
His Asn Pro Glu Glu Leu Asn Ala Lys Pro Val Gln Ala Gly Ala Tyr
            20                  25                  30 gat att cat ttc gta gac aat gga tac caa tac aac ttc act tca aat     144
Asp Ile His Phe Val Asp Asn Gly Tyr Gln Tyr Asn Phe Thr Ser Asn
        35                  40                  45 ggt tct gaa tgg tca tgg agc tac gct gta gct ggt tca gat gct gat     192
Gly Ser Glu Trp Ser Trp Ser Tyr Ala Val Ala Gly Ser Asp Ala Asp
50                  55                  60 tac aca gaa tca tca tca aac caa gaa gta agt gca aat aca caa tct     240
Tyr Thr Glu Ser Ser Ser Asn Gln Glu Val Ser Ala Asn Thr Gln Ser
65                  70                  75                  80 agt aac aca aat gta caa gct gtt tca gct cca act tct tca gaa agt     288
Ser Asn Thr Asn Val Gln Ala Val Ser Ala Pro Thr Ser Ser Glu Ser
                85                  90                  95 cgt agc tac agc aca tca act act tca tac tca gca cca agc cat aac     336
Arg Ser Tyr Ser Thr Ser Thr Thr Ser Tyr Ser Ala Pro Ser His Asn
            100                 105                 110 tac agc tct cac agt agt tca gta aga tta tca aat ggt aat act gct     384
Tyr Ser Ser His Ser Ser Ser Val Arg Leu Ser Asn Gly Asn Thr Ala
        115                 120                 125 ggt tct gta ggt tca tat gct gct gct caa atg gct gca cgt act ggt     432
Gly Ser Val Gly Ser Tyr Ala Ala Ala Gln Met Ala Ala Arg Thr Gly
130                 135                 140 gta tct gct tca aca tgg gaa cac atc att gct aga gaa tca aat ggt     480
Val Ser Ala Ser Thr Trp Glu His Ile Ile Ala Arg Glu Ser Asn Gly
145                 150                 155                 160 caa tta cat gca cgt aat gct tca ggt gct gct gga tta ttc caa act     528
Gln Leu His Ala Arg Asn Ala Ser Gly Ala Ala Gly Leu Phe Gln Thr
                165                 170                 175 atg cca ggt tgg ggt tca act ggt tca gta aat gat caa atc aat gcc     576
Met Pro Gly Trp Gly Ser Thr Gly Ser Val Asn Asp Gln Ile Asn Ala
            180                 185                 190 gct tat aaa gca tat aaa gca caa ggt tta tct gct tgg ggt atg          621
Ala Tyr Lys Ala Tyr Lys Ala Gln Gly Leu Ser Ala Trp Gly Met
        195                 200                 205
```

<210> SEQ ID NO 24
<211> LENGTH: 207
<212> TYPE: PRT
<213> ORGANISM: Staphylococcus epidermidis

<400> SEQUENCE: 24

Ser Glu Thr Thr Asn Val Asp Lys Ala His Leu Val Asp Leu Ala Gln
1               5                   10                  15

His Asn Pro Glu Glu Leu Asn Ala Lys Pro Val Gln Ala Gly Ala Tyr
            20                  25                  30

Asp Ile His Phe Val Asp Asn Gly Tyr Gln Tyr Asn Phe Thr Ser Asn
        35                  40                  45

Gly Ser Glu Trp Ser Trp Ser Tyr Ala Val Ala Gly Ser Asp Ala Asp
    50                  55                  60

Tyr Thr Glu Ser Ser Ser Asn Gln Glu Val Ser Ala Asn Thr Gln Ser
65                  70                  75                  80

Ser Asn Thr Asn Val Gln Ala Val Ser Ala Pro Thr Ser Ser Glu Ser
                85                  90                  95

Arg Ser Tyr Ser Thr Ser Thr Thr Ser Tyr Ser Ala Pro Ser His Asn
            100                 105                 110

Tyr Ser Ser His Ser Ser Ser Val Arg Leu Ser Asn Gly Asn Thr Ala
        115                 120                 125

Gly Ser Val Gly Ser Tyr Ala Ala Ala Gln Met Ala Ala Arg Thr Gly
    130                 135                 140

Val Ser Ala Ser Thr Trp Glu His Ile Ile Ala Arg Glu Ser Asn Gly
145                 150                 155                 160

Gln Leu His Ala Arg Asn Ala Ser Gly Ala Ala Gly Leu Phe Gln Thr
                165                 170                 175

Met Pro Gly Trp Gly Ser Thr Gly Ser Val Asn Asp Gln Ile Asn Ala
            180                 185                 190

Ala Tyr Lys Ala Tyr Lys Ala Gln Gly Leu Ser Ala Trp Gly Met
        195                 200                 205

<210> SEQ ID NO 25
<211> LENGTH: 456
<212> TYPE: DNA
<213> ORGANISM: Staphylococcus aureus
<220> FEATURE:
<221> NAME/KEY: CDS
<222> LOCATION: (1)..(456)

<400> SEQUENCE: 25 aag aag aaa tca cca ggt aca tta gcg gaa aat cgt aaa gca aga cat      48
Lys Lys Lys Ser Pro Gly Thr Leu Ala Glu Asn Arg Lys Ala Arg His
1               5                   10                  15 gat tat aat att gaa gat acg att gaa gcg gga atc gta tta caa ggt      96
Asp Tyr Asn Ile Glu Asp Thr Ile Glu Ala Gly Ile Val Leu Gln Gly
            20                  25                  30 aca gaa ata aaa tcg att cgc cga ggt agt gct aac ctt aaa gat agt     144
Thr Glu Ile Lys Ser Ile Arg Arg Gly Ser Ala Asn Leu Lys Asp Ser
        35                  40                  45 tac gcg caa gtt aaa aac ggt gaa atg tat ttg aat aat atg cat ata     192
Tyr Ala Gln Val Lys Asn Gly Glu Met Tyr Leu Asn Asn Met His Ile
    50                  55                  60 gca cca tac gaa gaa ggg aat cgt ttt aat cac gat cct ctt cgt tct     240
Ala Pro Tyr Glu Glu Gly Asn Arg Phe Asn His Asp Pro Leu Arg Ser
65                  70                  75                  80 cga aaa tta tta ttg cat aaa cgt gaa atc ttt aaa tta ggt gaa caa     288
Arg Lys Leu Leu Leu His Lys Arg Glu Ile Phe Lys Leu Gly Glu Gln

```
                      85                  90                  95
act cga gaa att ggt tat tcg att gtg ccg tta aag ctt tat ttg aag      336
Thr Arg Glu Ile Gly Tyr Ser Ile Val Pro Leu Lys Leu Tyr Leu Lys
            100                 105                 110 cat gga cat tgt aaa gta tta ctt ggt gtt gca cga ggt aag aaa aaa      384
His Gly His Cys Lys Val Leu Leu Gly Val Ala Arg Gly Lys Lys Lys
            115                 120                 125 tat gat aaa cgt caa gct ttg aaa gaa aaa gca gtc aaa cga gat gtt      432
Tyr Asp Lys Arg Gln Ala Leu Lys Glu Lys Ala Val Lys Arg Asp Val
130                 135                 140 gcg cgc gat atg aaa gcc cgt tat                                      456
Ala Arg Asp Met Lys Ala Arg Tyr
145                 150

<210> SEQ ID NO 26
<211> LENGTH: 152
<212> TYPE: PRT
<213> ORGANISM: Staphylococcus aureus

<400> SEQUENCE: 26

Lys Lys Lys Ser Pro Gly Thr Leu Ala Glu Asn Arg Lys Ala Arg His
1               5                   10                  15

Asp Tyr Asn Ile Glu Asp Thr Ile Glu Ala Gly Ile Val Leu Gln Gly
            20                  25                  30

Thr Glu Ile Lys Ser Ile Arg Arg Gly Ser Ala Asn Leu Lys Asp Ser
        35                  40                  45

Tyr Ala Gln Val Lys Asn Gly Glu Met Tyr Leu Asn Asn Met His Ile
    50                  55                  60

Ala Pro Tyr Glu Glu Gly Asn Arg Phe Asn His Asp Pro Leu Arg Ser
65                  70                  75                  80

Arg Lys Leu Leu Leu His Lys Arg Glu Ile Phe Lys Leu Gly Glu Gln
                85                  90                  95

Thr Arg Glu Ile Gly Tyr Ser Ile Val Pro Leu Lys Leu Tyr Leu Lys
            100                 105                 110

His Gly His Cys Lys Val Leu Leu Gly Val Ala Arg Gly Lys Lys Lys
        115                 120                 125

Tyr Asp Lys Arg Gln Ala Leu Lys Glu Lys Ala Val Lys Arg Asp Val
130                 135                 140

Ala Arg Asp Met Lys Ala Arg Tyr
145                 150

<210> SEQ ID NO 27
<211> LENGTH: 1932
<212> TYPE: DNA
<213> ORGANISM: Staphylococcus aureus
<220> FEATURE:
<221> NAME/KEY: CDS
<222> LOCATION: (1)..(1932)

<400> SEQUENCE: 27 tcc aaa gat aaa gaa att aat aat act att gat gca att gaa gat aaa      48
Ser Lys Asp Lys Glu Ile Asn Asn Thr Ile Asp Ala Ile Glu Asp Lys
1               5                   10                  15 aat ttc aaa caa gtt tat aaa gat agc agt tat att tct aaa agc gat      96
Asn Phe Lys Gln Val Tyr Lys Asp Ser Ser Tyr Ile Ser Lys Ser Asp
            20                  25                  30 aat ggt gaa gta gaa atg act gaa cgt ccg ata aaa ata tat aat agt     144
Asn Gly Glu Val Glu Met Thr Glu Arg Pro Ile Lys Ile Tyr Asn Ser
        35                  40                  45 tta ggc gtt aaa gat ata aac att cag gat cgt aaa ata aaa aaa gta     192
```

```
                Leu Gly Val Lys Asp Ile Asn Ile Gln Asp Arg Lys Ile Lys Lys Val
                     50                  55                  60 tct aaa aat aaa aaa cga gta gat gct caa tat aaa att aaa aca aac           240
Ser Lys Asn Lys Lys Arg Val Asp Ala Gln Tyr Lys Ile Lys Thr Asn
 65                  70                  75                  80 tac ggt aac att gat cgc aac gtt caa ttt aat ttt gtt aaa gaa gat           288
Tyr Gly Asn Ile Asp Arg Asn Val Gln Phe Asn Phe Val Lys Glu Asp
                     85                  90                  95 ggt atg tgg aag tta gat tgg gat cat agc gtc att att cca gga atg           336
Gly Met Trp Lys Leu Asp Trp Asp His Ser Val Ile Ile Pro Gly Met
                100                 105                 110 cag aaa gac caa agc ata cat att gaa aat tta aaa tca gaa cgt ggt           384
Gln Lys Asp Gln Ser Ile His Ile Glu Asn Leu Lys Ser Glu Arg Gly
                115                 120                 125 aaa att tta gac cga aac aat gtg gaa ttg gcc aat aca gga aca gca           432
Lys Ile Leu Asp Arg Asn Asn Val Glu Leu Ala Asn Thr Gly Thr Ala
        130                 135                 140 tat gag ata ggc atc gtt cca aag aat gta tct aaa aaa gat tat aaa           480
Tyr Glu Ile Gly Ile Val Pro Lys Asn Val Ser Lys Lys Asp Tyr Lys
145                 150                 155                 160 gca atc gct aaa gaa cta agt att tct gaa gac tat atc aaa caa caa           528
Ala Ile Ala Lys Glu Leu Ser Ile Ser Glu Asp Tyr Ile Lys Gln Gln
                165                 170                 175 atg gat caa aat tgg gta caa gat gat acc ttc gtt cca ctt aaa acc           576
Met Asp Gln Asn Trp Val Gln Asp Asp Thr Phe Val Pro Leu Lys Thr
                180                 185                 190 gtt aaa aaa atg gat gaa tat tta agt gat ttc gca aaa aaa ttt cat           624
Val Lys Lys Met Asp Glu Tyr Leu Ser Asp Phe Ala Lys Lys Phe His
                195                 200                 205 ctt aca act aat gaa aca gaa agt cgt aac tat cct cta gga aaa gcg           672
Leu Thr Thr Asn Glu Thr Glu Ser Arg Asn Tyr Pro Leu Gly Lys Ala
        210                 215                 220 act tca cat cta tta ggt tat gtt ggt ccc att aac tct gaa gaa tta           720
Thr Ser His Leu Leu Gly Tyr Val Gly Pro Ile Asn Ser Glu Glu Leu
225                 230                 235                 240 aaa caa aaa gaa tat aaa ggc tat aaa gat gat gca gtt att ggt aaa           768
Lys Gln Lys Glu Tyr Lys Gly Tyr Lys Asp Asp Ala Val Ile Gly Lys
                245                 250                 255 aag gga ctc gaa aaa ctt tac gat aaa aag ctc caa cat gaa gat ggc           816
Lys Gly Leu Glu Lys Leu Tyr Asp Lys Lys Leu Gln His Glu Asp Gly
                260                 265                 270 tat cgt gtc aca atc gtt gac gat aat agc aat aca atc gca cat aca           864
Tyr Arg Val Thr Ile Val Asp Asp Asn Ser Asn Thr Ile Ala His Thr
                275                 280                 285 tta ata gag aaa aag aaa aaa gat ggc aaa gat att caa cta act att           912
Leu Ile Glu Lys Lys Lys Lys Asp Gly Lys Asp Ile Gln Leu Thr Ile
        290                 295                 300 gat gct aaa gtt caa aag agt att tat aac aac atg aaa aat gat tat           960
Asp Ala Lys Val Gln Lys Ser Ile Tyr Asn Asn Met Lys Asn Asp Tyr
305                 310                 315                 320 ggc tca ggt act gct atc cac cct caa aca ggt gaa tta tta gca ctt          1008
Gly Ser Gly Thr Ala Ile His Pro Gln Thr Gly Glu Leu Leu Ala Leu
                325                 330                 335 gta agc aca cct tca tat gac gtc tat cca ttt atg tat ggc atg agt          1056
Val Ser Thr Pro Ser Tyr Asp Val Tyr Pro Phe Met Tyr Gly Met Ser
                340                 345                 350 aac gaa gaa tat aat aaa tta acc gaa gat aaa aaa gaa cct ctg ctc          1104
Asn Glu Glu Tyr Asn Lys Leu Thr Glu Asp Lys Lys Glu Pro Leu Leu
                355                 360                 365 aac aag ttc cag att aca act tca cca ggt tca act caa aaa ata tta          1152
```

```
Asn Lys Phe Gln Ile Thr Thr Ser Pro Gly Ser Thr Gln Lys Ile Leu
        370                 375                 380 aca gca atg att ggg tta aat aac aaa aca tta gac gat aaa aca agt    1200
Thr Ala Met Ile Gly Leu Asn Asn Lys Thr Leu Asp Asp Lys Thr Ser
385                 390                 395                 400 tat aaa atc gat ggt aaa ggt tgg caa aaa gat aaa tct tgg ggt ggt    1248
Tyr Lys Ile Asp Gly Lys Gly Trp Gln Lys Asp Lys Ser Trp Gly Gly
                405                 410                 415 tac aac gtt aca aga tat gaa gtg gta aat ggt aat atc gac tta aaa    1296
Tyr Asn Val Thr Arg Tyr Glu Val Val Asn Gly Asn Ile Asp Leu Lys
            420                 425                 430 caa gca ata gaa tca tca gat aac att ttc ttt gct aga gta gca ctc    1344
Gln Ala Ile Glu Ser Ser Asp Asn Ile Phe Phe Ala Arg Val Ala Leu
        435                 440                 445 gaa tta ggc agt aag aaa ttt gaa aaa ggc atg aaa aaa cta ggt gtt    1392
Glu Leu Gly Ser Lys Lys Phe Glu Lys Gly Met Lys Lys Leu Gly Val
450                 455                 460 ggt gaa gat ata cca agt gat tat cca ttt tat aat gct caa att tca    1440
Gly Glu Asp Ile Pro Ser Asp Tyr Pro Phe Tyr Asn Ala Gln Ile Ser
465                 470                 475                 480 aac aaa aat tta gat aat gaa ata tta tta gct gat tca ggt tac gga    1488
Asn Lys Asn Leu Asp Asn Glu Ile Leu Leu Ala Asp Ser Gly Tyr Gly
                485                 490                 495 caa ggt gaa ata ctg att aac cca gta cag atc ctt tca atc tat agc    1536
Gln Gly Glu Ile Leu Ile Asn Pro Val Gln Ile Leu Ser Ile Tyr Ser
            500                 505                 510 gca tta gaa aat aat ggc aat att aac gca cct cac tta tta aaa gac    1584
Ala Leu Glu Asn Asn Gly Asn Ile Asn Ala Pro His Leu Leu Lys Asp
        515                 520                 525 acg aaa aac aaa gtt tgg aag aaa aat att att tcc aaa gaa aat atc    1632
Thr Lys Asn Lys Val Trp Lys Lys Asn Ile Ile Ser Lys Glu Asn Ile
530                 535                 540 aat cta tta act gat ggt atg caa caa gtc gta aat aaa aca cat aaa    1680
Asn Leu Leu Thr Asp Gly Met Gln Gln Val Val Asn Lys Thr His Lys
545                 550                 555                 560 gaa gat att tat aga tct tat gca aac tta att ggc aaa tcc ggt act    1728
Glu Asp Ile Tyr Arg Ser Tyr Ala Asn Leu Ile Gly Lys Ser Gly Thr
                565                 570                 575 gca gaa ctc aaa atg aaa caa gga gaa act ggc aga caa att ggg tgg    1776
Ala Glu Leu Lys Met Lys Gln Gly Glu Thr Gly Arg Gln Ile Gly Trp
            580                 585                 590 ttt ata tca tat gat aaa gat aat cca aac atg atg atg gct att aat    1824
Phe Ile Ser Tyr Asp Lys Asp Asn Pro Asn Met Met Met Ala Ile Asn
        595                 600                 605 gtt aaa gat gta caa gat aaa gga atg gct agc tac aat gcc aaa atc    1872
Val Lys Asp Val Gln Asp Lys Gly Met Ala Ser Tyr Asn Ala Lys Ile
610                 615                 620 tca ggt aaa gtg tat gat gag cta tat gag aac ggt aat aaa aaa tac    1920
Ser Gly Lys Val Tyr Asp Glu Leu Tyr Glu Asn Gly Asn Lys Lys Tyr
625                 630                 635                 640 gat ata gat gaa                                                    1932
Asp Ile Asp Glu <210> SEQ ID NO 28
<211> LENGTH: 644
<212> TYPE: PRT
<213> ORGANISM: Staphylococcus aureus

<400> SEQUENCE: 28

Ser Lys Asp Lys Glu Ile Asn Asn Thr Ile Asp Ala Ile Glu Asp Lys
1               5                   10                  15
```

-continued

```
Asn Phe Lys Gln Val Tyr Lys Asp Ser Ser Tyr Ile Ser Lys Ser Asp
             20                  25                  30

Asn Gly Glu Val Glu Met Thr Glu Arg Pro Ile Lys Ile Tyr Asn Ser
         35                  40                  45

Leu Gly Val Lys Asp Ile Asn Ile Gln Asp Arg Lys Ile Lys Lys Val
 50                  55                  60

Ser Lys Asn Lys Lys Arg Val Asp Ala Gln Tyr Lys Ile Lys Thr Asn
 65                  70                  75                  80

Tyr Gly Asn Ile Asp Arg Asn Val Gln Phe Asn Phe Val Lys Glu Asp
                 85                  90                  95

Gly Met Trp Lys Leu Asp Trp Asp His Ser Val Ile Ile Pro Gly Met
            100                 105                 110

Gln Lys Asp Gln Ser Ile His Ile Glu Asn Leu Lys Ser Glu Arg Gly
            115                 120                 125

Lys Ile Leu Asp Arg Asn Asn Val Glu Leu Ala Asn Thr Gly Thr Ala
130                 135                 140

Tyr Glu Ile Gly Ile Val Pro Lys Asn Val Ser Lys Lys Asp Tyr Lys
145                 150                 155                 160

Ala Ile Ala Lys Glu Leu Ser Ile Ser Glu Asp Tyr Ile Lys Gln Gln
                165                 170                 175

Met Asp Gln Asn Trp Val Gln Asp Asp Thr Phe Val Pro Leu Lys Thr
            180                 185                 190

Val Lys Lys Met Asp Glu Tyr Leu Ser Asp Phe Ala Lys Lys Phe His
            195                 200                 205

Leu Thr Thr Asn Glu Thr Glu Ser Arg Asn Tyr Pro Leu Gly Lys Ala
210                 215                 220

Thr Ser His Leu Leu Gly Tyr Val Gly Pro Ile Asn Ser Glu Glu Leu
225                 230                 235                 240

Lys Gln Lys Glu Tyr Lys Gly Tyr Lys Asp Asp Ala Val Ile Gly Lys
                245                 250                 255

Lys Gly Leu Glu Lys Leu Tyr Asp Lys Lys Leu Gln His Glu Asp Gly
            260                 265                 270

Tyr Arg Val Thr Ile Val Asp Asp Asn Ser Asn Thr Ile Ala His Thr
            275                 280                 285

Leu Ile Glu Lys Lys Lys Lys Asp Gly Lys Asp Ile Gln Leu Thr Ile
290                 295                 300

Asp Ala Lys Val Gln Lys Ser Ile Tyr Asn Asn Met Lys Asn Asp Tyr
305                 310                 315                 320

Gly Ser Gly Thr Ala Ile His Pro Gln Thr Gly Glu Leu Leu Ala Leu
                325                 330                 335

Val Ser Thr Pro Ser Tyr Asp Val Tyr Pro Phe Met Tyr Gly Met Ser
            340                 345                 350

Asn Glu Glu Tyr Asn Lys Leu Thr Glu Asp Lys Lys Glu Pro Leu Leu
            355                 360                 365

Asn Lys Phe Gln Ile Thr Thr Ser Pro Gly Ser Thr Gln Lys Ile Leu
            370                 375                 380

Thr Ala Met Ile Gly Leu Asn Asn Lys Thr Leu Asp Asp Lys Thr Ser
385                 390                 395                 400

Tyr Lys Ile Asp Gly Lys Gly Trp Gln Lys Asp Lys Ser Trp Gly Gly
                405                 410                 415

Tyr Asn Val Thr Arg Tyr Glu Val Val Asn Gly Asn Ile Asp Leu Lys
            420                 425                 430

Gln Ala Ile Glu Ser Ser Asp Asn Ile Phe Phe Ala Arg Val Ala Leu
```

```
                    435                 440                 445
Glu Leu Gly Ser Lys Lys Phe Glu Lys Gly Met Lys Lys Leu Gly Val
    450                 455                 460

Gly Glu Asp Ile Pro Ser Asp Tyr Pro Phe Tyr Asn Ala Gln Ile Ser
465                 470                 475                 480

Asn Lys Asn Leu Asp Asn Glu Ile Leu Leu Ala Asp Ser Gly Tyr Gly
                485                 490                 495

Gln Gly Glu Ile Leu Ile Asn Pro Val Gln Ile Leu Ser Ile Tyr Ser
            500                 505                 510

Ala Leu Glu Asn Asn Gly Asn Ile Asn Ala Pro His Leu Leu Lys Asp
        515                 520                 525

Thr Lys Asn Lys Val Trp Lys Lys Asn Ile Ile Ser Lys Glu Asn Ile
    530                 535                 540

Asn Leu Leu Thr Asp Gly Met Gln Gln Val Val Asn Lys Thr His Lys
545                 550                 555                 560

Glu Asp Ile Tyr Arg Ser Tyr Ala Asn Leu Ile Gly Lys Ser Gly Thr
                565                 570                 575

Ala Glu Leu Lys Met Lys Gln Gly Glu Thr Gly Arg Gln Ile Gly Trp
            580                 585                 590

Phe Ile Ser Tyr Asp Lys Asp Asn Pro Asn Met Met Met Ala Ile Asn
        595                 600                 605

Val Lys Asp Val Gln Asp Lys Gly Met Ala Ser Tyr Asn Ala Lys Ile
    610                 615                 620

Ser Gly Lys Val Tyr Asp Glu Leu Tyr Glu Asn Gly Asn Lys Lys Tyr
625                 630                 635                 640

Asp Ile Asp Glu

<210> SEQ ID NO 29
<211> LENGTH: 675
<212> TYPE: DNA
<213> ORGANISM: Staphylococcus aureus
<220> FEATURE:
<221> NAME/KEY: CDS
<222> LOCATION: (1)..(675)

<400> SEQUENCE: 29 ttt gat gga agt ttt gtg ctt tat aat gaa cgg gag caa gct tat tct    48
Phe Asp Gly Ser Phe Val Leu Tyr Asn Glu Arg Glu Gln Ala Tyr Ser
1               5                   10                  15 att tat aat gaa cca gaa agt aaa caa cga tat tca cct aat tct act    96
Ile Tyr Asn Glu Pro Glu Ser Lys Gln Arg Tyr Ser Pro Asn Ser Thr
            20                  25                  30 tac aaa att tat tta gcg tta atg gca ttc gac caa aat tta ctc tca   144
Tyr Lys Ile Tyr Leu Ala Leu Met Ala Phe Asp Gln Asn Leu Leu Ser
        35                  40                  45 tta aat cat act gaa caa caa tgg gat aaa cat caa tat cca ttt aaa   192
Leu Asn His Thr Glu Gln Gln Trp Asp Lys His Gln Tyr Pro Phe Lys
    50                  55                  60 gaa tgg aac caa gat caa aat tta aat tct tca atg aaa tat tca gta   240
Glu Trp Asn Gln Asp Gln Asn Leu Asn Ser Ser Met Lys Tyr Ser Val
65                  70                  75                  80 aat tgg tat tac gaa aat tta aac aaa cat tta aga caa gat gag gtt   288
Asn Trp Tyr Tyr Glu Asn Leu Asn Lys His Leu Arg Gln Asp Glu Val
                85                  90                  95 aaa tct tat tta gat cta att gaa tat ggt aat gaa gaa ata tca ggg   336
Lys Ser Tyr Leu Asp Leu Ile Glu Tyr Gly Asn Glu Glu Ile Ser Gly
            100                 105                 110 aat gaa aat tat tgg aat gaa tct tca tta aaa att tct gca ata gaa   384
```

```
                Asn Glu Asn Tyr Trp Asn Glu Ser Ser Leu Lys Ile Ser Ala Ile Glu
                    115                 120                 125 cag gtt aat ttg ttg aaa aat atg aaa caa cat aac atg cat ttt gat              432
Gln Val Asn Leu Leu Lys Asn Met Lys Gln His Asn Met His Phe Asp
    130                 135                 140 aat aag gct att gaa aaa gtt gaa aat agt atg act ttg aaa caa aaa              480
Asn Lys Ala Ile Glu Lys Val Glu Asn Ser Met Thr Leu Lys Gln Lys
145                 150                 155                 160 gat act tat aaa tat gta ggt aaa act gga aca gga atc gtg aat cac              528
Asp Thr Tyr Lys Tyr Val Gly Lys Thr Gly Thr Gly Ile Val Asn His
                165                 170                 175 aaa gaa gca aat gga tgg ttc gta ggt tat gtt gaa acg aaa gat aat              576
Lys Glu Ala Asn Gly Trp Phe Val Gly Tyr Val Glu Thr Lys Asp Asn
                180                 185                 190 acg tat tat ttt gct aca cat tta aaa ggc gaa gac aat gcg aat ggc              624
Thr Tyr Tyr Phe Ala Thr His Leu Lys Gly Glu Asp Asn Ala Asn Gly
                195                 200                 205 gaa aaa gca caa caa att tct gag cgt att tta aaa gaa atg gag tta              672
Glu Lys Ala Gln Gln Ile Ser Glu Arg Ile Leu Lys Glu Met Glu Leu
    210                 215                 220 ata                                                                          675
Ile
225

<210> SEQ ID NO 30
<211> LENGTH: 225
<212> TYPE: PRT
<213> ORGANISM: Staphylococcus aureus

<400> SEQUENCE: 30

Phe Asp Gly Ser Phe Val Leu Tyr Asn Glu Arg Glu Gln Ala Tyr Ser
1               5                   10                  15

Ile Tyr Asn Glu Pro Glu Ser Lys Gln Arg Tyr Ser Pro Asn Ser Thr
            20                  25                  30

Tyr Lys Ile Tyr Leu Ala Leu Met Ala Phe Asp Gln Asn Leu Leu Ser
        35                  40                  45

Leu Asn His Thr Glu Gln Gln Trp Asp Lys His Gln Tyr Pro Phe Lys
    50                  55                  60

Glu Trp Asn Gln Asp Gln Asn Leu Asn Ser Ser Met Lys Tyr Ser Val
65                  70                  75                  80

Asn Trp Tyr Tyr Glu Asn Leu Asn Lys His Leu Arg Gln Asp Glu Val
                85                  90                  95

Lys Ser Tyr Leu Asp Leu Ile Glu Tyr Gly Asn Glu Glu Ile Ser Gly
            100                 105                 110

Asn Glu Asn Tyr Trp Asn Glu Ser Ser Leu Lys Ile Ser Ala Ile Glu
        115                 120                 125

Gln Val Asn Leu Leu Lys Asn Met Lys Gln His Asn Met His Phe Asp
    130                 135                 140

Asn Lys Ala Ile Glu Lys Val Glu Asn Ser Met Thr Leu Lys Gln Lys
145                 150                 155                 160

Asp Thr Tyr Lys Tyr Val Gly Lys Thr Gly Thr Gly Ile Val Asn His
                165                 170                 175

Lys Glu Ala Asn Gly Trp Phe Val Gly Tyr Val Glu Thr Lys Asp Asn
                180                 185                 190

Thr Tyr Tyr Phe Ala Thr His Leu Lys Gly Glu Asp Asn Ala Asn Gly
                195                 200                 205

Glu Lys Ala Gln Gln Ile Ser Glu Arg Ile Leu Lys Glu Met Glu Leu
    210                 215                 220
```

Ile
225

<210> SEQ ID NO 31
<211> LENGTH: 840
<212> TYPE: DNA
<213> ORGANISM: Staphylococcus epidermidis
<220> FEATURE:
<221> NAME/KEY: CDS
<222> LOCATION: (1)..(840)

<400> SEQUENCE: 31

| aaa | aag | tta | ata | ctt | tta | att | gca | att | gct | tta | gtt | tta | agt | gca | tgt | 48 |
| Lys | Lys | Leu | Ile | Leu | Leu | Ile | Ala | Ile | Ala | Leu | Val | Leu | Ser | Ala | Cys | |
| 1 | | | | 5 | | | | | 10 | | | | | 15 | | |

| aat | tca | acc | agt | tca | cat | gct | aaa | gag | tta | aat | aat | tta | gaa | aag | aaa | 96 |
| Asn | Ser | Thr | Ser | Ser | His | Ala | Lys | Glu | Leu | Asn | Asn | Leu | Glu | Lys | Lys | |
| | | | 20 | | | | | 25 | | | | | 30 | | | |

| tat | aat | gct | aat | att | ggt | gtc | tat | gca | tta | gat | act | aaa | agt | ggt | aag | 144 |
| Tyr | Asn | Ala | Asn | Ile | Gly | Val | Tyr | Ala | Leu | Asp | Thr | Lys | Ser | Gly | Lys | |
| | | 35 | | | | | 40 | | | | | 45 | | | | |

| gaa | gta | aaa | ttt | aat | gcc | gat | aag | aga | ttt | gcc | tat | gct | tca | act | tca | 192 |
| Glu | Val | Lys | Phe | Asn | Ala | Asp | Lys | Arg | Phe | Ala | Tyr | Ala | Ser | Thr | Ser | |
| | 50 | | | | | 55 | | | | | 60 | | | | | |

| aaa | gcg | ata | aat | agt | gct | att | ttg | tta | gaa | caa | gca | cct | tat | aat | aag | 240 |
| Lys | Ala | Ile | Asn | Ser | Ala | Ile | Leu | Leu | Glu | Gln | Ala | Pro | Tyr | Asn | Lys | |
| 65 | | | | | 70 | | | | | 75 | | | | | 80 | |

| tta | aat | aaa | aaa | gta | cat | att | aac | aaa | gat | gat | ata | gtt | gct | tat | tct | 288 |
| Leu | Asn | Lys | Lys | Val | His | Ile | Asn | Lys | Asp | Asp | Ile | Val | Ala | Tyr | Ser | |
| | | | | 85 | | | | | 90 | | | | | 95 | | |

| cct | att | tta | gaa | aaa | tat | gta | gga | aaa | gat | atc | act | tta | aaa | gaa | ctt | 336 |
| Pro | Ile | Leu | Glu | Lys | Tyr | Val | Gly | Lys | Asp | Ile | Thr | Leu | Lys | Glu | Leu | |
| | | | 100 | | | | | 105 | | | | | 110 | | | |

| att | gag | gct | tca | atg | aag | tat | agt | gat | aat | aca | gca | aac | aat | aaa | att | 384 |
| Ile | Glu | Ala | Ser | Met | Lys | Tyr | Ser | Asp | Asn | Thr | Ala | Asn | Asn | Lys | Ile | |
| | | 115 | | | | | 120 | | | | | 125 | | | | |

| ata | aac | gaa | atc | ggt | gga | atc | aaa | aaa | att | aaa | aaa | cgt | tta | aaa | aaa | 432 |
| Ile | Asn | Glu | Ile | Gly | Gly | Ile | Lys | Lys | Ile | Lys | Lys | Arg | Leu | Lys | Lys | |
| | 130 | | | | | 135 | | | | | 140 | | | | | |

| ttg | gga | gat | aaa | gta | aca | aat | cca | gtt | aga | tat | gaa | ata | gaa | tta | aat | 480 |
| Leu | Gly | Asp | Lys | Val | Thr | Asn | Pro | Val | Arg | Tyr | Glu | Ile | Glu | Leu | Asn | |
| 145 | | | | | 150 | | | | | 155 | | | | | 160 | |

| tac | tat | tca | cca | aag | agc | aaa | aaa | gat | act | tca | acg | cct | gct | gct | ttc | 528 |
| Tyr | Tyr | Ser | Pro | Lys | Ser | Lys | Lys | Asp | Thr | Ser | Thr | Pro | Ala | Ala | Phe | |
| | | | | 165 | | | | | 170 | | | | | 175 | | |

| ggc | aag | act | tta | aat | aaa | ctt | atc | gca | aat | gga | aaa | tta | agc | aaa | aaa | 576 |
| Gly | Lys | Thr | Leu | Asn | Lys | Leu | Ile | Ala | Asn | Gly | Lys | Leu | Ser | Lys | Lys | |
| | | | 180 | | | | | 185 | | | | | 190 | | | |

| aat | aaa | aat | ttc | tta | ctt | gat | tta | atg | tta | aat | aat | aaa | aac | gga | gac | 624 |
| Asn | Lys | Asn | Phe | Leu | Leu | Asp | Leu | Met | Leu | Asn | Asn | Lys | Asn | Gly | Asp | |
| | | 195 | | | | | 200 | | | | | 205 | | | | |

| act | tta | att | aaa | gat | ggt | gtt | cca | aaa | gac | tat | aag | gtt | gct | gat | aaa | 672 |
| Thr | Leu | Ile | Lys | Asp | Gly | Val | Pro | Lys | Asp | Tyr | Lys | Val | Ala | Asp | Lys | |
| | 210 | | | | | 215 | | | | | 220 | | | | | |

| agt | ggt | caa | gca | ata | aca | tat | gct | tct | aga | aat | gat | gta | gct | ttt | att | 720 |
| Ser | Gly | Gln | Ala | Ile | Thr | Tyr | Ala | Ser | Arg | Asn | Asp | Val | Ala | Phe | Ile | |
| 225 | | | | | 230 | | | | | 235 | | | | | 240 | |

| tat | cct | aag | aac | caa | tct | gaa | cct | att | att | tta | gtc | att | ttt | acg | aat | 768 |
| Tyr | Pro | Lys | Asn | Gln | Ser | Glu | Pro | Ile | Ile | Leu | Val | Ile | Phe | Thr | Asn | |
| | | | | 245 | | | | | 250 | | | | | 255 | | |

| aaa | gac | aat | aaa | agt | gat | aaa | cct | aat | gat | aaa | ttg | ata | agt | gaa | acc | 816 |

```
Lys Asp Asn Lys Ser Asp Lys Pro Asn Asp Lys Leu Ile Ser Glu Thr
        260                 265                 270 gcc aag aat gta ata aac aaa ttt                                              840
Ala Lys Asn Val Ile Asn Lys Phe
        275                 280

<210> SEQ ID NO 32
<211> LENGTH: 280
<212> TYPE: PRT
<213> ORGANISM: Staphylococcus epidermidis

<400> SEQUENCE: 32

Lys Lys Leu Ile Leu Leu Ile Ala Ile Ala Leu Val Leu Ser Ala Cys
1               5                   10                  15

Asn Ser Thr Ser Ser His Ala Lys Glu Leu Asn Asn Leu Glu Lys Lys
            20                  25                  30

Tyr Asn Ala Asn Ile Gly Val Tyr Ala Leu Asp Thr Lys Ser Gly Lys
        35                  40                  45

Glu Val Lys Phe Asn Ala Asp Lys Arg Phe Ala Tyr Ala Ser Thr Ser
    50                  55                  60

Lys Ala Ile Asn Ser Ala Ile Leu Leu Glu Gln Ala Pro Tyr Asn Lys
65                  70                  75                  80

Leu Asn Lys Lys Val His Ile Asn Lys Asp Asp Ile Val Ala Tyr Ser
                85                  90                  95

Pro Ile Leu Glu Lys Tyr Val Gly Lys Asp Ile Thr Leu Lys Glu Leu
            100                 105                 110

Ile Glu Ala Ser Met Lys Tyr Ser Asp Asn Thr Ala Asn Asn Lys Ile
        115                 120                 125

Ile Asn Glu Ile Gly Gly Ile Lys Lys Ile Lys Lys Arg Leu Lys Lys
    130                 135                 140

Leu Gly Asp Lys Val Thr Asn Pro Val Arg Tyr Glu Ile Glu Leu Asn
145                 150                 155                 160

Tyr Tyr Ser Pro Lys Ser Lys Lys Asp Thr Ser Thr Pro Ala Ala Phe
                165                 170                 175

Gly Lys Thr Leu Asn Lys Leu Ile Ala Asn Gly Lys Leu Ser Lys Lys
            180                 185                 190

Asn Lys Asn Phe Leu Leu Asp Leu Met Leu Asn Asn Lys Asn Gly Asp
        195                 200                 205

Thr Leu Ile Lys Asp Gly Val Pro Lys Asp Tyr Lys Val Ala Asp Lys
    210                 215                 220

Ser Gly Gln Ala Ile Thr Tyr Ala Ser Arg Asn Asp Val Ala Phe Ile
225                 230                 235                 240

Tyr Pro Lys Asn Gln Ser Glu Pro Ile Ile Leu Val Ile Phe Thr Asn
                245                 250                 255

Lys Asp Asn Lys Ser Asp Lys Pro Asn Asp Lys Leu Ile Ser Glu Thr
            260                 265                 270

Ala Lys Asn Val Ile Asn Lys Phe
        275                 280

<210> SEQ ID NO 33
<211> LENGTH: 714
<212> TYPE: DNA
<213> ORGANISM: Staphylococcus epidermidis
<220> FEATURE:
<221> NAME/KEY: CDS
<222> LOCATION: (1)..(714)

<400> SEQUENCE: 33
```

```
tta cca gaa ggc gac ttc cct gaa act aca gaa aaa ata cct gca atg      48
Leu Pro Glu Gly Asp Phe Pro Glu Thr Thr Glu Lys Ile Pro Ala Met
 1               5                  10                  15 cgc aaa gca att gct aaa gca atg gtt aat tct aaa cac act gca cct      96
Arg Lys Ala Ile Ala Lys Ala Met Val Asn Ser Lys His Thr Ala Pro
            20                  25                  30 cat gtt aca tta atg gat gaa att gat gtg caa gaa tta tgg gat cac     144
His Val Thr Leu Met Asp Glu Ile Asp Val Gln Glu Leu Trp Asp His
        35                  40                  45 cgt aag aaa ttt aaa gaa att gct gct gaa caa ggt aca aaa ctt act     192
Arg Lys Lys Phe Lys Glu Ile Ala Ala Glu Gln Gly Thr Lys Leu Thr
50                  55                  60 ttc tta cca tat gtt gtt aaa gca tta gtt tct gca ctt aaa aaa tat     240
Phe Leu Pro Tyr Val Val Lys Ala Leu Val Ser Ala Leu Lys Lys Tyr
65                  70                  75                  80 cca gca ctt aat act tct ttc aat gaa gaa gct gga gag gtt gta cac     288
Pro Ala Leu Asn Thr Ser Phe Asn Glu Glu Ala Gly Glu Val Val His
                85                  90                  95 aaa cat tac tgg aat att ggt att gct gca gat acg gat aaa gga tta     336
Lys His Tyr Trp Asn Ile Gly Ile Ala Ala Asp Thr Asp Lys Gly Leu
            100                 105                 110 tta gta cca gta gtt aaa cat gcc gat cgt aaa tca ata ttc gaa att     384
Leu Val Pro Val Val Lys His Ala Asp Arg Lys Ser Ile Phe Glu Ile
        115                 120                 125 tct gat gaa att aat gaa cta gct gta aaa gca cgt gat ggt aaa tta     432
Ser Asp Glu Ile Asn Glu Leu Ala Val Lys Ala Arg Asp Gly Lys Leu
130                 135                 140 act tca gaa gaa atg aaa ggt gca aca tgc aca att agt aat atc ggt     480
Thr Ser Glu Glu Met Lys Gly Ala Thr Cys Thr Ile Ser Asn Ile Gly
145                 150                 155                 160 tcc gct ggt gga caa tgg ttc act cca gtt atc aat cac cca gaa gta     528
Ser Ala Gly Gly Gln Trp Phe Thr Pro Val Ile Asn His Pro Glu Val
                165                 170                 175 gct atc tta gga att ggc cgt atc gct caa aaa cct atc gtt aaa gat     576
Ala Ile Leu Gly Ile Gly Arg Ile Ala Gln Lys Pro Ile Val Lys Asp
            180                 185                 190 gga gaa att gta gct gca cca gtg tta gct tta tca tta agc ttt gac     624
Gly Glu Ile Val Ala Ala Pro Val Leu Ala Leu Ser Leu Ser Phe Asp
        195                 200                 205 cat aga caa atc gat ggt gct act gga caa aat gct atg aat cac att     672
His Arg Gln Ile Asp Gly Ala Thr Gly Gln Asn Ala Met Asn His Ile
210                 215                 220 aaa cgc tta tta aat aat cca gaa tta tta tta atg gag ggg             714
Lys Arg Leu Leu Asn Asn Pro Glu Leu Leu Leu Met Glu Gly
225                 230                 235

<210> SEQ ID NO 34
<211> LENGTH: 238
<212> TYPE: PRT
<213> ORGANISM: Staphylococcus epidermidis

<400> SEQUENCE: 34

Leu Pro Glu Gly Asp Phe Pro Glu Thr Thr Glu Lys Ile Pro Ala Met
 1               5                  10                  15

Arg Lys Ala Ile Ala Lys Ala Met Val Asn Ser Lys His Thr Ala Pro
            20                  25                  30

His Val Thr Leu Met Asp Glu Ile Asp Val Gln Glu Leu Trp Asp His
        35                  40                  45

Arg Lys Lys Phe Lys Glu Ile Ala Ala Glu Gln Gly Thr Lys Leu Thr
50                  55                  60
```

```
Phe Leu Pro Tyr Val Val Lys Ala Leu Val Ser Ala Leu Lys Lys Tyr
 65                  70                  75                  80

Pro Ala Leu Asn Thr Ser Phe Asn Glu Glu Ala Gly Glu Val Val His
                 85                  90                  95

Lys His Tyr Trp Asn Ile Gly Ile Ala Ala Asp Thr Asp Lys Gly Leu
            100                 105                 110

Leu Val Pro Val Val Lys His Ala Asp Arg Lys Ser Ile Phe Glu Ile
        115                 120                 125

Ser Asp Glu Ile Asn Glu Leu Ala Val Lys Ala Arg Asp Gly Lys Leu
130                 135                 140

Thr Ser Glu Glu Met Lys Gly Ala Thr Cys Thr Ile Ser Asn Ile Gly
145                 150                 155                 160

Ser Ala Gly Gly Gln Trp Phe Thr Pro Val Ile Asn His Pro Glu Val
                165                 170                 175

Ala Ile Leu Gly Ile Gly Arg Ile Ala Gln Lys Pro Ile Val Lys Asp
            180                 185                 190

Gly Glu Ile Val Ala Ala Pro Val Leu Ala Leu Ser Leu Ser Phe Asp
        195                 200                 205

His Arg Gln Ile Asp Gly Ala Thr Gly Gln Asn Ala Met Asn His Ile
210                 215                 220

Lys Arg Leu Leu Asn Asn Pro Glu Leu Leu Leu Met Glu Gly
225                 230                 235

<210> SEQ ID NO 35
<211> LENGTH: 1296
<212> TYPE: DNA
<213> ORGANISM: Staphylococcus epidermidis
<220> FEATURE:
<221> NAME/KEY: CDS
<222> LOCATION: (1)..(1296)

<400> SEQUENCE: 35 gca ttt gaa ttt aga tta ccc gat atc ggg gaa ggt atc cac gaa ggt        48
Ala Phe Glu Phe Arg Leu Pro Asp Ile Gly Glu Gly Ile His Glu Gly
1               5                   10                  15 gaa att gtt aaa tgg ttt att aaa gcc ggc gat aca att gaa gaa gat        96
Glu Ile Val Lys Trp Phe Ile Lys Ala Gly Asp Thr Ile Glu Glu Asp
            20                  25                  30 gat gta tta gca gaa gtt caa aat gat aaa tct gta gta gaa att cct       144
Asp Val Leu Ala Glu Val Gln Asn Asp Lys Ser Val Val Glu Ile Pro
        35                  40                  45 tct cca gta agt ggt act gtt gaa gaa gtg tta gta gat gaa gga aca       192
Ser Pro Val Ser Gly Thr Val Glu Glu Val Leu Val Asp Glu Gly Thr
    50                  55                  60 gtg gca gta gta gga gat gtc atc gtt aaa att gat gca cct gat gca       240
Val Ala Val Val Gly Asp Val Ile Val Lys Ile Asp Ala Pro Asp Ala
65                  70                  75                  80 gaa gaa atg caa ttt aaa ggt cat ggc gat gat gag gat tct aag aaa       288
Glu Glu Met Gln Phe Lys Gly His Gly Asp Asp Glu Asp Ser Lys Lys
                85                  90                  95 gaa gaa aaa gaa caa gaa tca cca gtg caa gaa gaa gct tca tca act       336
Glu Glu Lys Glu Gln Glu Ser Pro Val Gln Glu Glu Ala Ser Ser Thr
            100                 105                 110 caa tca caa gaa aag aca gaa gta gat gaa agt aaa act gtt aaa gcg       384
Gln Ser Gln Glu Lys Thr Glu Val Asp Glu Ser Lys Thr Val Lys Ala
        115                 120                 125
```

```
atg ccg tca gtg cgt aag tat gca cgt gaa aat ggt gtc aat att aaa      432
Met Pro Ser Val Arg Lys Tyr Ala Arg Glu Asn Gly Val Asn Ile Lys
    130                 135                 140 gct gta aat ggt tct ggt aaa aat gga cga atc aca aaa gaa gac atc      480
Ala Val Asn Gly Ser Gly Lys Asn Gly Arg Ile Thr Lys Glu Asp Ile
145                 150                 155                 160 gat gca tac tta aat ggt ggt agt tcc gaa gaa ggt tca aac act agc      528
Asp Ala Tyr Leu Asn Gly Gly Ser Ser Glu Glu Gly Ser Asn Thr Ser
                165                 170                 175 gta gca tct gaa tca act tct agt gat gtc gtt aat gct tct gca aca      576
Val Ala Ser Glu Ser Thr Ser Ser Asp Val Val Asn Ala Ser Ala Thr
            180                 185                 190 caa gca tta cca gaa ggc gac ttc cct gaa act aca gaa aaa ata cct      624
Gln Ala Leu Pro Glu Gly Asp Phe Pro Glu Thr Thr Glu Lys Ile Pro
        195                 200                 205 gca atg cgc aaa gca att gct aaa gca atg gtt aat tct aaa cac act      672
Ala Met Arg Lys Ala Ile Ala Lys Ala Met Val Asn Ser Lys His Thr
    210                 215                 220 gca cct cat gtt aca tta atg gat gaa att gat gtg caa gaa tta tgg      720
Ala Pro His Val Thr Leu Met Asp Glu Ile Asp Val Gln Glu Leu Trp
225                 230                 235                 240 gat cac cgt aag aaa ttt aaa gaa att gct gct gaa caa ggt aca aaa      768
Asp His Arg Lys Lys Phe Lys Glu Ile Ala Ala Glu Gln Gly Thr Lys
                245                 250                 255 ctt act ttc tta cca tat gtt gtt aaa gca tta gtt tct gca ctt aaa      816
Leu Thr Phe Leu Pro Tyr Val Val Lys Ala Leu Val Ser Ala Leu Lys
            260                 265                 270 aaa tat cca gca ctt aat act tct ttc aat gaa gaa gct gga gag gtt      864
Lys Tyr Pro Ala Leu Asn Thr Ser Phe Asn Glu Glu Ala Gly Glu Val
        275                 280                 285 gta cac aaa cat tac tgg aat att ggt att gct gca gat acg gat aaa      912
Val His Lys His Tyr Trp Asn Ile Gly Ile Ala Ala Asp Thr Asp Lys
    290                 295                 300 gga tta tta gta cca gta gtt aaa cat gcc gat cgt aaa tca ata ttc      960
Gly Leu Leu Val Pro Val Val Lys His Ala Asp Arg Lys Ser Ile Phe
305                 310                 315                 320 gaa att tct gat gaa att aat gaa cta gct gta aaa gca cgt gat ggt     1008
Glu Ile Ser Asp Glu Ile Asn Glu Leu Ala Val Lys Ala Arg Asp Gly
                325                 330                 335 aaa tta act tca gaa gaa atg aaa ggt gca aca tgc aca att agt aat     1056
Lys Leu Thr Ser Glu Glu Met Lys Gly Ala Thr Cys Thr Ile Ser Asn
            340                 345                 350 atc ggt tcc gct ggt gga caa tgg ttc act cca gtt atc aat cac cca     1104
Ile Gly Ser Ala Gly Gly Gln Trp Phe Thr Pro Val Ile Asn His Pro
        355                 360                 365 gaa gta gct atc tta gga att ggc cgt atc gct caa aaa cct atc gtt     1152
Glu Val Ala Ile Leu Gly Ile Gly Arg Ile Ala Gln Lys Pro Ile Val
    370                 375                 380 aaa gat gga gaa att gta gct gca cca gtg tta gct tta tca tta agc     1200
Lys Asp Gly Glu Ile Val Ala Ala Pro Val Leu Ala Leu Ser Leu Ser
385                 390                 395                 400 ttt gac cat aga caa atc gat ggt gct act gga caa aat gct atg aat     1248
Phe Asp His Arg Gln Ile Asp Gly Ala Thr Gly Gln Asn Ala Met Asn
                405                 410                 415 cac att aaa cgc tta tta aat aat cca gaa tta tta tta atg gag ggg     1296
His Ile Lys Arg Leu Leu Asn Asn Pro Glu Leu Leu Leu Met Glu Gly
            420                 425                 430

<210> SEQ ID NO 36
<211> LENGTH: 432
<212> TYPE: PRT
```

<213> ORGANISM: Staphylococcus epidermidis

<400> SEQUENCE: 36

```
Ala Phe Glu Phe Arg Leu Pro Asp Ile Gly Glu Gly Ile His Glu Gly
1               5                   10                  15

Glu Ile Val Lys Trp Phe Ile Lys Ala Gly Asp Thr Ile Glu Glu Asp
            20                  25                  30

Asp Val Leu Ala Glu Val Gln Asn Asp Lys Ser Val Val Glu Ile Pro
        35                  40                  45

Ser Pro Val Ser Gly Thr Val Glu Val Leu Val Asp Gly Gly Thr
    50                  55                  60

Val Ala Val Val Gly Asp Val Ile Val Lys Ile Asp Ala Pro Asp Ala
65                  70                  75                  80

Glu Glu Met Gln Phe Lys Gly His Gly Asp Asp Glu Asp Ser Lys Lys
                85                  90                  95

Glu Glu Lys Glu Gln Glu Ser Pro Val Gln Glu Ala Ser Ser Thr
            100                 105                 110

Gln Ser Gln Glu Lys Thr Glu Val Asp Glu Ser Lys Thr Val Lys Ala
        115                 120                 125

Met Pro Ser Val Arg Lys Tyr Ala Arg Glu Asn Gly Val Asn Ile Lys
    130                 135                 140

Ala Val Asn Gly Ser Gly Lys Asn Gly Arg Ile Thr Lys Glu Asp Ile
145                 150                 155                 160

Asp Ala Tyr Leu Asn Gly Gly Ser Ser Glu Glu Gly Ser Asn Thr Ser
                165                 170                 175

Val Ala Ser Glu Ser Thr Ser Ser Asp Val Val Asn Ala Ser Ala Thr
            180                 185                 190

Gln Ala Leu Pro Glu Gly Asp Phe Pro Glu Thr Thr Glu Lys Ile Pro
        195                 200                 205

Ala Met Arg Lys Ala Ile Ala Lys Ala Met Val Asn Ser Lys His Thr
    210                 215                 220

Ala Pro His Val Thr Leu Met Asp Glu Ile Asp Val Gln Glu Leu Trp
225                 230                 235                 240

Asp His Arg Lys Lys Phe Lys Glu Ile Ala Ala Glu Gln Gly Thr Lys
                245                 250                 255

Leu Thr Phe Leu Pro Tyr Val Val Lys Ala Leu Val Ser Ala Leu Lys
            260                 265                 270

Lys Tyr Pro Ala Leu Asn Thr Ser Phe Asn Glu Glu Ala Gly Glu Val
        275                 280                 285

Val His Lys His Tyr Trp Asn Ile Gly Ile Ala Ala Asp Thr Asp Lys
    290                 295                 300

Gly Leu Leu Val Pro Val Lys His Ala Asp Arg Lys Ser Ile Phe
305                 310                 315                 320

Glu Ile Ser Asp Glu Ile Asn Glu Leu Ala Val Lys Ala Arg Asp Gly
                325                 330                 335

Lys Leu Thr Ser Glu Glu Met Lys Gly Ala Thr Cys Thr Ile Ser Asn
            340                 345                 350

Ile Gly Ser Ala Gly Gly Gln Trp Phe Thr Pro Val Ile Asn His Pro
        355                 360                 365

Glu Val Ala Ile Leu Gly Ile Gly Arg Ile Ala Gln Lys Pro Ile Val
    370                 375                 380

Lys Asp Gly Glu Ile Val Ala Ala Pro Val Leu Ala Leu Ser Leu Ser
```

-continued

```
                385                 390                 395                 400

Phe Asp His Arg Gln Ile Asp Gly Ala Thr Gly Gln Asn Ala Met Asn
                405                 410                 415

His Ile Lys Arg Leu Leu Asn Asn Pro Glu Leu Leu Leu Met Glu Gly
                420                 425                 430
```